(12) United States Patent  
Xue et al.

(10) Patent No.: US 11,353,448 B2  
(45) Date of Patent: Jun. 7, 2022

(54) METHODS AND COMPOSITIONS FOR QUANTIFYING METABOLITES AND PROTEINS FROM SINGLE CELLS

(71) Applicant: CALIFORNIA INSTITUTE OF TECHNOLOGY, Pasadena, CA (US)

(72) Inventors: Min Xue, Pasadena, CA (US); Wei Wei, Pasadena, CA (US); James R. Heath, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 299 days.

(21) Appl. No.: 15/045,241

(22) Filed: Feb. 16, 2016

(65) Prior Publication Data

US 2016/0238594 A1 Aug. 18, 2016

Related U.S. Application Data

(60) Provisional application No. 62/116,246, filed on Feb. 13, 2015, provisional application No. 62/265,211, filed on Dec. 9, 2015.

(51) Int. Cl.
*G01N 33/53* (2006.01)
*G01N 33/573* (2006.01)

(52) U.S. Cl.
CPC ....... *G01N 33/5308* (2013.01); *G01N 33/573* (2013.01)

(58) Field of Classification Search
IPC ...................................... G01N 33/5308,33/572
See application file for complete search history.

(56) References Cited

U.S. PATENT DOCUMENTS

| | | | |
|---|---|---|---|
| 5,858,801 A | 1/1999 | Brizzolara | |
| 6,039,897 A | 3/2000 | Lockhead et al. | |
| 6,165,739 A | 12/2000 | Clatch | |
| 6,377,721 B1 | 4/2002 | Walt et al. | |
| 6,429,027 B1 | 8/2002 | Chee et al. | |
| 6,524,790 B1 | 2/2003 | Kopf et al. | |
| 6,699,665 B1 | 3/2004 | Kim et al. | |
| 6,924,153 B1 | 5/2005 | Boehringer | |
| 7,312,197 B2* | 12/2007 | Gong ................ | A61K 38/1709 514/15.7 |
| 7,381,375 B2 | 6/2008 | Ravkin et al. | |
| 8,105,845 B2 | 1/2012 | Notcovich | |
| 8,394,590 B2 | 3/2013 | Kwong et al. | |
| 8,460,878 B2 | 6/2013 | Walt et al. | |
| 8,492,165 B2 | 7/2013 | Van Pelt et al. | |
| 8,865,479 B2 | 10/2014 | Love et al. | |
| 9,188,586 B2 | 11/2015 | Fan et al. | |
| 9,506,917 B2 | 11/2016 | Fan et al. | |
| 9,824,870 B1 | 11/2017 | Straume | |
| 9,952,126 B2* | 4/2018 | Fowler ................... | C12P 19/34 |
| 10,274,486 B2 | 4/2019 | Fan et al. | |
| 10,584,366 B2 | 3/2020 | Paczkowski et al. | |
| 2001/0016320 A1 | 8/2001 | He | |
| 2002/0090649 A1 | 7/2002 | Chan | |
| 2002/0100714 A1 | 8/2002 | Staats | |
| 2002/0131974 A1 | 9/2002 | Segal | |
| 2002/0146745 A1 | 10/2002 | Natan et al. | |
| 2003/0013091 A1 | 1/2003 | Dmitrov | |
| 2003/0082601 A1 | 5/2003 | Dill | |
| 2003/0096232 A1 | 5/2003 | Kris et al. | |
| 2003/0104486 A1* | 6/2003 | Selvan ................ | B01J 19/0046 506/3 |
| 2003/0127610 A1 | 7/2003 | Gallagher | |
| 2003/0190608 A1 | 10/2003 | Blackburb | |
| 2003/0190689 A1 | 10/2003 | Crosby | |
| 2004/0092032 A1 | 5/2004 | Winkler | |
| 2004/0191124 A1 | 9/2004 | Noetzel | |
| 2004/0224321 A1 | 11/2004 | Nicolau | |
| 2004/0265889 A1 | 12/2004 | Durham | |
| 2005/0032144 A1* | 2/2005 | Lombardi ............ | G01N 33/535 435/15 |
| 2005/0142033 A1 | 6/2005 | Glezer | |
| 2005/0197311 A1* | 9/2005 | Cooper ............... | C07K 14/4702 514/44 A |
| 2005/0226779 A1* | 10/2005 | Oldham ................ | B01L 3/5027 422/400 |
| 2006/0246475 A1 | 11/2006 | Crosby | |
| 2006/0263818 A1 | 11/2006 | Scherer | |
| 2006/0286549 A1* | 12/2006 | Sohn ................... | G01N 15/1031 435/5 |
| 2007/0074972 A1 | 4/2007 | Nassef | |
| 2007/0122819 A1 | 5/2007 | Wu | |
| 2007/0202538 A1 | 8/2007 | Glezer et al. | |
| 2008/0200343 A1 | 8/2008 | Clemens | |
| 2008/0207461 A1 | 8/2008 | Ermantraut et al. | |
| 2008/0317627 A1 | 12/2008 | Shirai et al. | |

(Continued)

FOREIGN PATENT DOCUMENTS

| | | |
|---|---|---|
| CN | 102690786 A | 9/2012 |
| DE | 10127221 A1 | 11/2002 |
| EP | 1816476 | 8/2007 |
| EP | 2 336 348 A1 | 6/2011 |
| JP | 2010-066146 A | 3/2010 |

(Continued)

OTHER PUBLICATIONS

Ivanova et al. "Polymer Microstructures Fabricated via Laser Ablatoin Used for Multianalyte Protein Microassay", Langmuir 2002, 18, 9539-9546.*

(Continued)

*Primary Examiner* — Ann Montgomery

(74) *Attorney, Agent, or Firm* — Lewis Roca Rothgerber Christie LLP

(57) ABSTRACT

Methods and compositions for quantifying the cellular concentration of cyclic adenosine monophosphate (cAMP), cyclic guanine monophosphate (cGMP), glutathione, glucose, and glutamine in a single cell include the use of conjugates and analogs in immunofluorescent assays for on-chip quantification. These metabolite immunofluorescent assays may be incorporated with proteomic assays for simultaneous single cell analysis of metabolites and proteins.

15 Claims, 38 Drawing Sheets
(38 of 38 Drawing Sheet(s) Filed in Color)
Specification includes a Sequence Listing.

(56) References Cited

U.S. PATENT DOCUMENTS

| | | | |
|---|---|---|---|
| 2009/0017455 A1 | 1/2009 | Kwong | |
| 2009/0036324 A1 | 2/2009 | Fan | |
| 2009/0053732 A1 | 2/2009 | Vermesh et al. | |
| 2009/0098541 A1* | 4/2009 | Southern | C12Q 1/6876 435/6.11 |
| 2009/0137413 A1 | 5/2009 | Mehta et al. | |
| 2009/0227043 A1* | 9/2009 | Huang | G01N 33/542 436/501 |
| 2010/0009335 A1 | 1/2010 | Joseph | |
| 2010/0152054 A1 | 6/2010 | Love et al. | |
| 2010/0297145 A1 | 11/2010 | Tsujikawa et al. | |
| 2011/0034908 A1* | 2/2011 | Hyde | A61M 5/14276 604/891.1 |
| 2011/0048952 A1 | 3/2011 | Van Pelt et al. | |
| 2011/0177537 A1* | 7/2011 | Nissum | G01N 33/74 435/7.93 |
| 2012/0015824 A1 | 1/2012 | Love et al. | |
| 2014/0170642 A1 | 6/2014 | Huang et al. | |
| 2015/0078999 A1 | 3/2015 | Heath et al. | |
| 2015/0086424 A1 | 3/2015 | Putnam et al. | |
| 2015/0204862 A1 | 7/2015 | Fan et al. | |
| 2015/0204864 A1 | 7/2015 | Fan et al. | |
| 2016/0129445 A1 | 5/2016 | Corey et al. | |
| 2016/0167049 A1 | 6/2016 | Narahara et al. | |
| 2016/0238594 A1 | 8/2016 | Xue et al. | |
| 2016/0252495 A1* | 9/2016 | Ricicova | G01N 33/505 506/9 |
| 2017/0067887 A1 | 3/2017 | Fan et al. | |
| 2017/0138942 A1* | 5/2017 | Fan | B01L 3/502753 |
| 2018/0105855 A1 | 4/2018 | Paczkowski et al. | |
| 2019/0285626 A1 | 9/2019 | Ng et al. | |
| 2019/0376898 A1 | 12/2019 | Tsiomplikas et al. | |
| 2020/0166518 A1 | 5/2020 | Paczkowski et al. | |
| 2020/0239926 A1 | 7/2020 | Paczkowski et al. | |

FOREIGN PATENT DOCUMENTS

| | | |
|---|---|---|
| WO | WO 96/28538 A1 | 9/1996 |
| WO | WO 02/077259 A2 | 10/2002 |
| WO | WO 2003/048736 | 6/2003 |
| WO | WO 2005/007892 | 1/2005 |
| WO | WO 2005/081867 | 9/2005 |
| WO | WO 2005/090972 | 9/2005 |
| WO | WO 2006/117541 | 11/2006 |
| WO | WO 2007/014267 | 2/2007 |
| WO | WO 2007/035633 A2 | 3/2007 |
| WO | WO 2008/016680 | 2/2008 |
| WO | WO 2009/012340 | 1/2009 |
| WO | WO 2009/012343 A2 | 1/2009 |
| WO | WO 2010/065929 A2 | 6/2010 |
| WO | WO 2013/090404 A2 | 6/2013 |
| WO | WO 2013/148448 A1 | 10/2013 |
| WO | WO 2014/031997 A1 | 2/2014 |
| WO | WO 2014/052989 A2 | 4/2014 |
| WO | WO 2016/057552 A1 | 4/2016 |
| WO | WO 2016/057705 A1 | 4/2016 |
| WO | WO 2016/090148 A1 | 6/2016 |
| WO | WO 2016/090320 A1 | 6/2016 |

OTHER PUBLICATIONS

Bailey, Ryan C. et al.; "DNA-Encoded Antibody Libraries: A Unified Platform for Multiplexed Cell Sorting and Detection of Genes and Proteins"; J. A,. Chem. Soc.; 2007; 129; pp. 1959-1967.
Deyle, Kaycie M. et al.; "Protein-targeting strategy used to develop a selective inhibitor of the E17K point mutation in the PH domain of Akt1"; Nat. Chem.; May 2015; 7(5); pp. 455-462.
Krzywinski, Martin et al.; "Circos: An information aesthetic for comparative genomics"; Genome Res.; 2009; 19; pp. 1639-1645.
Nathanson, David A. et al.; "Co-targeting of convergent nucleotide biosynthetic pathways for leukemia eradication"; J. Exp. Med.; 2014; vol. 211; No. 3; pp. 473-486.
Wise, David R. et al.; "Glutamine Addiction: A New Therapeutic Target in Cancer"; Trends. Biochem. Sci.; Aug. 2010; 35(8); pp. 427-433.
Yu, Jing et al.; "Microfluidics-Based Single-Cell Functional Proteomics for Fundamental and Applied Biomedical Applications"; Annual Review of Analytical Chemistry; Jun. 2014; vol. 7; pp. 275-295.
Baines, A.T. et al., Inhibition of RAS for cancer treatment: the search continues, NIH Public Access, Author Manuscript, Future Med Chem, Oct. 2011, 3(14) pp. 1787-1808.
Das, Samir, et al., A General Synthetic Approach for Designing Epitope Targeted Macrocyclic Peptide Ligands, Angewandte Chemie, 2015, 54:13219-13224.
Dirks, R.M., Paradigms for computational nucleic acid design, Nucleic Acids Research, vol. 32, No. 4, 2004, pp. 1392-1403.
Downward, J., Targeting RAS Signalling Pathways in Cancer Therapy, Nature Reviews, vol. 3, Jan. 2003, 22 pages.
Ostrem, J.M. et al., K-Ras(G12C) inhibitors allosterically control GTP affinity and effector interactions, Nature, vol. 503, Nov. 28, 2013, 14 pages.
Schubbert, S. et al., Hyperactive Ras in developmental disorders and cancer, Nature Reviews, vol. 7, Apr. 2007, 14 pages.
Toure, M. et al., Small-Molecule PROTACS: New Approaches to Protein Degradation, Angew. Chem. Int. Ed., 2016, vol. 55, 9 pages.
[No Author Listed], Isoplexis. Retrieved from http://isoplexis.com. Accessed June 30, 2014, 1 page.
Adams et al. "Multitarget magnetic activated cell sorter", Proc Natl Acad Sci USA. 2008, 105(47):18165-18170.
Adler et al. (2005) "Detection of femtogram amounts of biogenic amines using self-assembled DNA-protein nanostructures," Nature Methods, 2(2):147-149.
Amir et al., (2013) "viSNE enables visualization of high dimensional single-cell data and reveals phenotypic heterogeneity of leukemia", Nat Biotechnol, 31(6):545-52.
Anderson et al. (2002) "The human plasma proteome: history, character, and diagnostic prospects," Mol. Cell. Proteomics, 1 : 845-867.
Arenkov et al. (2000) "Protein microchips: use for immunoassays and enzymatic reactions," Anal. Biochem., 278:123-131.
Armstrong et al. (2000) "Suspension arrays for high throughput, multiplexed single nucleotide polymorphism genotyping," 40(2):102-108.
Ashton et al. (1973) "Smoking and carboxhemoglobin," Lancet. 2:857-858.
Balaban et al., (2004) "Bacterial persistence as a phenotypic switch", Science, 305(5690):1622-5.
BD Biosciences (2007) "Purified Mouse Anti-Human IL-2," Accessible on the Internet at URL: http://www.bdbiosciences.com/ptProduct.jsp?prodid=6725.
BD PHARMINGEN (2003) "Technical data sheet: Purified mouse anti-human IL-2 monoclonal antibody (ELISA capture)," BD Biosciences. Accessible on the Internet at URL: http://www.bdbiosciences.com/ds/pm/tds/555051.pdf.
Becker et al. (2005) "Direct readout of protein-protein interactions by mass spectrometry from protein-DNA microarrays," Angew. Chemie. Int. Ed. 44:7635-7639.
Bendall et al., (2011) "Single-cell mass cytometry of differential immune and drug responses across a human hematopoietic continuum", Science, 332(6030):687-96.
Bendall et al., (2012) "From single cells to deep phenotypes in cancer", Nat Biotechnol., 30(7):639-47.
Bernard et al. (2001) "Micromosaic immunoassays," Analytical Chemistry. 73:8-12.
Betensky et al. (2002) "Influence of unrecognized molecular heterogeneity on randomized clinical trials," J. Clin. Oncol. 20:2495-2499.
Boozer et al. (2004) "DNA directed protein immobilization on mixed ssDNA/oligo(ethylene glycol) self-assembled monolayers for sensitive biosensors," Anal. Chern. 76:6967-6972.
Boozer et al. (2006) "DNA-Directed Protein Immobilization for Simultaneous Detection of Multiple Analytes by Surface Plasmon Resonance Biosensor," Analytical Chemistry. 78:1515-1519.
Breslauer et al. (2006) "Microfluidic-based systems biology," Mol. Biosyst. 2:97-112.

(56) References Cited

OTHER PUBLICATIONS

Bunimovich et al. (2006) "Quantitative Real-Time Measurements of DNA Hybridization with Alkylated Nonoxidized Silicon Nanowires in Electrolyte Solution," J. Am. Chem. Soc. 128:16323-16331.
Chattopadhyay, P. et al. (2014) "Single-cell technologies for monitoring immune systems," Nature Immunology, 15(2):128-135.
Chen et al. (2002) "Discordant protein and mRNA expression in lung adenocarcinomas," Mol. Cell. Proteomics. 1:304-313.
Chen et al. (2004) "Plasma proteome of severe acute respiratory syndrome analyzed by two-dimensional gel electrophoresis and mass spectrometry," Proc. Natl. Acad. Sci. USA. 101:17039-17044.
Chen et al. (2005) "Marked Differences in Human Melanoma Antigen-Specific T Cell Responsiveness after Vaccination Using a Functional Microarray," PLoS Medicine, 2(10):1018-1030.
Chen et al., (2007) "Multiplexed analysis of glycan variation on native proteins captured by antibody microarrays", Nat Methods, 4(5):437-44.
Chen X. et al. (2012) "Microfluidic Devices Targeting Blood Cell Lysis", On-Chip Pretreatment of Whole Blood by Using MEMS Technology, p. 64-83.
Cheong et al. (2009) "Using a microfluidic device for high-content analysis of cell signaling", Sci Signal, 2(75), p. 12.
Choi et al., (2011) "Immuno-hybridization chain reaction for enhancing detection of individual cytokinesecreting human peripheral mononuclear cells", Anal Chem, 83(17):6890-5.
Chou et al. (2000) "Sorting biomolecules with microdevices," Electrophoresis. 21:81-90.
Coussens et al. (2002) "Inflammation and cancer," Nature. 420:860-867.
Crowley et al. (2005) "Isolation of plasma from whole blood using planar microfilters for lab-on-a-chip applications," Lab on a Chip. 5:922-929.
Dandy et al. (2007) "Array feature size influences nucleic acid surface capture in DNA microarrays," Proc Natl. Acad. Sci. USA, 104:8223-8228.
Das S. et al., (2015) "A General Synthetic Approach for Designing Epitope Targeted Macrocyclic Peptide Ligands", Angewandte Chemie, 54:13219-13224.
De Marzo et al. (2007) "Inflammation in prostate carcinogenesis," Nature Reviews Cancer. 7:256-269.
Degenaar et al. (2001) "A method for micrometer resolution patterning of primary culture neurons for SPM analysis," J. Biochem. 130:367-376.
Dehqanzada et al. (2005) "Assessing serum cytokine profiles in breast cancer patients receiving a HER2/neu vaccine using Luminex technology," Annals of Surgical Oncology, 12:S47-S48.
Delamarche et al. (1997) "Patterned delivery of immunoglobulins to surfaces using microfluidic networks," Science, 76:779-781.
Deyle, Kaycie M. et al. (2015) "Protein-targeting strategy used to develop a selective inhibitor of the E17K point mutation in the PH domain of Akt1"; Nat. Chem., 7(5), p. 455-462.
Dirks et al. (2004) "Paradigms for computational nucleic acid design," Nucleic Acids Research. 32(4):1392-1403.
Downward, J., (2003) "Targeting RAS Signalling Pathways in Cancer Therapy", Nature Reviews, vol. 3, 22 pages.
Elitas, M. et al. (2014) "A microchip platform for interrogating the single-cell level", Lab On a Chip, vol. 14(18), p. 3582.
Engvall et al. (1972) "Enzyme-linked immunosorbent assay, Elisa. 3. Quantitation of specific antibodies by enzymeabeled anti-immunoglobulin in antigen-coated tubes," J. Immunol. 109:129-135.
Erickson et al. (2003) "Modeling of DNA hybridization kinetics for spatially resolved biochips," Anal. Biochem. 317:186-200.
Eyer K. et al. (2013) "Implementing Enzyme-Linked Immunosorbent Assays on a Microfluidic Chip to Quantify Intracellular Molecules in Single Cells", Analytical Chemistry, vol. 85(6), p. 3280-3287.
Fainerman et al. (1998) "Adsorption of surfactants and proteins at fluid interfaces," Colloids and Surfaces, 143:141-165.
Fan et al., (2008) "Integrated blood barcode chips", Nat Biotechnol, 26(12):1373-8.
Fan et al., (2008) "Integrated barcode chips for rapid, multiplexed analysis of proteins in microliter quantities of blood", Nature Biotechnology, vol. 26, p. 1373-1378.
Fuji et al. (2005) "Clinical-scale high-throughput human plasma proteome analysis: lung adenocarcinoma," Droteomics. 5:1150-1159.
Fung (1973) "Stochastic flow in capillary blood vessels," Microvasc. Res. 5:34-38.
Galbraith W. et al., (1993) "Remapping disparate images for conincidence", Journal of Microscopy, vol. 172(2), p. 163-176.
Gorelik et al. (2005) "Multiplexed immunobead-based cytokine profiling for early detection of ovarian cancer," Cancer Epidemiol. Biomarkers Prev. 14:981-987.
Green et al. (2006) "Capturing the uncultivated majority", Current Opinion in Biotechnology, 17(3), p. 250-255.
Groves et al. (1995) "In vitro maturation of clonal CD4+CD8+ cell lines in response to TCR engagement," J. Immunol. 154:5011-5022.
Guan et al. (2004) "Recombinant protein-based enzyme-linked immunosorbent assay and immunochromatographic tests for detection of immunoglobulin G antibodies to severe acute respiratory syndrome (SARS) coronavirus in SARS patients," Clinical and Diagnostics Laboratory Immunology, 11(2):287-291.
Hainfeld et al. (2002) "Silver and Gold-Based Autometallography of Nanogold," Ch. 3, Gold and Silver Staining, CRC Press. Washington, DC. pp. 29-46.
Han et al., (2010) "Multidimensional analysis of the frequencies and rates of cytokine secretion from single cells by quantitative microengraving", Lab Chip, 10(11):1391-400.
Han et al., (2012) "Polyfunctional responses by human T cells result from sequential release of cytokines", Proc Natl Acad Sci USA, 109(5):1607-12.
Heath et al. (2007) "Nanotechnology and cancer," Annual Review of Medicine. 59:251-265.
Henshall et al. (2007) "Assay: Validating biomarkers with VeraCode", Genet Eng Biotechnol News, 27(17): I-3.
Holland et al. (1991) "Detection of specific polymerase chain reaction product by utilizing the 5'—3' exonuclease activity of Thermus aquaticus DNA polymerase" Proc. Natl. Acad. Sci. USA. 88:7276-7280.
Hong et al. (2003) "Integrated nanoliter systems," Nature Biotechnology, 21 :1179-1183.
Hong et al. (2004) "A nanoliter-scale nucleic acid processor with parallel architecture," Nature Biotechnology, 22 (4):435-439.
Hsieh et al. (2006) "Systematical evaluation of the effects of sample collection procedures on low-molecular-weight serum/plasma proteome profiling," Proteomics. 6:3189-3198.
Huang et al. (2001) "Detection of multiple proteins in an antibody-based protein microarray system," Journal of Immunological Methods. 255:1-13.
Huang et al. (2004) "Continuous particle separation through deterministic lateral displacement," Science, 304:987-990.
Huang et al. (2007) "Counting low-copy number proteins in a single cell," Science. 315:81-84.
Huber et al. (2004) "Comparison of proteomic and genomic analyses of the human breast cancer cell line T47D and the antiestrogen-resistant derivative T47D-r," Molec. Cell. Proteomics. 3:43-55.
Hughes et al. (2003) "Molecular Monitoring of Chronic Myeloid Leukemia," Seminars in Hematology, 40(2):62-68.
Hughes, A. et al. "Single-cell western blotting", Nat Methods, 2014, 1(7):749-55.
Iannone et al. (1999) "Multiplexed single nucleotide polymorphism genotyping by oligonucleotide ligation and flow cytometry," Cytometry. 39(2):131-140.
Ivanova et al. "Polymer Microstructures Fabricated via Laser Ablatoin Used for Multianalyte Protein Microassay", Langmuir, 2002, vol. 18, p. 9539-9546.
Jeon et al. (1991) "Protein-surface interactions in the presence of polyethylene oxide: II. Effect of protein size," Journal of Colloid and Interface Science. 142(1):159-166.
Kim et al. (1979) "Establishment and characterization of BALB/c lymphoma lines with B cell properties," J. Immunol. 122:549-554.
Kiyonaka et al. (2004) "Semi-wet peptide/protein array using supramolecular hygrogel," Nature Materials. 3:58-64.

(56) References Cited

OTHER PUBLICATIONS

Kochenderfer et al. (2012) "B-cell depletion and remissions of malignancy along with cytokine-associated toxicity in a clinical trial of anti-CD19 chimeric-antigen-receptor—transduced T cells", Blood, vol. 119(12), p. 2709-2720.
Kozlov et al. (2004) "Efficient strategies for the conjugation of oligonucleotides to antibodies enabling highly sensitive protein detection," Biopolymers. 73:621-630.
Krzywinski M. et al. (2009) "Circos: An information aesthetic for comparative genomics"; Genome Res., 19, p. 1639-1645.
Kwak, M. et al. (2013) "Single-cell protein secretomic signatures as potential correlates to tumor cell lineage evolution and cell-cell interaction", Frontiers in Oncology, 3, Art. 10, p. 1-8.
Kwon et al. (2004) "Antibody arrays prepared by cutinase-mediated immobilization on self-assembled monolayers," Anal Chem. 76:5713-5720.
Kwong et al. (2005) "Synchronous global assessment of gene and protein expression in colorectal cancer progression," Genomics. 86:142-158.
Lamb et al. (2006) "The Connectivity Map: using gene-expression signatures to connect small molecules, genes, and disease," Science. 313(5795):1929-1935.
Lambeck et al. (2007) "Serum cytokine profiling as a diagnostic and prognostic tool in ovarian cancer: a potential role or interleukin 7," Clinical Cancer Research, 13:2385-2391.
Lange et al. (2004) "Microcontact printing of DNA molecules," Analytical Chemistry. 76:1641-1647.
Lathrop (2003) "Therapeutic potential of the plasma proteome," Current Opinion in Molecular Therapeutics, 5:250-257.
Lecault et al., (2011) "High-throughput analysis of single hematopoietic stem cell proliferation in microfluidic cell culture arrays", Nat Methods, 8(7):581-586.
Lee et al. (2001) "SPR Imaging Measurements of 1-D and 2-D DNA Microarrays Created from Microfluidic Channels on Gold Thin Films," Analytical Chemistry, 73(22):5525-5531.
Lee et al., (2012) "Quantitative and dynamic assay of single cell chemotaxis", Integr Biol (Camb). 4(4):381-390.
Lin et al. (2005) "Evidence for the Presence of Disease-Perturbed Networks in Prostate Cancer Cells by Genomic and Droteomic Analyses: A Systems Approach to Disease," Cancer Res. 65:3081-3091.
Lin et al. (2007) "A cytokine-mediated link between innate immunity, inflammation, and cancer," Journal of Clinical Investigation. 117:1175-1183.
Liotta et al. (2003) "Protein microarrays: meeting analytical challenges for clinical applications", Cancer Cell, 3(4):317-325.
Liu et al. (2000) "Photopatterning of antibodies on biosensors," Bioconjugate Chem. 11:755-761.
Love et al. (2006) "A microengraving method for rapid selection of single cells producing antigenspecific antibodies", Nat Biotechnol, 24(6):703-707.
Lu, Y. et al. (2013) "High-Throughout Secretomic Analysis of Single Cells to Assess Functional Cellular Heterogeneity", vol. 85(4), p. 2548-2556.
Ma, C. et al. (2011) "A clinical microchip for evaluation of single immune cells reveals phenotypically similar T cells", Nature Medicine, vol. 17(6), p. 738-743.
MacBeath et al. (2000) "Printing proteins as microarrays for high-throughput function determination," Science, 289:1760-1763.
Madoz-Gurpide et al. (2001) "Protein based microarrays: A tool for probing the proteome of cancer cells and issues," Proteomics, 1(10):1279-1287.
Martin et al. (2006) "Molecular biology of breast cancer," Clin. Trans. Oneel. 8(1):7-14.
Mellinghoff et al. (2006) "Molecular determinants of the response of glioblastomas to EGFR kinase inhibitors," N. Engl. J. Med. 353:2012-2024.
Michel et al. (2002) "Printing meets lithography: Soft approaches to high-resolution patterning," Chimia. 56:527-542.
Michor et al. (2010) "The origins and implications of intratumor heterogeneity", Cancer Prev Res (Phila), 3(11):1361-1364.
Mischel et al. (2004) "DNA-microarray analysis of brain cancer: molecular classification for therapy," Nature Rev. Neurosci. 5:782-794.
Nagrath et al. (2007) "Isolation of rare circulating tumour cells in cancer patients by microchip technology," Nature, 450:1235-1239.
Nam et al. (2003) "Nanoparticle-based bio-bar codes for the ultrasensitive detection of proteins," Science, 301:1884-1886.
Nam et al. (2003) "Nanoparticle-based bio-bar codes for the ultrasensitive detection of proteins," Science, 301:1884-1886,—Supporting Material pp. 1 to 12.
Nathanson et al. "Co-targeting of convergent nucleotide biosynthetic pathways for leukemia eradication", J. Exp. Med., 2014, vol. 211(3), p. 473-486.
Nerowicz et al. (2002) "Multiprotein immunoassay arrays fabricated by microcontact printing," Langmuir, 18:5263-5268.
Niemeyer et al. (2005) "Immuno-PCR: high sensitivity detection of proteins by nucleic acid amplification," Trends in Biotechnology, 23:208-216.
Niemeyer (2007) "Functional devices from DNA and proteins," Nano Today, 2:42-52.
Ostrem, J.M. et al., "K-Ras(G12C) inhibitors allosterically control GTP affinity and effector interactions", Nature, 2013, vol. 503, 14 pages.
Ottesen et al. (2006) "Microfluidic digital PCR enables multigene analysis of individual environmental bacteria," Science, 314:1464-1467.
Pal et al. (2006) "Differential Phosphoprotein Mapping in Cancer Cells Using Protein Microarrays Produced from 2-D Liquid Fractionation," Anal. Chem. 78:702-710.
Park et al. (2002) "Array-Based Electrical Detection of DNA with Nanoparticle Probes," Science. 295:1503-1506.
Peluso et al. (2003) "Optimizing antibody immobilization strategies for the construction of protein arrays," Anal. Biochem. 312:113-124.
Phillips (2004) "Rapid analysis of inflammatory cytokines in cerebrospinal fluid using chip-based immunoaffinity electrophoresis," Electrophoresis. 25:1652-1659.
Pirrung (2002) "How to make a DNA chip," Angew. Chem. Int. Ed. 41:1276-1289.
Prados et al. (2003) "Temozolomide + OSI-774," Proc. Am. Soc. Clin. Oncology, 22:99.
Prime et al. (1991) "Self-assembled organic monolayers: model systems for studying adsorption of proteins at Urfaces," Science, 252:1164-1167.
Prime et al. (1993) "Adsorption of proteins onto surfaces containing end-attached oligo(ethylene oxide): a model system using self-assembled monolayers," J. Am. Chem. Soc. 115(23):10714-10721.
Quake et al. (2000) "From Micro- to Nanofabrication with Soft Materials," Science, 290:1536-1540.
Radich et al. (2006) "Gene expression changes associated with progression and response in chronic myeloid leukemia," Proc. Natl. Acad. Sci. USA. 103(8):2794-2799.
Ramsden (1995) "Puzzles and Paradox in Protein Adsorption," J. Chem. Soc. Rev. 24:73-78.
Rich et al. (2004) "Phase II trial of gefitinib in recurrent glioblastoma," J. Clin.Oncology 22:133-142.
Rowat et al., (2009) "Tracking lineages of single cells in lines using a microfluidic device", Proc Natl Acad Sci USA, 106(43):18149-54.
Sachdeva et al., (2007) "Cytokine quantitation: technologies and applications", Front Biosci. M12:4682-95, Review.
Sano et al. (1992) "Immuno-PCR: very sensitive antigen detection by means of specific antibody-DNA conjugates," Science, 258:120-122.
Sarkar A. et al. (2014) "Microfluidic probe for single-cell analysis in adherent tissue culture", Nature Communications, vol. 5.
Schena et al. (1995) "Quantitative monitoring of gene expression patterns with a complementary DNA microarray," Science, 270:467-470.
Schubert, S. et al. (2007) Hyperactive Ras in developmental disorders and cancer, Nature Reviews, vol. 7, 14 pages.

(56) References Cited

OTHER PUBLICATIONS

Schweitzer et al. (2002) "Multiplexed protein profiling on microarrays by rolling-circle amplification," Nature Biotechnology, 20:359-365.
Sedgwick H. et al. (2008) "Lab-on-a-chip technologies for proteomic analysis from isolated cells", A Journal of the Royal Society, vol. 5, No. 2, pp. S123-S130.
Shi et al., (2012) "Single-cell proteomic chip for profiling intracellular signaling pathways in single tumor cells", Proc Natl Acad Sci USA, 109(2):419-24.
Shin et al., (2010) "Chemistries for patterning robust DNA microbarcodes enable multiplex assays of cytoplasm proteins from single cancer cells", Chemphyschem., 11(14):3063-9.
Shin et al., (2011) "Protein signaling networks from single cell fluctuations and information theory profiling", Biophys J., 100(10):2378-86.
Sia et al. (2003) "Microfluidic devices fabricated in poly(dimethylsiloxane) for biological studies," Electrophoresis, 24:3563-3576.
Soen et al. (2003) "Detection and characterization of cellular immune responses using peptide-MHC microarrays," PLoS Biology, 1 (3):429-438.
Sorger, P. (2008) "Microfluidics closes in on point-of-care assays", Nature Biotechnology, vol. 26, p. 1345-1346.
Spiro et al. (2000) "A bead-based method for multiplexed identification and quantitation of DNA sequences using flow cytometry," 66(10):4258-4265.
Svanes et al. (1968) "Variations in small blood vessel hematocrits produced in hypthermic rats by micro-occlusion," Microvascular Research, 1:210-220.
Taton et al. (2000) "Scanometric DNA array detection with nanoparticle probes," Science, 289:1757-1760.
Thirumalapura et al. (2005) "Lipopolysaccharide microarrays for the detection of antibodies," Journal of Immunological Methods. 298:73-81.
Thorsen et al. (2002) "Microfluidic large-scale integration," Science. 298:580-584.
Thuillier et al. (2005) "Development of a low-cost hybrid Si/PDMS multi-layered pneumatic microvalve," Microsystem Technologies. 12(1):180-185.
Tian et al. (2004) "Integrated genomic and proteomic analyses of gene expression in mammalian cells," Mol. Cell. Proteomics. 3:960-969.
Toner et al. (2005) "Blood-on-a-chip," Annual Review of Biomedical Engineering. 7:77-103.
Toure, M. et al., (2016) "Small-Molecule PROTACS: New Approaches to Protein Degradation", Angew. Chem. Int. Ed., vol. 55, 9 pages.
Unger et al., (2000) "Monolithic microfabricated valves and pumps by multilayer soft lithography", Science, 288(5463): 113-6.
Van Duijn et al. (2002) "Detection of genetically modified organisms in foods by protein-and DNA-based techniques: bridging the methods," JAOAC Int. 85(3):787-791.
Wacker (2004) "DDI-microFIA-A readily configurable microarray-fluorescence immunoassay based on DNA-direcled immobilization of proteins," Chembiochem. 5:453-459.
Wang et al., (2010) "Single cell analysis: the new frontier in 'omics'", Trends Biotechnol., 28(6):281-90.
Wegner et al. (2003) "Fabrication of Histidine-Tagged Fusion Protein Arrays for Surface Plasmon Resonance maging Studies of Protein-Protein and Protein-DNA Interactions," Analytical Chemistry. 75:4740-4746.
Wei et al., (2013) "Microchip platforms for multiplex single-cell functional proteomics with applications to immunology and cancer research", Genome Med., 5(8):75.
Whitesides et al. (2001) "Soil lithography in biology and biochemistry," Annual Review of Biomedical Engineering, 3:335-373.
Wysocki et al. (1978) "Panning for lymphocytes: a method for cell selection," Proc. Nall. Acad. Sci. USA. 75(6):2844-2848.
Yamanaka Y. J. et al. (2012) "Single-cell analysis of the dynamics and functional outcomes of interactions between human natural killer cells and target cells" Integrative Biology, 4(10): 1175.
Yang et al. (2006) "A microfluidic device for continuous, real lime blood plasma separation," Lab on a Chip, 5:871-880.
Yang et al., (2007) "Using a cross-flow microfluidic chip and external crosslinking reaction for monodisperse TPP-chitosan microparticles", Sensors and Acuators, 124:510-516.
Yu et al. (2005) "Contextual interactions determine whether the *Drosophila homeodomain* protein, Vnd, acts as a repressor or activator," Nucleic Acids Research. 33(8):1-11.
Yu Y. et al. (2015) "Analysis of the surface, secreted, and intracellular proteome of Propionibacterium acnes", EUPA Open Proteomics, 9:1-7.
Zhang, K. et al. (2006) "Sequencing genomes from single cells by polymerase cloning", Nature Biotechnology 24(6):680-686.
Zhao et al. (2007) "High-Affinity TCRs Generated by Phage Display Provide CD4 + T Cells with the Ability to Recognize and Kill Tumor Cell Linmes", The Journal of Immunology, vol. 179: 5845-5854.
Zimmermann et al. (2005) "Modeling and optimization of high-sensitivity, low-volume microfluidic-based surface immunoassays," Biomedical Microdevices. 7(2):99-110.

\* cited by examiner

METHODS AND COMPOSITIONS FOR QUANTIFYING METABOLITES AND PROTEINS FROM SINGLE CELLS

CROSS-REFERENCE TO RELATED APPLICATION(S)

The present application claims priority to and the benefit of U.S. Provisional Application Ser. No. 62/116,246 filed on Feb. 13, 2015, and U.S. Provisional Application Ser. No. 62/265,211 filed on Dec. 9, 2015, the entire contents of both of which are incorporated herein by reference.

STATEMENT REGARDING FEDERALLY SPONSORED RESEARCH OR DEVELOPMENT

This invention was made with government support under Grant No. CA151819 awarded by the National Institutes of Health. The government has certain rights in the invention.

INCORPORATION BY REFERENCE

The instant application contains a Sequence Listing which has been submitted in ASCII format via eFS-Web and is hereby incorporated by reference in its entirety. Said ASCII copy, was created on May 3, 2016, is named 79312SEQ-LISTING.txt, and is 4,251 bytes in size.

BACKGROUND

The emergence of powerful single-cell genomic, transcriptomic, and proteomic tools over the past decade has yielded exciting approaches towards resolving the heterogeneity of complex biological systems. To date, most single cell tools have focused on transcriptome or proteome analysis, or on the sequencing of specific sets of genes. Quantitative single cell metabolic assays have proven more challenging. No reports on the integration of metabolite assays with other classes of biomolecules from the same single cells have emerged. The challenge is that different classes of biomolecules require unique assay formats that are typically not compatible. However, such integration might deliver unique information that is not readily available from traditional assays. For the case of metabolites and functional proteins, such measurements could directly resolve connections between two important classes of oncology biomarkers: the elements of the protein signaling networks that are implicated in tumor maintenance and growth, and the small molecule metabolites that provide energy sources for cell growth, or participate in metabolic signal transduction.

SUMMARY

In some embodiments of the present invention, a method of quantifying a metabolite selected from cyclic adenosine monophosphate (cAMP), cyclic guanine monophosphate (cGMP), glutathione, glucose uptake, glutamine uptake, and combinations thereof is provided. The method of quantifying these metabolites includes immobilizing a metabolite capture probe on an array chip to form a probe-bound array chip, incubating the cell with a labeled metabolite to form a cell assay mixture, incubating the cell assay mixture with the probe-bound array chip, and quantifying the amount of labeled metabolite bound to the metabolite capture probe.

In some embodiments of the present invention, a method of quantifying glucose or glutamine uptake in a cell includes immobilizing a glucose analog probe or a glutamine analog probe to the array chip, incubating the cell with a medium comprising a glucose analog or a labeled glutamine analog, removing the medium, lysing the cell to form a cell lysis, incubating the cell lysis with the probe-bound array chip; and quantifying the amount of glucose analog bound to the glucose analog probe or the amount of glutamine analog bound to the glutamine analog probe. In some embodiments the glucose analog includes glucose conjugated to biotin or adamantane. In some embodiments, the glutamine analog includes glutamine conjugated to adamantane. In some embodiments, the analog probes include streptavidin or cyclodextrin. In some embodiments, quantifying includes Forster resonance energy transfer (FRET) analysis.

In some embodiments of the present invention, the method of quantifying glucose or glutamine includes simultaneously quantifying at least one metabolite concentration in the cell, the at least one metabolite selected from cyclic adenosine monophosphate (cAMP), cyclic guanine monophosphate (cGMP), and/or glutathione. Metabolite analysis includes immobilizing at least one metabolite probe capable of binding the at least one metabolite in labeled and unlabeled forms to the array chip, then incubating the cell lysis with a calculated amount of at least one labeled metabolite, quantifying the amount of at least one bound labeled metabolite to the at least one metabolite capture probe, and finally determining the at least one metabolite concentration in the cell as the inverse of the amount of the least one bound labeled metabolite.

In some embodiments of the present invention, a metabolite assay kit is provided for quantifying a metabolite selected from adenosine monophosphate (cAMP), cyclic guanine monophosphate (cGMP), glutathione, glucose uptake and glutamine uptake, or combinations thereof. This metabolite assay kit includes a labeled metabolite selected from the group consisting of cAMP-horseradish peroxidase (cAMP-HRP), cGMP-HRP, glutathione-fluorescent dye, cAMP-fluorescent dye, cGMP-fluorescent dye, glutathione-HRP, glucose-biotin, glutamine-adamantane, glucose-adamantane, and combinations thereof. The metabolite assay kit also includes a metabolite capture probe comprising at least one of anti-cAMP antibody, anti-cGMP antibody, anti-glutathione antibody, streptavidin, cyclodextrin, or combinations thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 6B-6E are schematics depicting the supramolecular glutamine uptake assay according to embodiments of the present invention, in which FIG. 5B shows Cyclodextrin-Cy3 immobilized on a chip providing maximum green fluorescence with binding of adamantane-BHQ2 (Ad-BHQ2) resulting in quenching and minimized green fluorescence; FIG. 5C is a graph measuring the fluorescence of unbound Cyclodextrin-Cy3 (No Quencher) and Cyclodextrin-Cy3 bound by Adamantane-BHQ2; FIG. 5D shows an on-chip FRET competition assay of the Adamantane Glutamine analog and the Admantane-BHQ2; FIG. 5E is a graph showing the amount of Cyclodextrin-Cy3 fluorescence as a function of 0, 10, and 100 μM of Adamantane-Glutamine analog.

DETAILED DESCRIPTION

Aspects of embodiments of the present invention provide methods and compositions for microchip-based simultaneous quantification of metabolites and proteins in single cells.

Figure 1A:
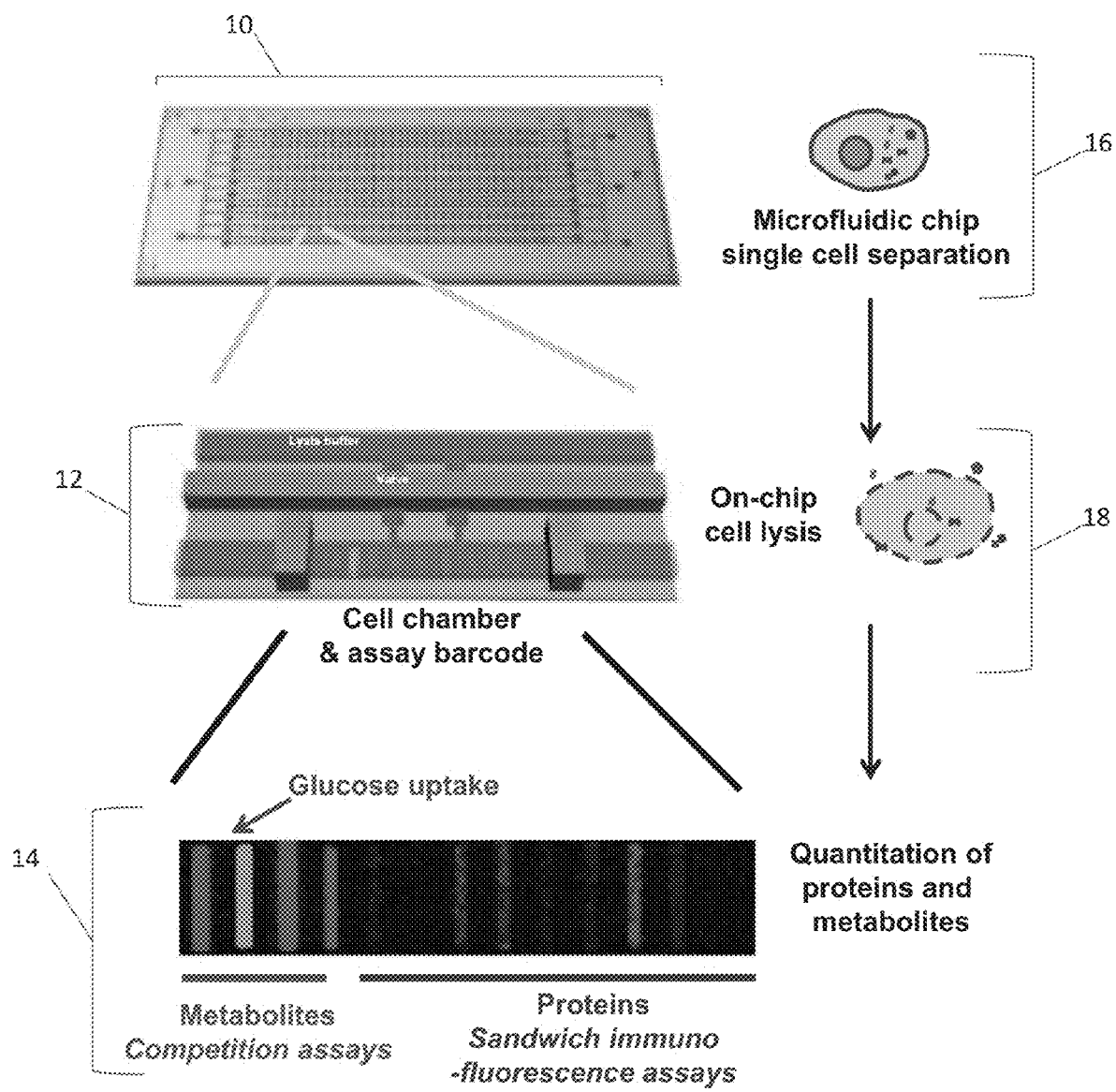
FIG. 1A is an illustration of a single cell barcode chip (SCBC) layout (10) with a zoomed in view of the individual miniaturized cell chambers (12) of the SCBC, and a representative red and/or green fluorescence image of one barcode set (14), with a parallel schematic of a single cell with labeled metabolites and proteins (16) and on-chip cell lysis (18), according to embodiments of the present invention.
Figure 1B:
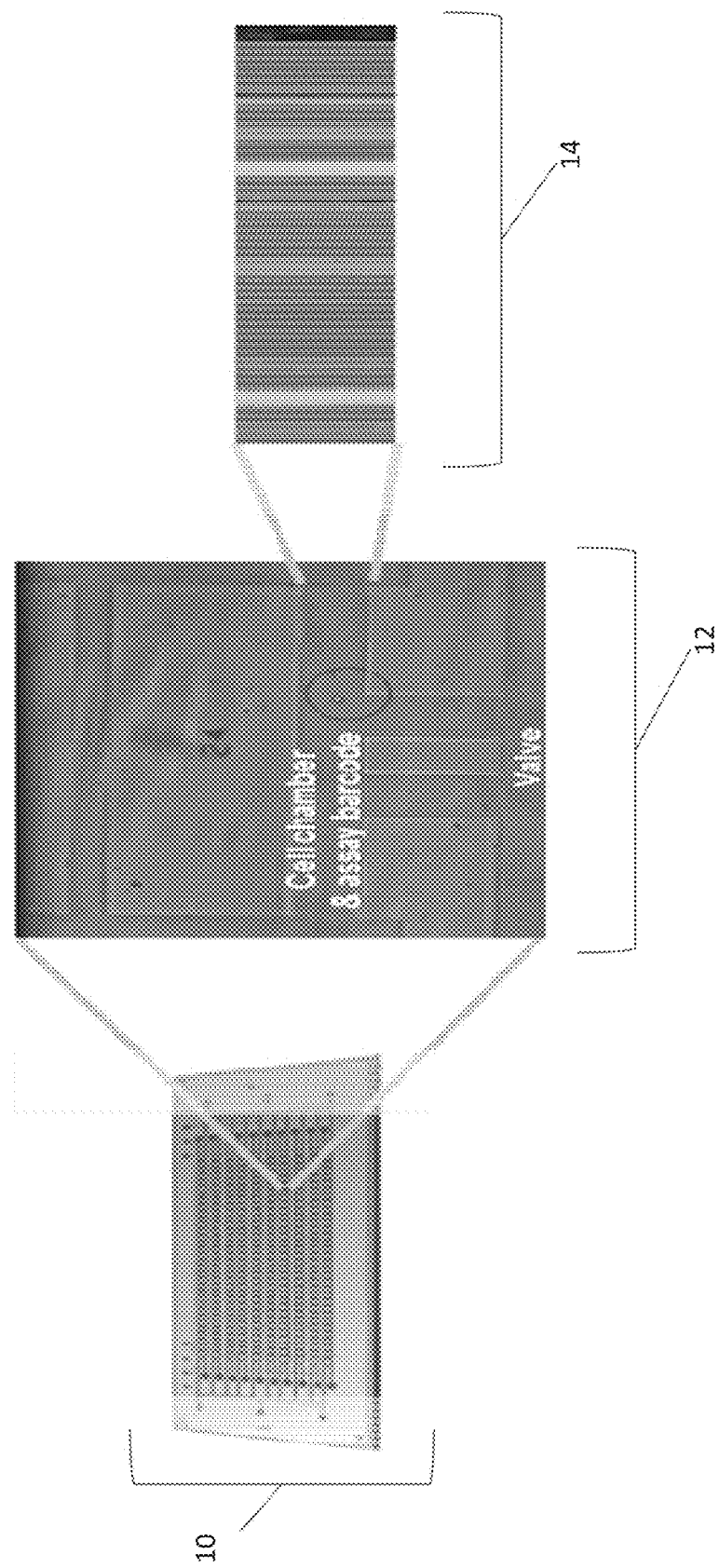
FIG. 1B is an illustration of a SCBC layout (10) with a photo image of the single cell chamber (12), and a corresponding red and/or green fluorescent barcode result (14), according to embodiments of the present invention.
Figure 2A:
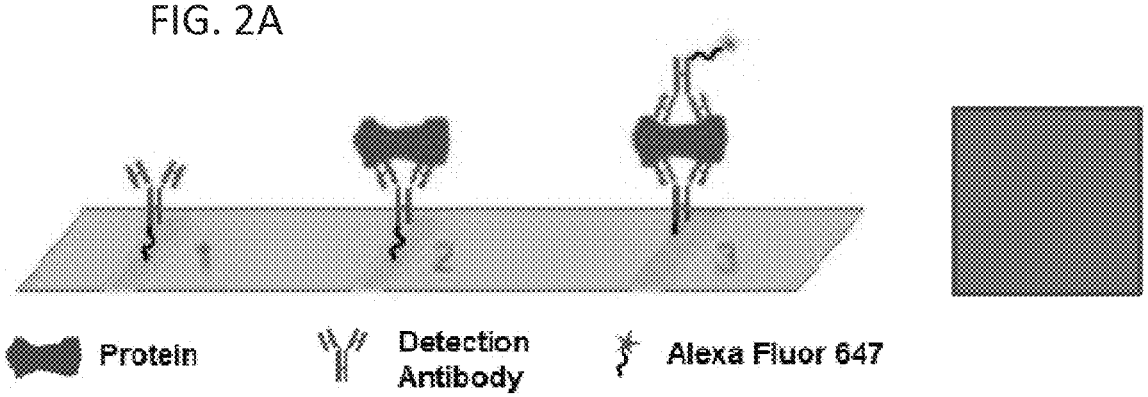
FIG. 2A is a schematic showing immunofluorescence assays on a chip, according to embodiments of the present invention, for assaying proteins (purple), with protein detection assayed using sandwich immunofluorescence in which the blue capture antibody is conjugated to ssDNA for immobilization on the chip, and Alexa Fluor 647 (A647) red dye is conjugated to the detection antibody.
Figure 2B:
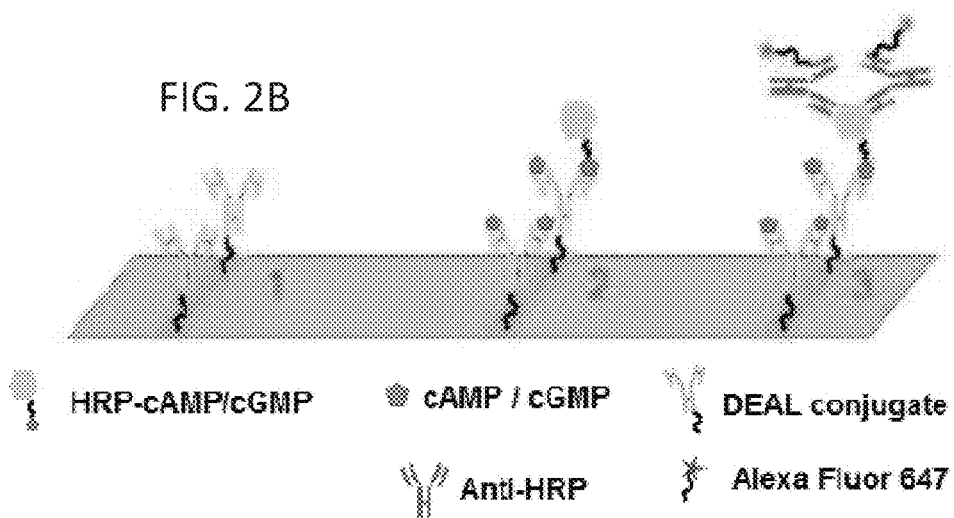
FIG. 2B is a schematic showing immunofluorescence assays on a chip, according to embodiments of the present invention, for assaying cyclic adenosine monophosphate (cAMP) and cyclic guanine monophosphate (cGMP) (blue), as well as horseradish peroxidase (HRP) (grey) conjugates of cAMP and cGMP (cAMP-HRP and cGMP-HRP) are captured on the chip by a DNA encoded antibody library (DEAL) conjugate antibody (yellow) that binds to the chip and recognize cAMP and cAMP-HRP or cGMP and cGMP-HRP, with the cAMP-HRP and cGMP-HRP conjugates detected by the red AF647-labeled HRP antibodies.
Figure 2C:
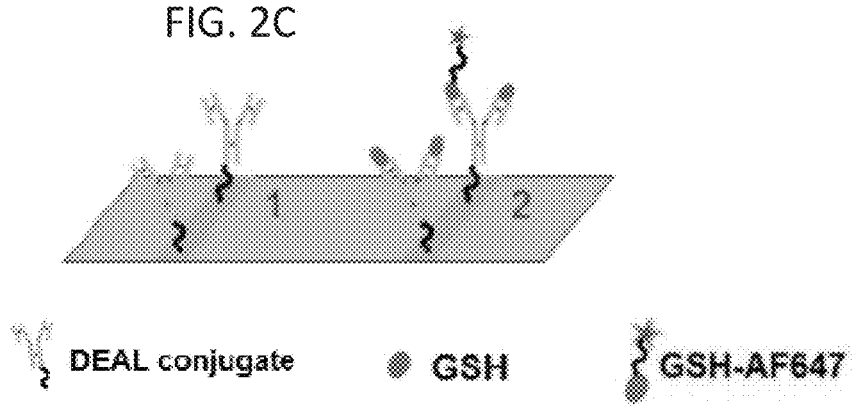
FIG. 2C is a schematic showing immunofluorescence assays on a chip, according to embodiments of the present invention, for assaying and glutathione (GSH) (green) and GSH-A647 (red star) conjugates captured by a DEAL conjugate antibody (yellow) that recognizes both GSH and GSH-A647.
Figure 2D:
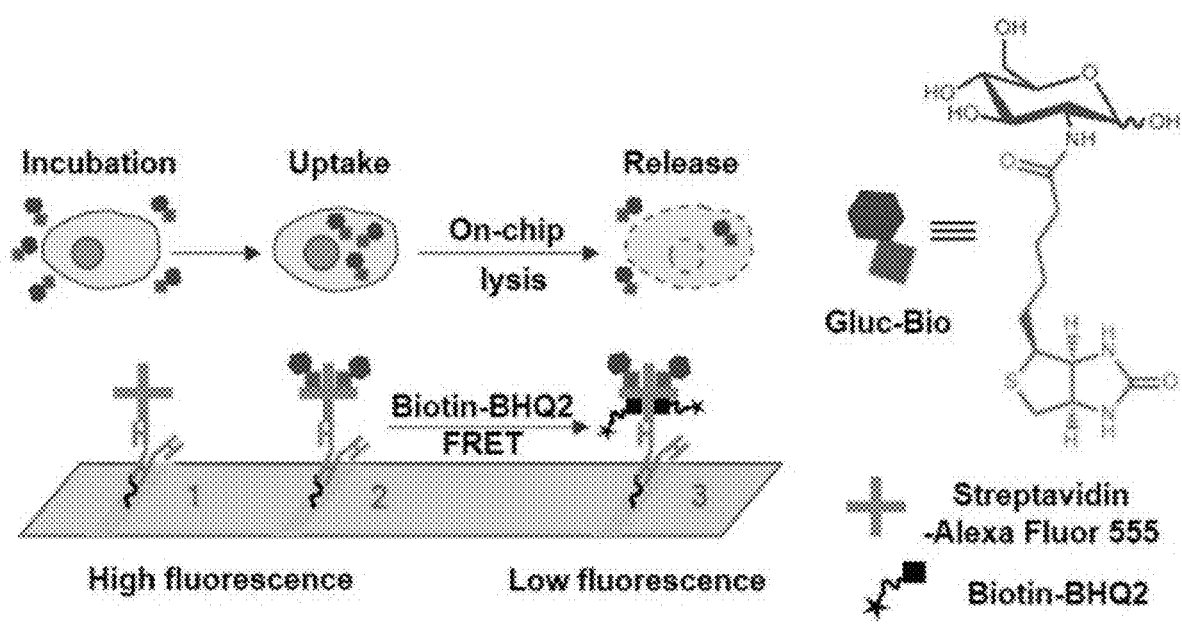
FIG. 2D is a schematic showing immunofluorescence on a chip, according to embodiments of the present invention, for assaying glucose uptake in a cell using a glucose-biotin (Gluc-Bio) conjugate (blue hexagon-red square) in which the Gluc-Bio conjugate is incubated with a cell followed by on-chip cell lysis and quantification of Gluc-Bio conjugate in the cell using FRET (Förster resonance energy transfer) analysis in which the Gluc-Bio is captured by Streptavidin-Alexa Fluor 555 (Strep-AF555) immobilized on the chip with a ssDNA-anti-Streptavidin antibody (orange), where the binding of Gluc-Bio to the Strep-AF555 results in a high fluorescence, and unoccupied Strep-AF555 is occupied by Biotin-BHQ2 thereby quenching the fluorescence.
Figure 2E:
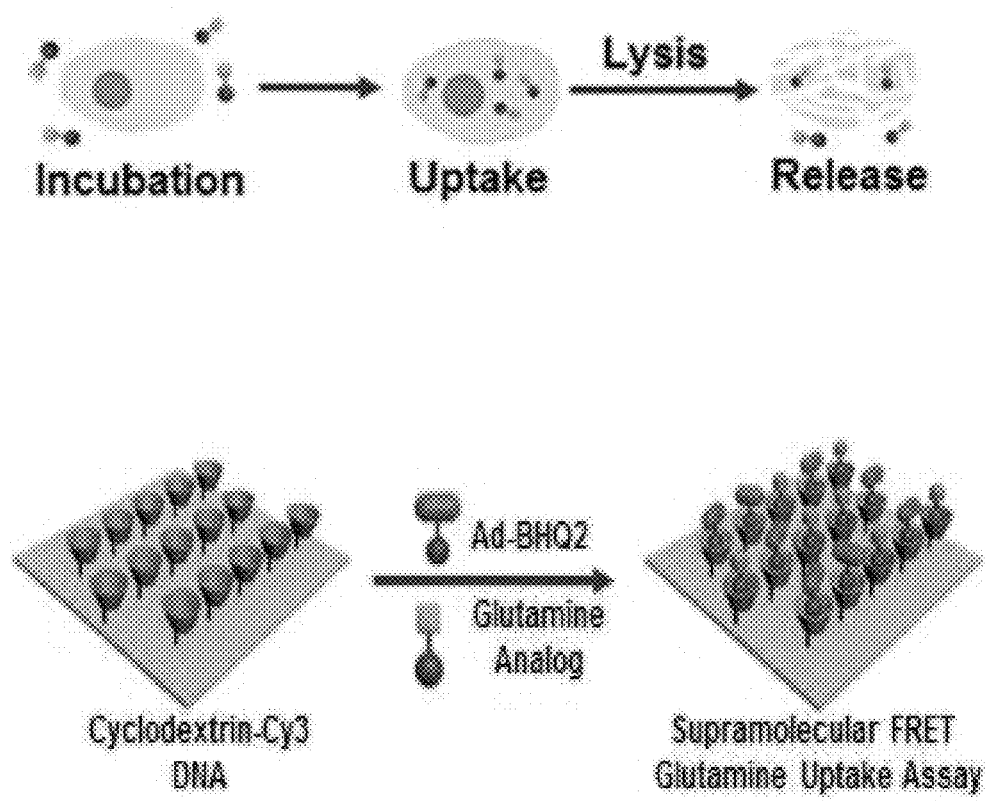
FIG. 2E is a schematic showing immunofluorescence on a chip, according to embodiments of the present invention, for assaying glutamine uptake in a cell using an adamantane-labeled glutamine analog (Glutamine Analog) in which the glutamine analog is incubated with a cell (Incubation) to allow for Uptake into the cell, followed by on-chip Lysis and quantification of the glutamine analog in the cell using FRET analysis in which the adamantane glutamine analog is captured by immobilized Cyclodextrin-Cyanine 3 DNA (Cyclodextrin-Cy3 DNA) giving high fluorescence, and unoccupied Cyclodextrin-Cy3 DNA is occupied by Adamantane-BHQ2 (Ad-BHQ2) thereby quenching the fluorescence.

Quantitative measurements (generating copy numbers per cell) of intracellular proteins may be accomplished using calibrated, sandwich-type immunofluorescence assays as depicted in FIG. 2A. Such assays require a surface-bound capture antibody and a fluorophore-labeled detection antibody, and yield an optical readout that correlates with protein copy number. These assays may be miniaturized and multiplexed through spatial addressing using the single cell barcode chip (SCBC) format as shown in FIGS. 1A and 1B. However, metabolites are small molecules, and cannot be similarly detected by antibody pairs in a sandwich-type assay. According to embodiments of the present invention, four types of spatially-addressable competition assays are provided that measure the absolute or relative levels of 5 small molecule metabolites, including cyclic adenosine monophosphate (cAMP) and cyclic guanine monophosphate (GMP) (FIG. 2B), glutathione (FIG. 2C), glucose (FIG. 2D), and glutamine (FIG. 2E).

The metabolite immunofluorescent assays according to embodiments of the present invention may be incorporated into a multiplex protein platform assay allowing for the simultaneous quantification of metabolites and proteins in a single cell, and thereby providing a more complete metabolic analysis of the interrogated cell. For example, the effects of potential cancer cell inhibitors on regulatory proteins as well as metabolites may be analyzed concurrently in cancer cells to elucidate cellular interactions and improve cancer therapies.

As used herein, the term "conjugate," and like terms refers to a molecule made of at least two components that are joined together to form a larger biomolecule. For example, a conjugate may include the fusion of two proteins or the fusion of a small molecule with a protein or peptide. DNA conjugates include DNA-linked molecules including small biomolecules (e.g., metabolites) peptides, proteins, antibodies, and dyes. Dye conjugates include the fusion of a dye with any molecule, including peptides, proteins, antibodies, and small molecules. As used herein, a metabolite conjugate is a metabolite fused to a protein or molecule. A "metabolite conjugate" is used interchangeably with "labeled metabolite."

As used herein a "metabolite capture probe," "capture probe," and like terms refer to a molecule or protein that is capable of binding the metabolite, metabolite conjugate, and/or a labeled metabolite, as disclosed herein.

As used herein, the terms "chip," "array chip," "chip platform," and like terms refer to a solid substrate upon which capture probes are immobilized. As disclosed herein, chip platforms may be made of any suitable materials. For example, chips may be made of polydimethylsiloxane (PDMS), glass, and/or thermoplastics including polymethyl methacrylate (PMMA), polycarbonate (PC), polystyrene (PS), cyclic olefin copolymer (COC), and/or cyclic olefin polymer (COP). Some chip platforms may have more than one layer. For example, the single cell barcode chip (SCBC) is an example of a chip platform. SCBC as disclosed herein in detail is a two-layer PDMS chip and a DNA barcode glass slide.

As used herein the terms "immobilized," "immobilizing," and like terms refer to the conjugation or coupling of a biomolecule (e.g., DNA, protein, small molecule) to a substrate, e.g., to a chip.

As used herein, the term "DNA-immobilized" and like terms refer to the coupling of a capture probe onto a chip by DNA hybridization. The chip is bound by single stranded DNA (ssDNA) that is complementary to an ssDNA moiety conjugated to the capture probe resulting in immobilization of the capture probe onto the chip by the hybridization of the complementary ssDNA molecules. For example, DNA-immobilization of antibodies may be carried out using DNA encoded antibody libraries (DEAL) as described in Bailey et al., 2007, *JACS*, 129:1959-1967, the entire contents of which are herein incorporated by reference.

In some embodiments of the present invention, methods and compositions are provided for quantifying metabolites in a cell. These methods and compositions allow for the analysis of cAMP, cGMP, glutathione, glucose uptake, and glutamine uptake in a single cell. The assay methods and metabolite conjugates disclosed may be used for single metabolite detection, or may be used in combination. The disclosed metabolite assays may be easily incorporated with established protein assays thereby allowing for simultaneous quantification of these metabolites and proteins in a single cell.

In some embodiments of the present invention, a method of quantifying a metabolite selected from (cAMP), (cGMP), glutathione, glucose uptake, glutamine uptake, and combinations thereof is provided. The method of quantifying these metabolites includes immobilizing a metabolite capture probe on an array chip to form a probe-bound array chip, incubating the cell with a labeled metabolite to form a cell assay mixture, incubating the cell assay mixture with the probe-bound array chip, and quantifying the amount of labeled metabolite bound to the metabolite capture probe.

In some embodiments of the present invention a kit is provided including the metabolite conjugates and capture probes for quantifying metabolites in a single cell fluorescent assay.

cAMP/cGMP

In some embodiments of the present invention, a method for quantifying the concentration of cyclic adenosine monophosphate (cAMP) and cyclic guanine monophosphate (cGMP) in a cell include using known amounts of labeled cAMP and cGMP and commercially available capture antibodies to cAMP and cGMP. In some embodiments of the present invention, labeled cAMP and cGMP conjugates are mixed with a lysed cell suspension on a chip platform, allowing the labeled cAMP and cGMP conjugates to compete with the unlabeled cellular cAMP and cGMP for the antibody binding sites on the chip. As depicted in FIG. 2B, anti-cAMP and anti-cGMP antibodies may be immobilized onto a chip platform using DNA encoded antibody library (DEAL) methods as further disclosed herein. The immobilization of the capture antibodies is not limited to a DEAL method and may be carried out using any suitable method for conjugating the antibody to a selected chip platform. The cAMP and cGMP labeled conjugates are synthesized such that the label does not disrupt the cAMP or cGMP antibody binding. As such, both the unlabeled cellular cAMP/cGMP and the labeled cAMP/cGMP are able to bind to the capture antibodies, however, only the labeled cAMP/cGMP produces fluorescence using a fluorescently tagged detection antibody that recognizes the label. Fluorescence intensities are quantified using laser scanning techniques as disclosed herein.

Figure 7A:
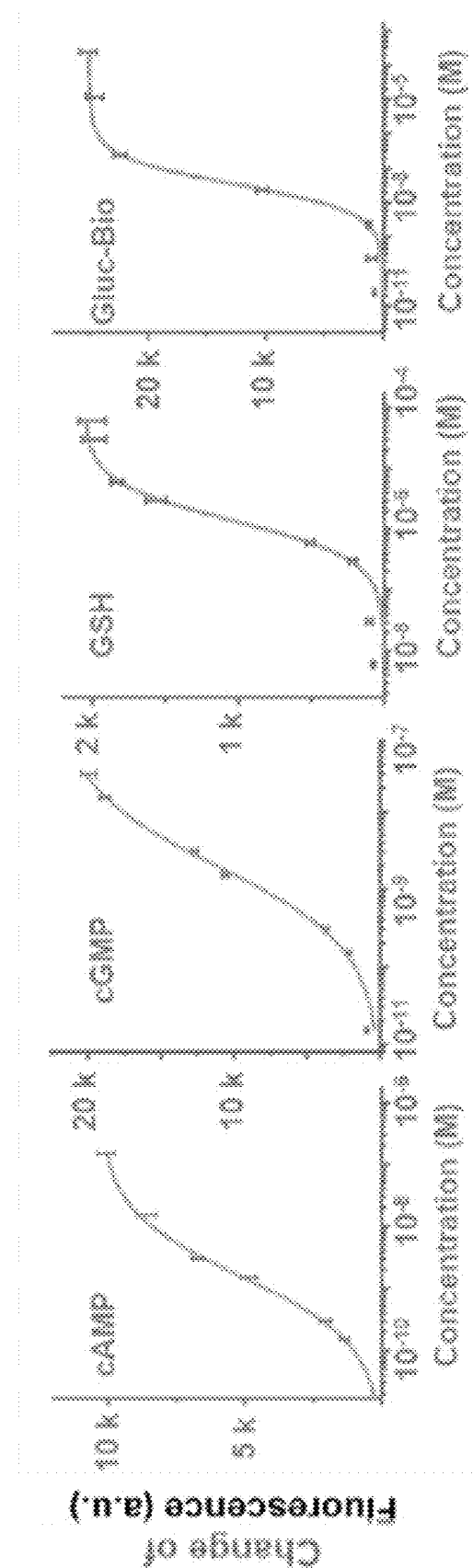
FIG. 7A shows calibration curves measuring the change of fluorescence as function of molarity concentration (M) for each of cAMP, cGMP, GSH, and Gluc-Bio using the corresponding immunofluorescence assays shown in FIGS. 2A and 2B, according to embodiments of the present invention.

As shown in FIG. 2B, cAMP and cGMP may be labeled with horseradish peroxidase (HRP). Using an anti-HRP antibody conjugated to a fluorescent dye (e.g., Alex Fluor 647), the fluorescence intensities recorded from the respective cAMP and cGMP positions on the chip platform may be quantified. The amount of fluorescence from the labeled cAMP and cGMP inversely correlates with the intracellular concentrations of the cAMP and cGMP. FIG. 7A shows calibration curves of fluorescence intensity as a function of increasing amounts (concentration (M)) of the cAMP-HRP and cGMP-HRP conjugates.

In some embodiments of the present invention, cAMP and cGMP are conjugated to horseradish peroxidase (HRP). In some embodiments of the present invention, cAMP and cGMP are conjugated to any suitable fluorescent dye as disclosed, for example, in Molecular Probes Handbook, *A Guide to Fluorescent Probes and Labeling Technologies*, 11th Ed. 2010, I. Johnson and M. T. Z Spence, the entire contents of which is herein incorporated by reference. Non-limiting examples of suitable fluorescent dyes include the Alexa Fluor® dyes (Thermo Fisher).

Glutathione (GSH)

Figure 3A:
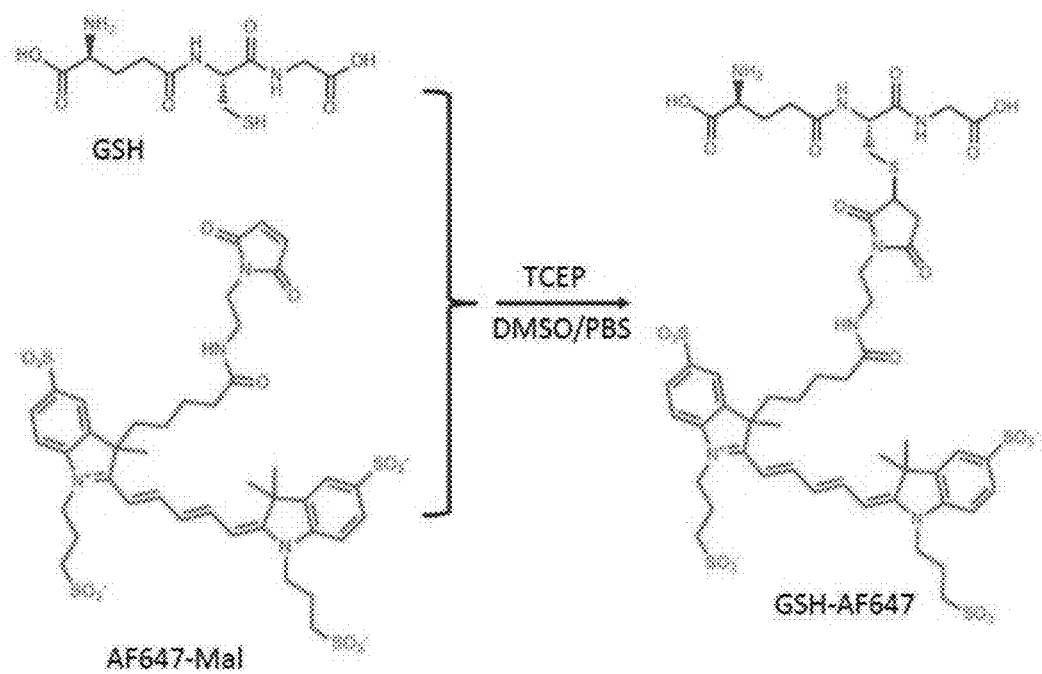
FIG. 3A is a synthetic scheme of a glutathione (GSH) (green) conjugation reaction to Alexa-Fluor 647 maleimide (AF647-Mal) (red) in the presence of (tris(2-carboxyethyl) phosphine) (TCEP), DMSO, and PBS to form GSH-AF647, according to embodiments of the present invention.
Figure 3B:
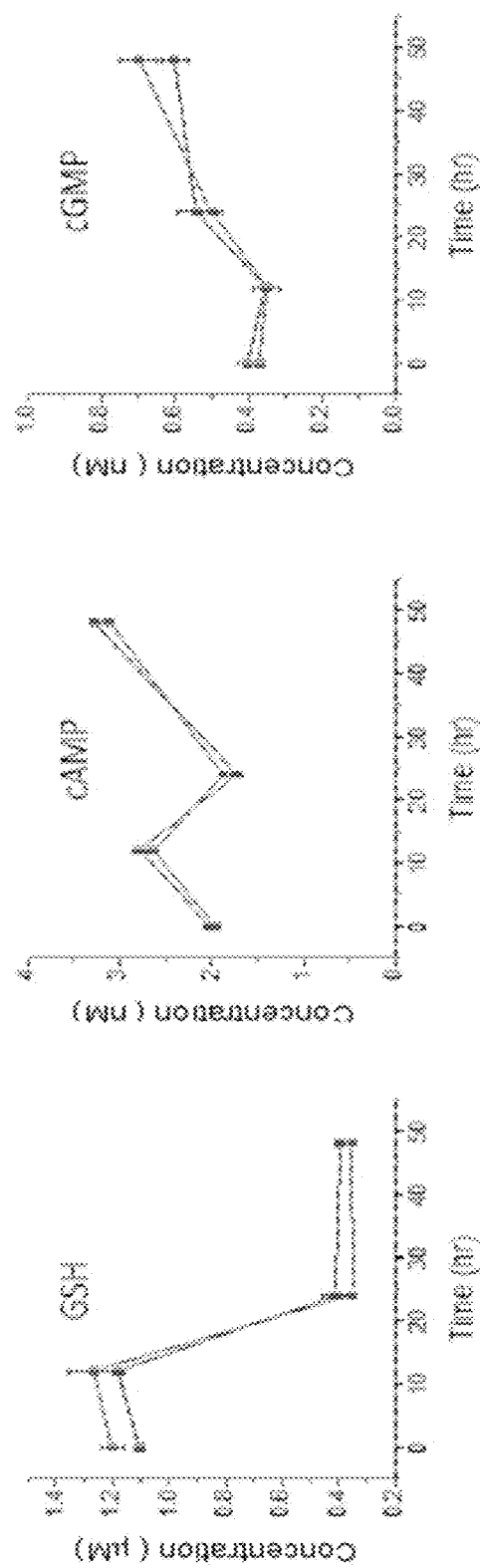
FIG. 3B shows graphs measuring metabolite concentrations in GBM39 primary neurosphere cells for each of GSH, cAMP, and cGMP as indicated, in which each graph compares concentrations of the indicated metabolite as measured using the immunofluorescence assays as shown in FIG. 2A (red traces) with concentrations of these metabolites as measured using commercially available assay kits (blue traces); Glutathione Assay Kit, Cayman Chemical #703002; Cyclic AMP XP Assay Kit, Cell Signaling #4339; and Cyclic GMP XP Assay Kit, Cell Signaling #4360, according to embodiments of the present invention.

The metabolite glutathione (GSH) participates in cellular redox stress. In some embodiments of the present invention, a method of quantifying the cellular concentration of GSH includes using known amounts of labeled GSH and a commercially available capture antibody to GSH. In some embodiments of the present invention, labeled GSH is mixed with a lysed cell suspension on a chip platform, allowing the labeled GSH conjugate to compete with the unlabeled cellular GSH for the antibody binding sites on the chip. As depicted in FIG. 2C, anti-GSH antibodies are immobilized onto the chip platform using DNA encoded antibody library (DEAL) methods as further disclosed herein. The immobilization of the capture antibodies is not limited to a DEAL method and may be carried out using any suitable method for conjugating the antibody to a selected chip platform. The GSH labeled conjugate is synthesized such that the label does not disrupt the GSH antibody binding as shown in FIG. 3A. As such, both the unlabeled cellular GSH and the labeled GSH are able to bind to the anti-GSH capture antibody, however, only the labeled GSH produces fluorescence. Fluorescence intensities are quantified using laser scanning techniques as disclosed herein.

As shown in FIG. 2C, GSH is labeled with Alexa Fluor dye 647 (AF647) to produce the GSH-AF647 conjugate. The fluorescence intensity recorded from the GSH-AF647 position on the chip platform is quantified. The amount of fluorescence from the labeled GSH inversely correlates with the intracellular concentrations of GSH. In some embodiments of the present invention, GSH is conjugated to any suitable fluorescent dye. Non-limiting examples of a fluorescent dye include any Alexa Fluor® dye, e.g., AF647. FIG. 7A shows a calibration curve of fluorescence intensity as a function of increasing amounts (concentration (M)) of the GSH-AF647 conjugate.

In some embodiments, GSH is conjugated to horseradish peroxidase (HRP), as described above for cAMP/cGMP. In some embodiments, a GSH-HRP conjugate is quantified using a fluorescently labeled anti-HRP antibody as shown for cAMP/cGMP in FIG. 2B.

Glucose Uptake

In some embodiments of the present invention, a method for measuring glucose uptake in a cell includes incubating the cell with a glucose analog, followed by lysis of the cell, and quantification of the amount of the glucose analog in the cell. As shown in FIG. 2D, glucose is conjugated to biotin forming the Gluc-Bio glucose analog. The Gluc-Bio analog is incubated with the cell or cells, followed by a wash to remove any Gluc-Bio remaining in the cell medium. Following cell lysis, Gluc-Bio that was taken up intracellularly is released and binds to immobilized dye-labeled (e.g., Alexa Fluor 555 (AF555)) streptavidin (depicted as a green cross in FIG. 2D) on the chip platform. Subsequently, the unoccupied binding sites on the streptavidin are filled using a Biotin-BHQ2 conjugate which quenches the fluorescence of AF555 through a FRET process. Using this method, the fluorescence intensity readout from the labeled-streptavidin positively correlates to the amount of Gluc-Bio that is taken up by the cell and released upon lysis. Fluorescence intensities are quantified using laser scanning techniques as disclosed herein.

Figure 4A:
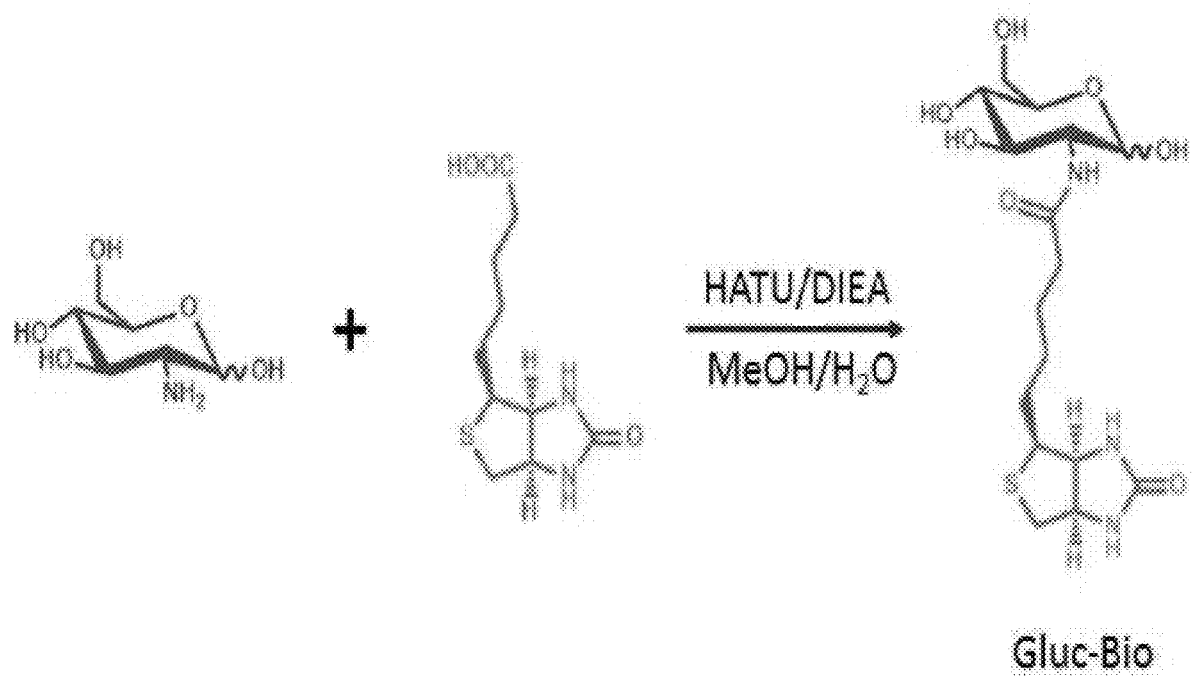
FIG. 4A is a synthetic scheme of a glucosamine (blue) conjugation reaction to biotin (red) in the presence of HATU/DIEA, methanol, and water to form a Gluc-Bio conjugate, according to embodiments of the present invention.
Figure 4B:
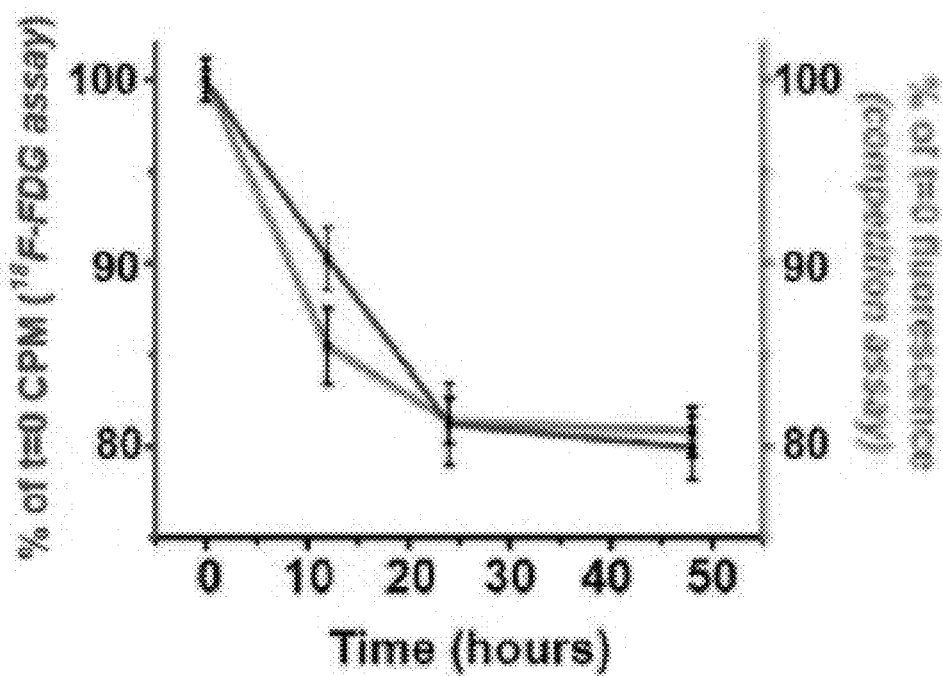
FIG. 4B is a graph showing parallel measurements of $^{18}$F-FDG and Gluc-Bio uptake in cells to demonstrate the validity of Gluc-Bio as a glucose uptake probe, where the amount of $^{18}$F-FDG is a known radioactive labeled glucose analog in which the counts per minute (cpm) over time correspond to increased uptake into the cell and Gluc-Bio uptake is measured as percent (%) fluorescence over time, according to embodiments of the present invention.
Figure 4C:
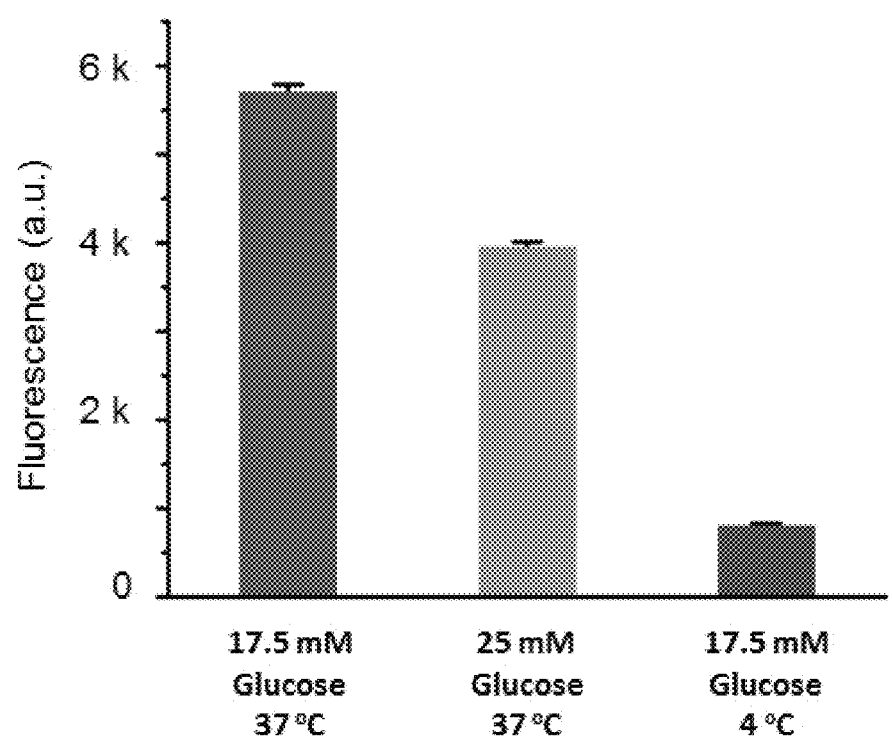
FIG. 4C is a graph of cell uptake experiments using the immunofluorescence assay depicted in FIG. 2B to assay Gluc-Bio uptake in GBM39 primary neurosphere cells at 37° C. in the presence of 17.5 mm glucose and 25 mM glucose, and at 4° C. at 17.5 mM glucose as indicated, showing that Gluc-Bio competes with glucose, according to embodiments of the present invention.
Figure 4D:
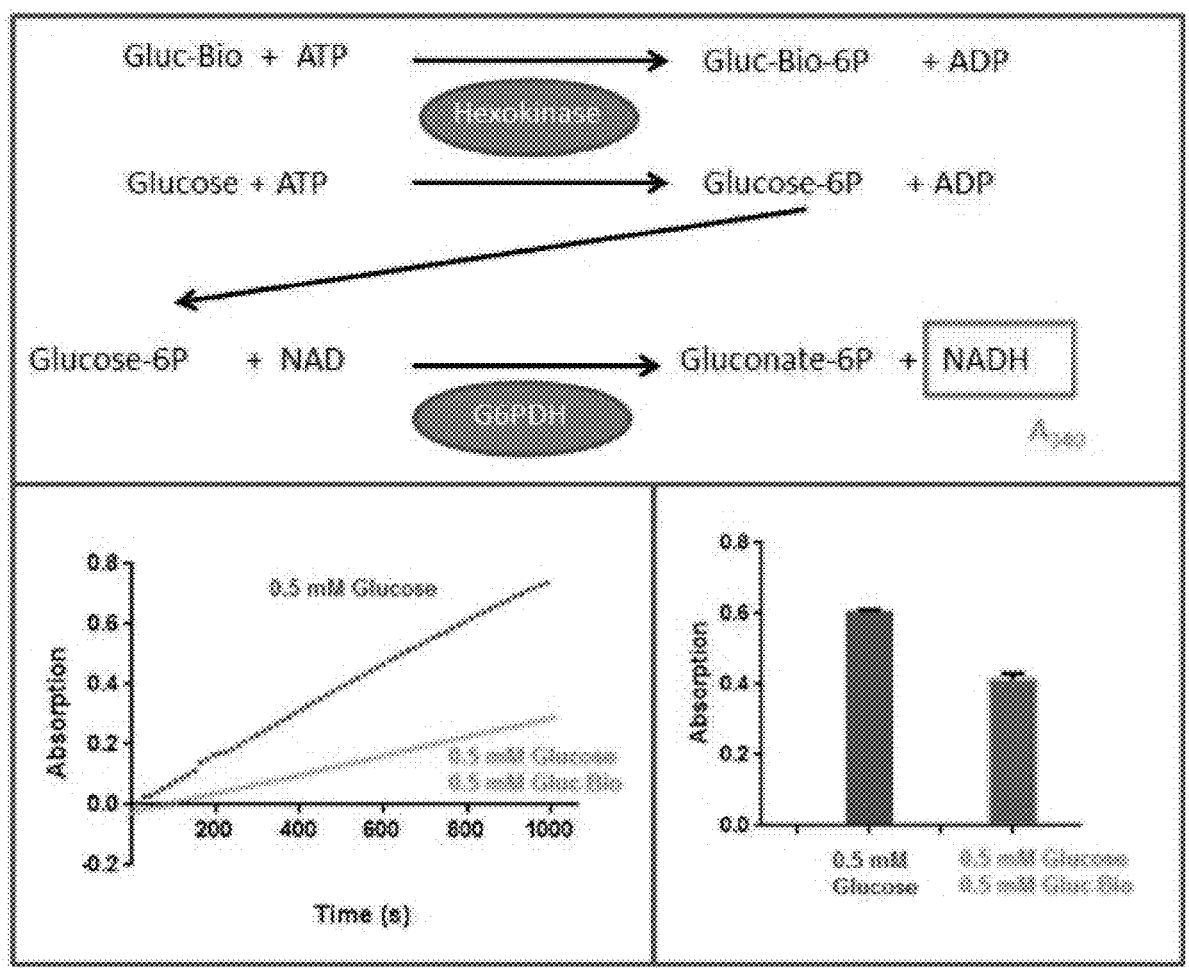
FIG. 4D shows a schematic of the coupled enzyme reactions that allow for the assaying of hexokinase by measuring the absorption of NADH (upper panel) in which Gluc-Bio inhibits the reaction of NADH as it competes with the reactants but cannot catalyze NADH; the lower left and panel shows a graph of absorbance data for NADH in which 0.5 mM glucose alone is the upper line and 0.5 mM glucose and 0.5 mM Gluc-Bio is the lower line showing less absorbance over time; and the lower right graph represents the final amounts of NADH produced from 0.5 glucose or 0.5 mM glucose and 0.5 mM Gluc-Bio, as indicated, according to embodiments of the present invention.

In some embodiments, the Gluc-Bio analog is synthesized using any suitable method. In some embodiments, Gluc-Bio is conjugated as shown in FIG. 4A. The Gluc-Bio of FIG. 4A was validated as a probe for glucose uptake in comparative uptake assays with the previously characterized glucose analog $^{18}$F-FDG ($^{18}$F-(fludeoxyglucose)) as shown in FIG. 4B. Further evidence that Gluc-Bio is actively taken up by cells is shown in FIG. 4C in which the uptake of the Gluc-Bio analog is inhibited by increasing the extracellular glucose concentration and by decreasing the temperature. The Gluc-Bio analog was also shown to be a substrate for hexokinase (HK) as shown in FIG. 4D. FIG. 7A shows a calibration curve of fluorescence intensity as a function of increasing amounts (concentration (M)) of the Gluc-Bio conjugate.

In some embodiments of the present invention, the glucose analog for measuring glucose uptake in a cell may be glucose conjugated to biotin forming Gluc-Bio as discussed above and shown in FIG. 4A. The Gluc-Bio analog may be captured using any immobilized streptavidin. As shown in FIG. 2D, a dye-labeled streptavidin capture probe is immobilized with an anti-streptavidin antibody linked using DNA-immobilization methods as disclosed herein.

In some embodiments, glucose may be conjugated to adamantane to form an adamantane-labeled glucose conjugate which may be captured on a chip platform using immobilized fluorescently labeled cyclodextrin and assayed using a FRET assay as disclosed herein for adamantane-labeled glutamine.

Glutamine Uptake

Upregulated glutamine metabolism (termed glutamine addiction) has recently been recognized as another unique feature of many tumors (Wise et al., 2010, *Trends. Biochem. Sci.* 35:427-433, the entire contents of which are herein incorporated by reference). In those cases, glutamine participates in the TCA cycle through conversion to α-ketoglutarate, and provides an alternative energy source to glucose. Certain cases of drug resistance in cancer are accompanied by glutamine addiction. Disease or drug-induced alterations of metabolic processes highlight that those processes may be considered as signaling networks comprised of interacting proteins and metabolites.

Figure 5A:
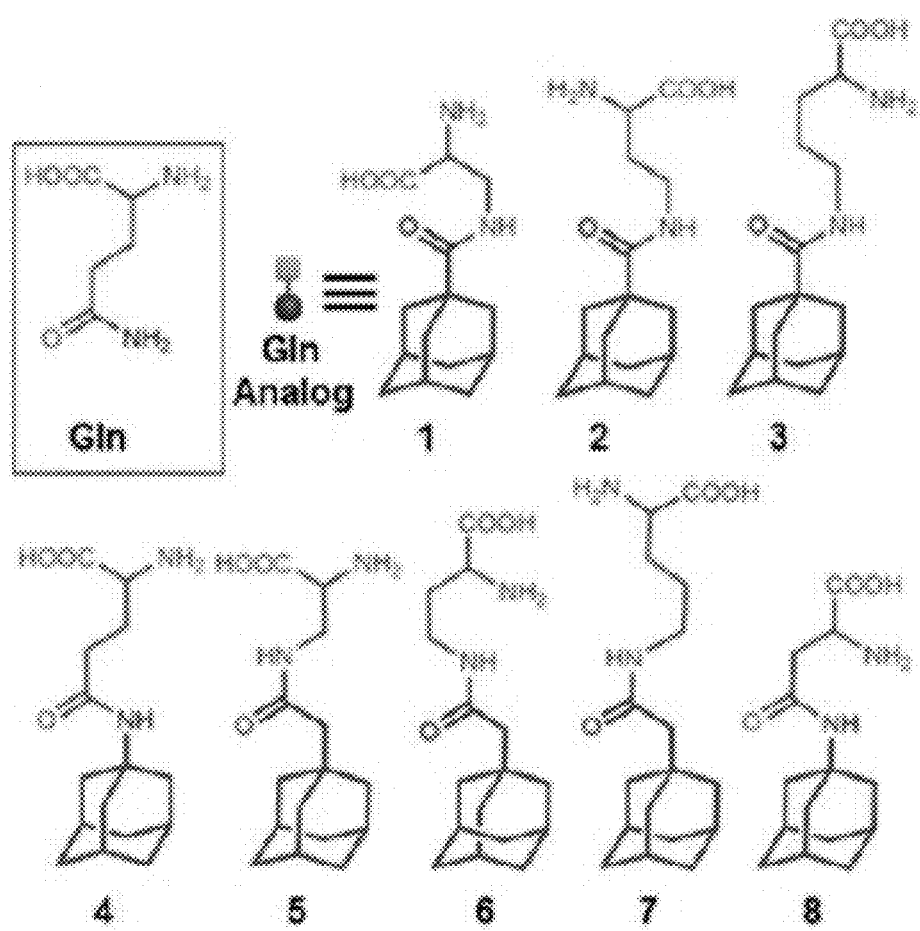
FIG. 5A shows the glutamine (Gln) structure and eight adamantane-labeled amino acid conjugates (Compounds 1-8), according to embodiments of the present invention.
Figure 5B:
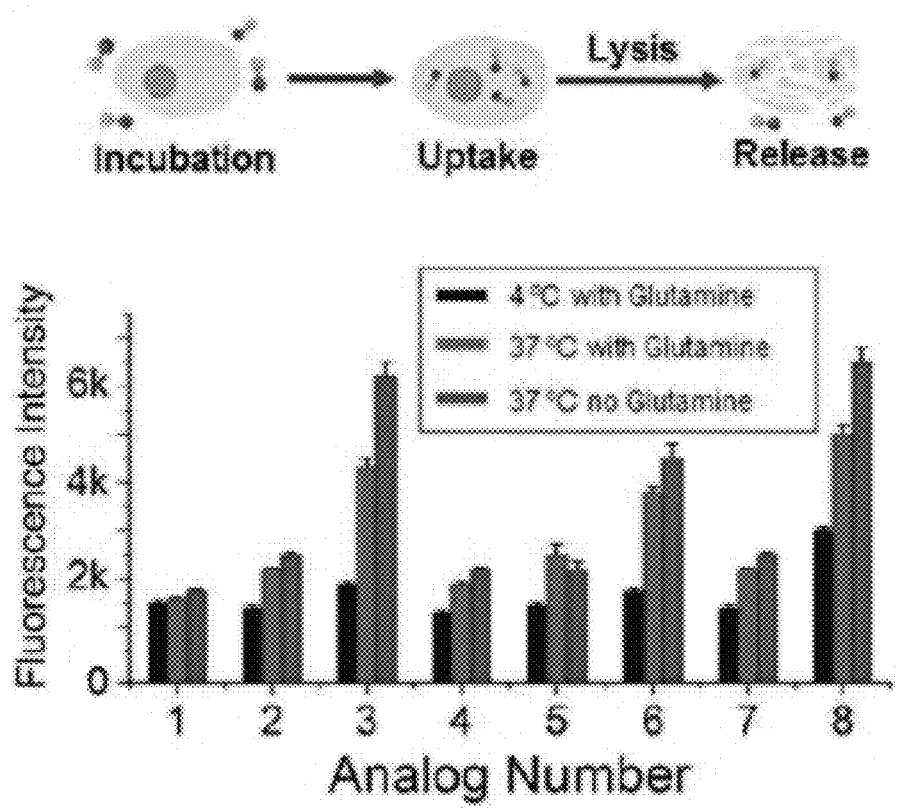
FIG. 5B is a graph of cell uptake experiments using the immunofluorescence assay depicted in FIG. 2C to assay Compounds 1-8 as shown in FIG. 5A in the presence of glutamine at 4° C. (left bars) and 37° C. (middle bars), and in the absence of glutamine at 37° C. (right bars), according to embodiments of the present invention.
Figure 5C:
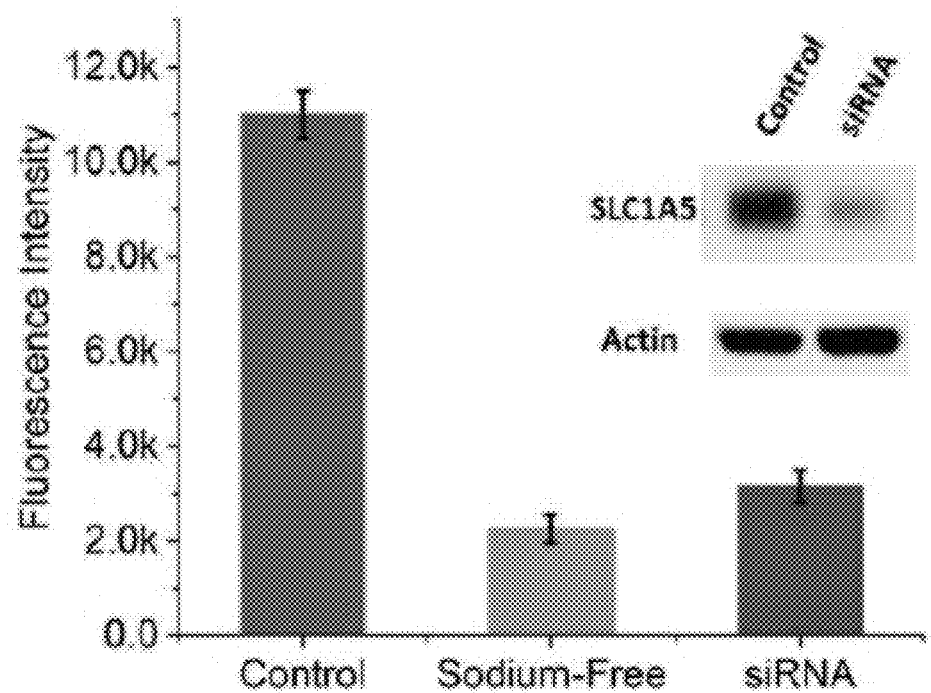
FIG. 5C shows fluorescence intensity of an uptake assay in U87 cells using Compound 3 Ad-Glutamine analog as shown in FIG. 5B in which control conditions show fluorescence indicative of uptake; in which the sodium-dependent SLC1A5 neutral amino acid transporter is inhibited under sodium free conditions resulting in inhibition of Compound 3 fluorescence (uptake) and inhibition of Compound 3 fluorescence by SLC1A5 siRNA; showing that Compound 3 Ad-Glutamine analog is dependent upon the SLC1A5 transporter for cell uptake and is a substitute for glutamine, according to embodiments of the present invention.
Figure 5D:
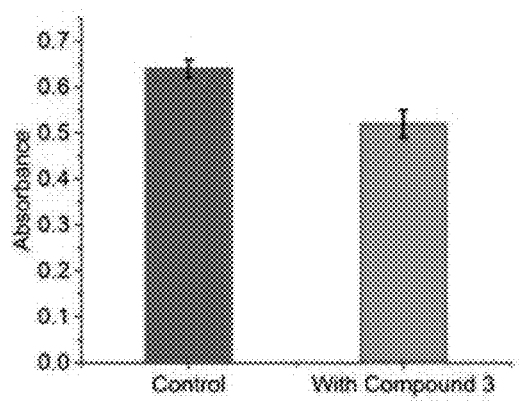
FIG. 5D shows absorbance results from a Glutamine kit assay (Abcam, ab83389) in U87 cells alone and U87 cells incubated with Compound 3 Ad-Glutamine analog, showing the Compound 3 analog competes with the cellular glutamine, according to embodiments of the present invention.
Figure 5E:
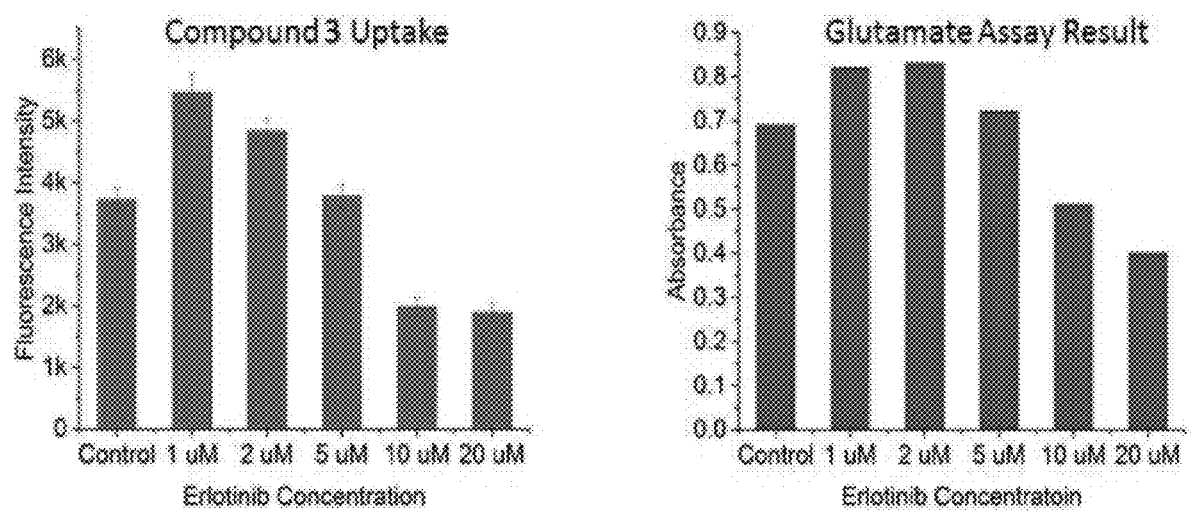
FIG. 5E shows the immunofluorescence results (left graph) assaying Compound 3 Ad-Glutamine analog uptake in U87 cells with increasing amounts of the EGFR inhibitor erlotinib as indicated, and the absorbance results (right graph) assaying glutamate as an indicator of glutamine uptake in U87 cells with increasing amounts of erlotinib as indicated, according to embodiments of the present invention.
Figure 5F:
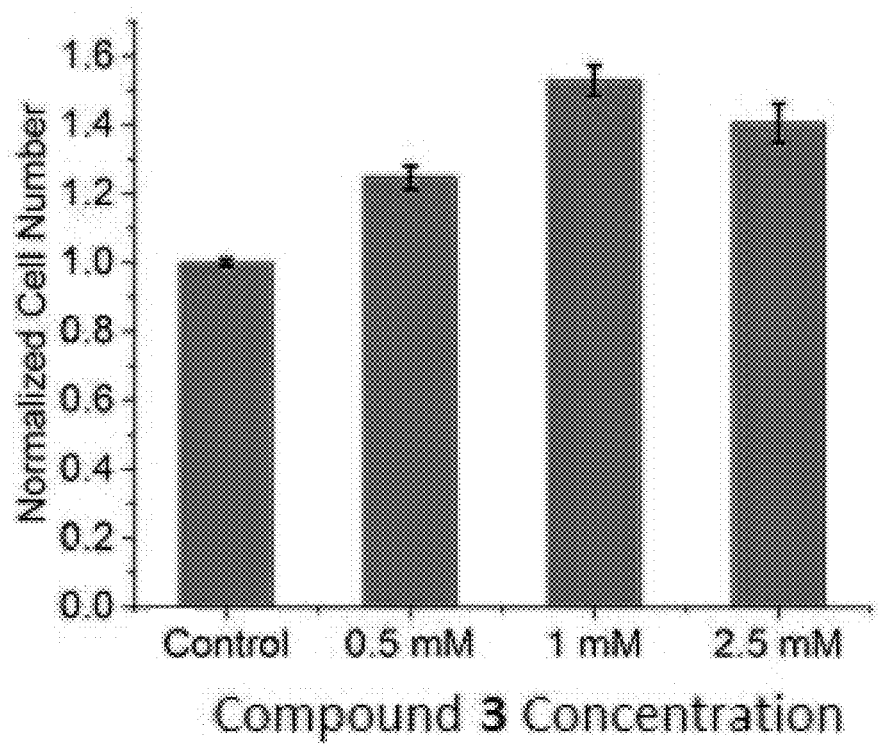
FIG. 5F is a graph showing cell toxicity of the Compound 3-Ad-Glutamine analog at the indicated concentrations with cell numbers normalized to the control sample, according to embodiments of the present invention.

In some embodiments of the present invention, a method for measuring glutamine uptake in a cell includes incubating the cell with a glutamine analog, followed by lysis of the cell, and quantification of the amount of the glutamine analog in the cell. As shown in FIG. 5A, the glutamine analog is a glutamine derivative conjugated to adamantane as shown in Compounds 1-8. These 8 glutamine analogs (adamantane conjugates) were assayed for their ability to substitute for glutamine. As shown in FIG. 5B, Compounds 3 and 8 exhibited temperature-dependency and glutamine-dependency. As shown in FIG. 5C, Compound 3 was further analyzed for uptake in U87 cells in which the sodium-dependent SLC1A5 amino acid transporter required for glutamine uptake was inhibited under sodium free conditions and siRNA knock-down of SLC1A5 resulted in inhibition of cell uptake of Compound 3 indicating that Compound 3 is taken up by the cell using the glutamine transporter. Further comparative analysis with glutamine is shown in FIGS. 5D and 5E, and Compound 3-Ad-Glutamine does not inhibit cell growth (FIG. 5F). As such, the Compound 3 Ad-Glutamine analog is a validated substitute for glutamine.

Figure 6A:
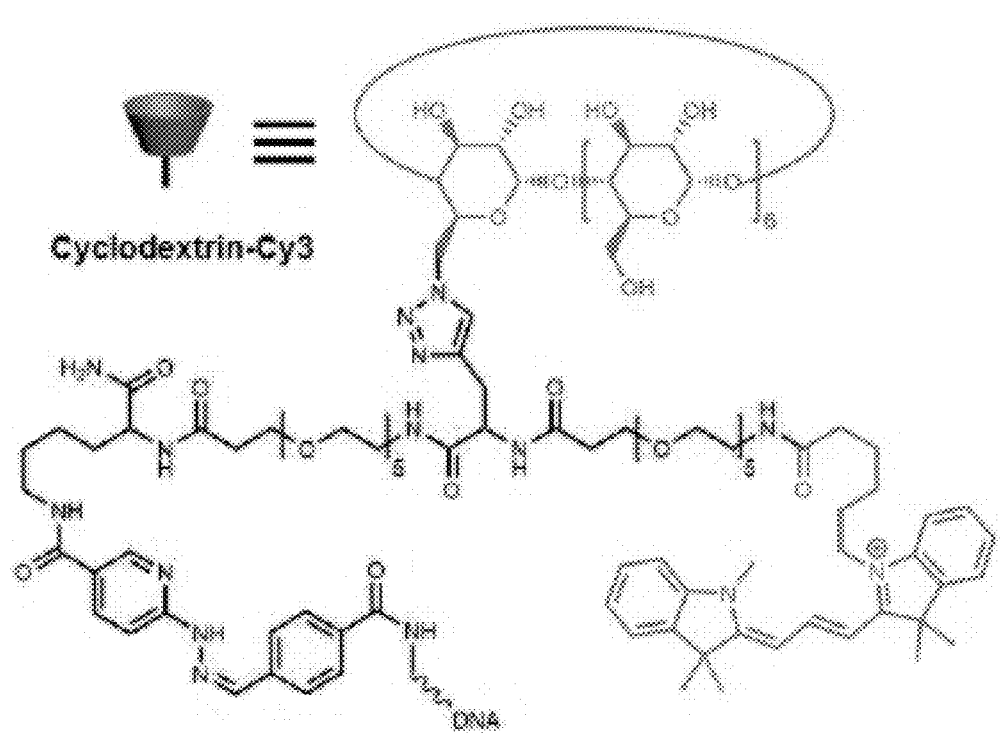
FIG. 6A is a schematic of a Cyclodextrin-Cyanine 3 DNA (Cyclodextrin-Cy3) conjugate with the cyanine 3 dye structure shown in green, the cyclodextrin structure shown in black, and DNA shown conjugated to the cyclodextrin, according to embodiments of the present invention.
Figure 6B:
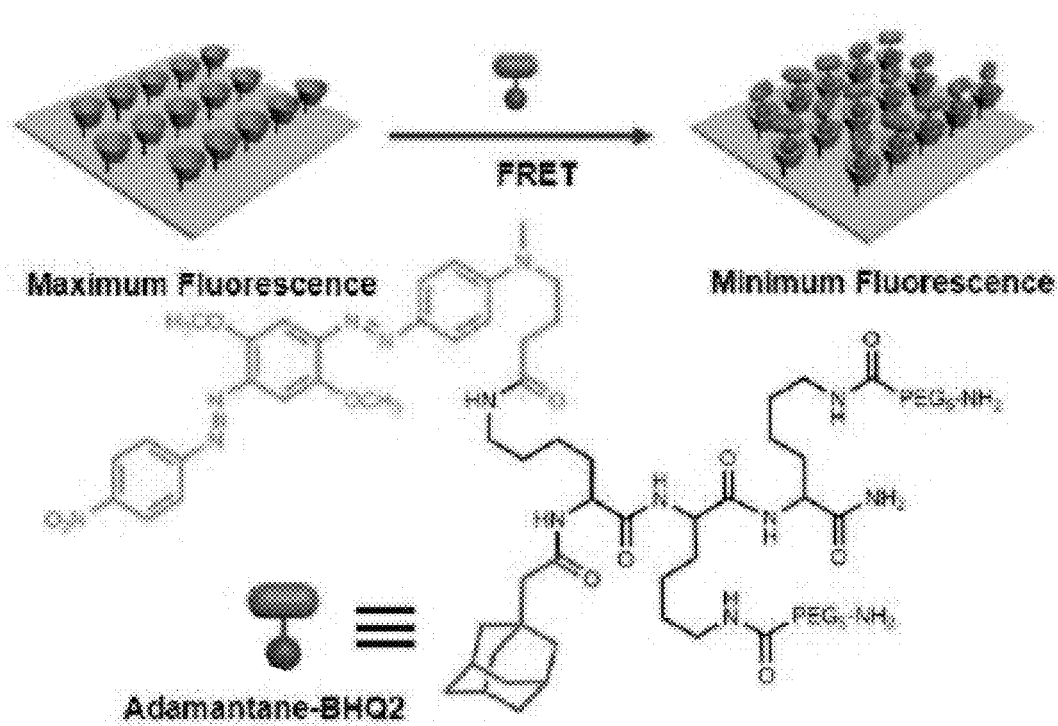
Figure 6C:
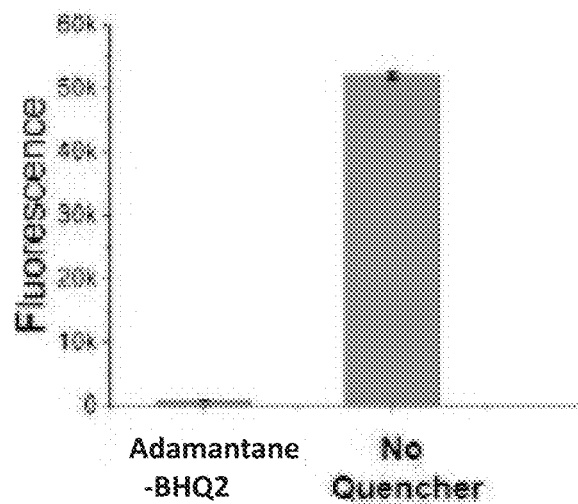
Figure 6D:
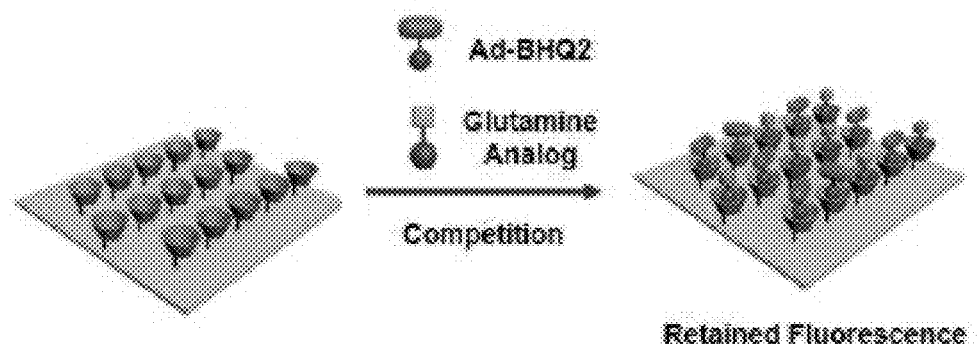
Figure 6E:
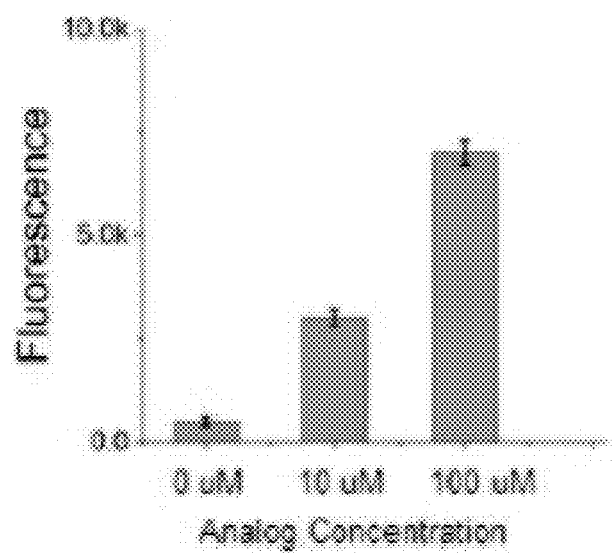
Figure 7B:
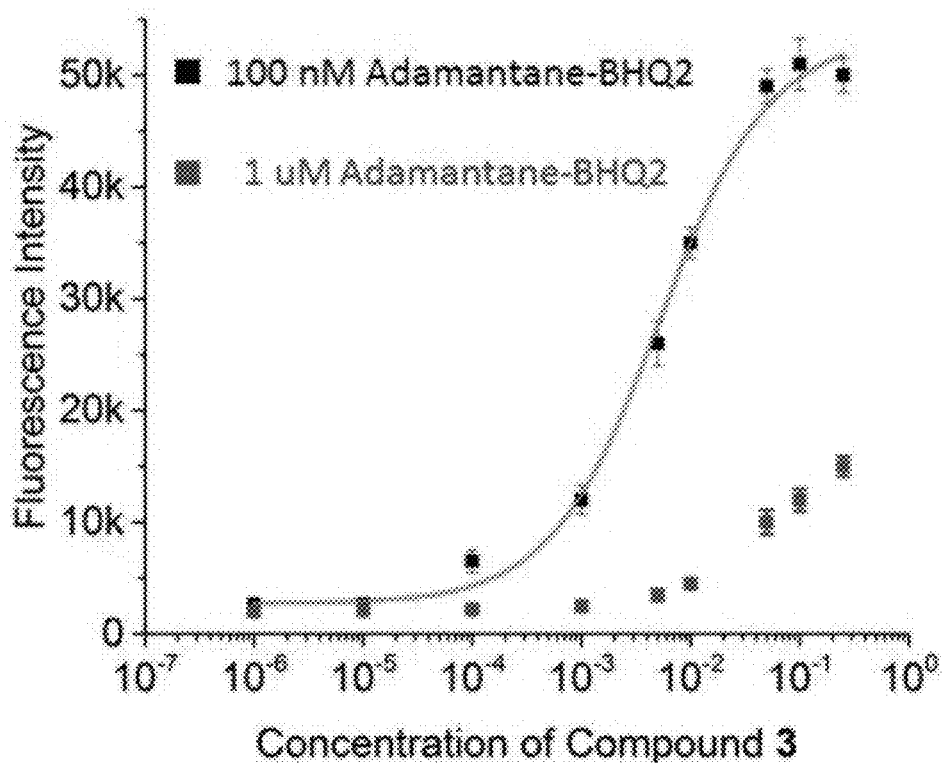
FIG. 7B is a calibration curve graph measuring the amount of fluorescence as a function of concentration (M) of Adamantane-Glutamine using the competitive binding FRET assay shown in FIG. 2C and FIGS. 5A-5E, in which the fluorescence intensity depends on the concentration of the Adamantane-BHQ2 quencher shown here at 100 nM (black squares) and 1 μM (blue squares), according to embodiments of the present invention.

For measuring glutamine cell uptake, the Ad-Glut analog is incubated with a cell or cells, followed by a wash to remove any Ad-Glutamine analog which remained in the cell medium. Following cell lysis, the intracellular Ad-Glutamine analog is released and binds to dye-labeled (e.g., cyanine 3 (Cy3)) cyclodextrin (depicted in FIG. 6A) immobilized on the chip platform as in FIG. 6B. The cyanine group serves as a FRET donor and the cyclodextrin serves as a supramolecular host. The adamantane-glutamine competes with an adamantane-BHQ2 quenching conjugate for binding sites on the surface cyclodextrin in which the binding of adamantane-glutamine precludes binding and quenching by adamantane-BHQ2, thereby retaining fluorescence. Using this method, the fluorescence intensity readout positively correlates to the amount of Ad-Glutamine analog taken up by the cell and released upon lysis. For example, as depicted in FIG. 6D and shown in FIG. 6E, increased amounts of the Ad-Glutamine analog result in an increase in fluorescence. FIG. 7B shows the calibration of the Ad-Glutamine fluorescence using Adamantane-BHQ2 at 100 nM (black squares) and 1 µM (blue squares) with increasing amounts of Compound 3 Ad-Glutamine. As shown in FIG. 7B, the competitive binding in this assay renders the fluorescence intensity dependent on the concentration of Ad-BHQ2. Fluorescence intensities are quantified using laser scanning techniques as disclosed herein.

In some embodiments of the present invention, the glutamine analog for measuring glutamine uptake in a cell may be glutamine conjugated to adamantane forming Ad-Glutamine as discussed above and shown in FIG. 5A. In some embodiments, glutamine may be conjugated to biotin to form a biotin-labeled glutamine conjugate which may be captured on a chip platform using immobilized fluorescently labeled streptavidin and assayed using a FRET assay as disclosed herein for biotin-labeled glucose.

Simultaneous Quantification of cAMP, cGMP, GSH, Glucose Uptake, and Glutamine Uptake Incorporating the metabolite immunofluorescent assays as disclosed herein with established (e.g., commercially available) protein immunofluorescent assays, provides for an analysis of the metabolites and proteins in a single cell assay. The capability to simultaneously quantify metabolites and proteins allows for elucidation of cellular relationships that are hard to establish when the analytes (e.g., metabolites and proteins being analyzed) are measured independently. Furthermore, the simultaneous quantification also allows for a steady state kinetic model that characterizes energy flux through the analyzed cell and correlates that flux with receptor signaling—e.g., receptor tyrosine kinase signaling.

Incorporation of the metabolite assays as disclosed herein with established protein assays may be carried out on any suitable chip platform or array chip. For single cell analysis, this multiplex array of immunofluorescent assays may be incorporated into a single celled platform, e.g., a single cell barcode chip (SCBC).

In some embodiments of the present invention, a method of simultaneously quantifying at least one cellular metabolite and one cellular protein includes preparing the array chip with immobilized capture probes corresponding to the analytes to be measured.

Figure 8A:
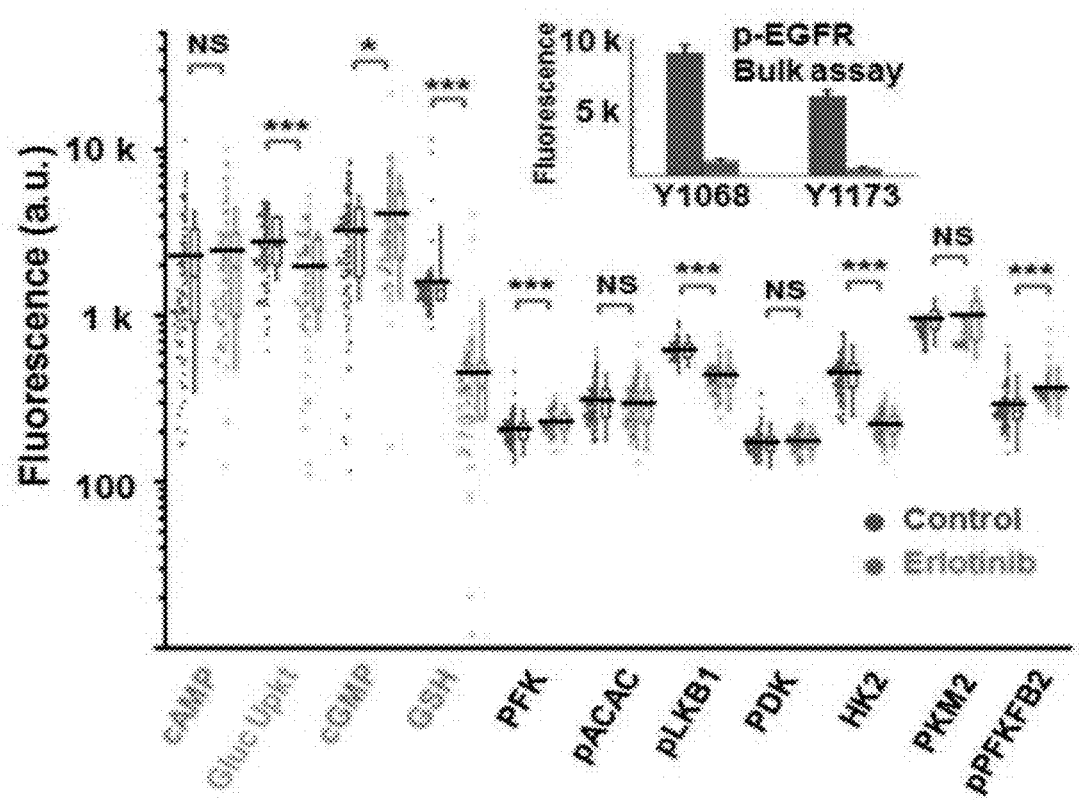
FIG. 8A shows one-dimensional scatter plots of metabolite and protein fluorescence data simultaneously assayed in GBM39 cells using a single cell barcode chip (SCBC) patterned to detect cAMP, Gluc-Bio, cGMP, and GSH metabolites using immunofluorescence assays as shown in FIGS. 2A-2B and seven metabolism-related proteins and phosphoproteins including phosphofructokinase (PFK), phospho-acetyl-CoA Caraboxylase (pACAC), phospho-liver kinase B1 (pLKB1), phosphoinositide-dependent kinase 1 (PDK), hexokinase 2 (HK2), pyruvate kinase M2 (PKM2), and phospho-carbohydrate kinase family protein (pPFKB2), according to embodiments of the present invention, in which the neurosphere tumor model (GBM39) cells expressing epidermal growth factor receptor (EGFR) variant (v) III oncogene having a constitutively activated EGFR pathway were incubated in the presence (red) or absence (blue) of the EGFR inhibitor erlotinib. The insert graph shows a bulk fluorescence assay of erlotinib inhibition at two tryosine (Y) phosphorylation sites—Y1068 and Y1173 in the GBM39 cells.
Figure 8B:
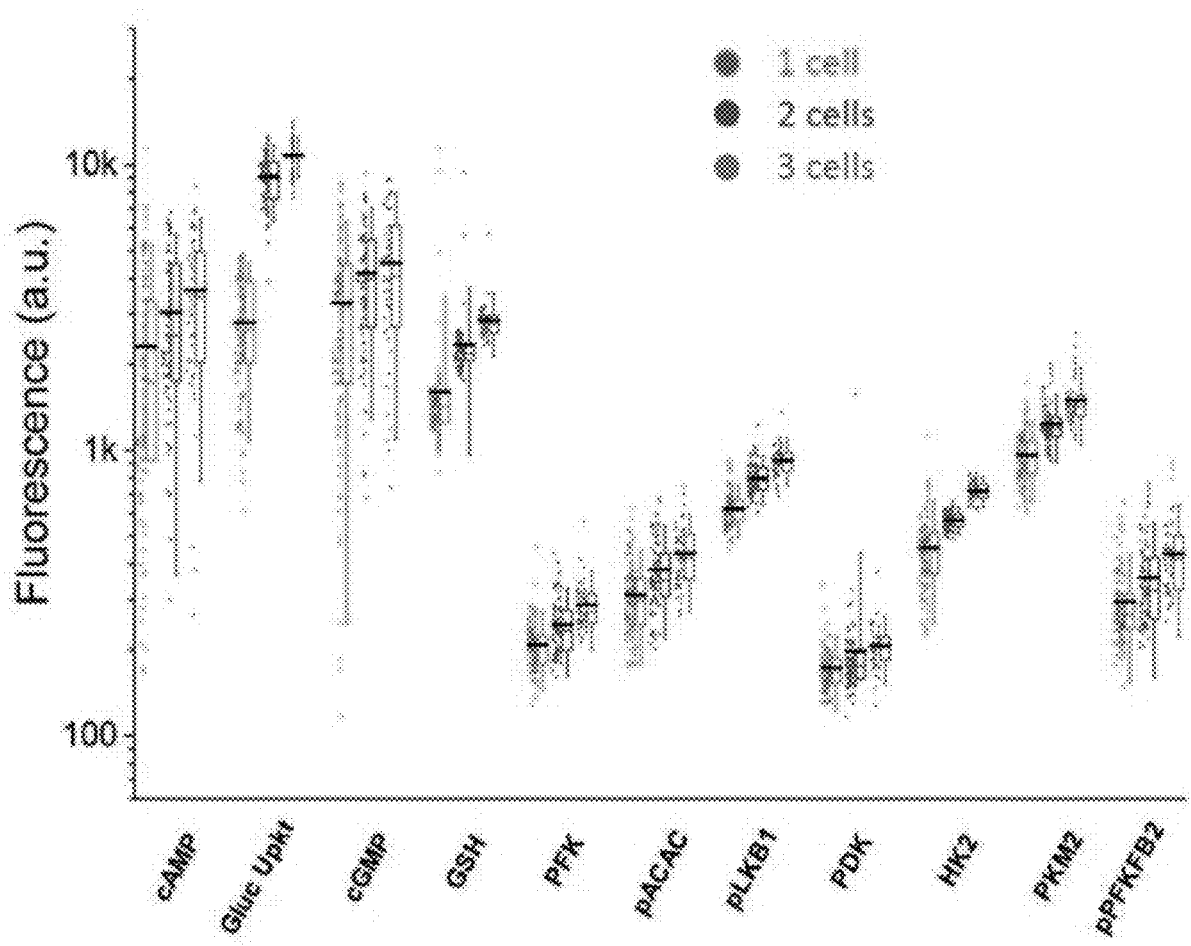
FIG. 8B shows metabolite and protein fluorescence data simultaneously assayed in GBM39 cells using a SCBC assay measuring the same analytes as in FIG. 8A for 1 GBM39 cell (red), 2 GBM39cells (blue), and 3 GBM39cells (green), showing that the relevant fluorescence signal increased with the increase in cell number, thereby demonstrating validity of the SCBC assay, according to embodiments of the present invention.

Using a SCBC as shown in FIGS. 1A and 1B and further disclosed herein, simultaneous quantification of a panel of metabolites and proteins, including cAMP, cGMP, glucose uptake, glutathione along with phosphofructokinase (PFK), phospho-acetyl-CoA Caraboxylase (pACAC), phospho-liver kinase B1 (pLKB1), phosphoinositide-dependent kinase 1 (PDK), hexokinase 2 (HK2), pyruvate kinase M2 (PKM2), and phospho-carbohydrate kinase family protein (pPFKB2) was performed in single cells separated from the GBM39 neurosphere tumor model. These GBM neurospheres are patient-derived glioblastoma cells that express epidermal growth factor receptor (EGFR) variant (v) III oncogene, which renders signaling through the EGFR pathway constitutively activated and sensitive to EGFR inhibitors. The GBM39 cells were interrogated across this panel of metabolites and proteins before and following 24 hours (h) of treatment with the EGFR inhibitor, erlotinib. FIG. 8A shows one-dimensional scatter plots of the single cell fluorescence data for each analyte and each condition investigated. To validate that the observed data are representative of a single cell, the assay was performed in 1, 2, and 3 cells in which an increase in cell number corresponded with an increase in fluorescent signal as shown in FIG. 8B.

A multiplex assay incorporating the glutamine uptake assay according to embodiments of the present invention was performed using a SCBC platform in U87 human glioblastoma cells having amplified epidermal growth factor receptor (EGFR) expression. This multiplex panel includes cAMP, Gluc-Bio, cGMP, GSH, and Ad-Glutamine metabolites using the immunofluorescent assays disclosed herein according to embodiments of the present invention, and phosphofructokinase (PFK), phospho-acetyl-CoA Caraboxylase (pACAC), phospho-liver kinase B1 (pLKB1), phosphoinositide-dependent kinase 1 (PDK), hexokinase 2 (HK2), pyruvate kinase M2 (PKM2), and phospho-carbohydrate kinase family protein (pPFKB2), lactate dehydrogenase (LDH), cMyc, phospho-glycogen synthase kinase 3b (GSK3b), and phospho-adenosine monophosphate dependent kinase a (pAMPKa) in the absence (control) or presence of erlotinib at 1 µM or 10 µm.

Metabolite Assay Kit

In some embodiments of the present invention, the assays and conjugates disclosed herein may be provided in the form of chip arrays or kits of parts. An array sometimes referred to as a "microarray" or includes any one, two or three dimensional arrangement of addressable regions bearing a particular molecule associated to that region as exemplified and disclosed herein for the SCBC platform.

In a kit of parts, the metabolite conjugates are included in the kit. For example a kit may include at least one of the cAMP, cGMP, glutathione, glucose, and glutamine conjugates as disclosed herein. In some embodiments, the kit includes at least one of cAMP-HRP, cGMP-HRP, GSH-fluorescent dye, glucose-biotin, glutamine-adamantane, or any combination thereof. In some embodiments, the kit having at least one metabolite conjugate may also include the corresponding capture probe. For example, the kit may also include at least one of anti-cAMP antibody, anti-cGMP antibody, anti-glutathione antibody, streptavidin, and/or cyclodextrin. In some embodiments, the capture probes may be immobilized on a substrate (e.g., a glass slide). For example, the kit may include capture probes that are DNA-immobilized on a substrate.

In some embodiments, a kit may include detection agent to bind and detect the captured analyte. For example, a detection antibody or a quenching group for FRET analysis. A detection antibody may include a fluorescent tag. In some embodiments a kit including at least one of cAMP-HRP or cGMP-HRP may also include the corresponding anti-HRP detection antibody conjugated to a fluorescent dye as shown in FIG. 2B. In some embodiments a kit including at least glucose-biotin, also includes the quenching group biotin-BHQ2 for FRET analysis. In some embodiments, a kit including at least adamantane-glutamine also includes the quenching group adamantane-BHQ2.

In some embodiments of the present invention, a kit including the metabolite immunofluorescent components as disclosed herein also includes a substrate, such as an array chip or slide. In some embodiments, the kit may include additional components, for example, reference standards, instructions, as well as wash buffers and lysis buffers as disclosed herein.

The following Examples are presented for illustrative purposes only, and do not limit the scope or content of the present application.

EXAMPLES

Example 1

Chemicals and Reagents

Reduced L-glutathione (GSH, 98%), tris(2-carboxyethyl) phosphine hydrochloride (TCEP, 98%), biotin (99%), glucosamine hydrochloride (99%), 1-[Bis(dimethylamino) methylene]-1H-1,2,3-triazolo[4,5-b]pyridinium 3-oxid hexafluorophosphate (HATU, 97%), N,N-diisopropylethylamine (DIEA, 99%), citric acid (99.5%), sodium azide (99.5%), N-methyl-2-pyrrolidone (NMP, 99%), trifluoroacetic acid (TFA, 99%), triethylsilane (99%), piperidine (99.5%), glucose assay kit (GAHK-20), 1-adamantaneacetic acid (Adaa, 98%), 1-adamantylamine (97%), 1-adamantanecarboxylic acid (99%), copper(I) iodide (CuI, 98%), sodium L-ascorbate (98%), tetrakis(triphenylphosphine)palladium(0) (Pd0, 99%), phenylsilane (97%), Fmoc-L-Dap (Alloc)-OH (98.5), Fmoc-L-Dab(Alloc)-OH (99%), Fmoc-L-Orn(Alloc)-OH (99%), Fmoc-L-Glu(OAll)-OH (96%), and Fmoc-L-Asp(OAll)-OH (98%) were purchased from Sigma Aldrich (St. Louis, Mo.). Phosphate buffered saline was purchased from IrvineScientific (Santa Ana, Calif.). Alexa Fluor 647 C2-Maleimide (AF647-Mal) and Alexa Fluor 647 NHS ester (AF647-NHS) were purchased from Life Technologies (Grand Island, N.Y.). cAMP-HRP and cGMP-HRP conjugates were purchased from GeneScript (Piscataway, N.J.). Methanol, dichloromethane, ethyl ether, deionized water and HPLC-grade acetonitrile were purchased from VWR (Radnor, Pa.). Succinimidyl 4-hydrazinonicotinate acetone hydrazine (S-HyNic), succinimidyl 4-formylbenzoate (S-4FB) and anhydrous N,N-dimethylformamide (DMF) were purchased from Solulink (San Diego, Calif.). Biotin NovaTag™ resin, Fmoc-Lys(Boc)-OH, Fmoc-NH-(PEG)4-COOH were purchased from Millipore (Temecula, Calif.). BHQ-2 carboxylic acid was obtained from Biosearch Technologies (Petaluma, Calif.). Fmoc-Rink Amide resin (0.6 mmol/g loading), 2-Chlorotrityl Chloride resin (0.5 mmol/g loading), Fmoc-L-Lys(Alloc)-OH, Fmoc-L-Gly(Propargyl)-OH, Fmoc-NH-PEG5-CH2CH2COOH (PEG5), Fmoc-Lys(Boc)-OH were purchased from ChemPep Inc. (Wellington, Fla., U.S.A.). Cyanine3 carboxylic acid (Cy3) was purchased from Lumiprobe (Hallandale Beach, Fla., U.S.A.). BHQ2 carboxylic acid (BHQ2) was obtained from Biosearch Technologies (Petaluma, Calif., U.S.A.). Succinimidyl 4-formylbenzoate (S-4FB) and 6-Boc-hydrazinonicotinic acid (Boc-HNA) were purchased from Solulink (San Diego, Calif., U.S.A.). Glutamate assay kit was purchased from Abcam (Cambridge, Mass., U.S.A.). siRNA against SLC1A5 and the siRNA transfection kit was purchased from ThermoFisher (Grand Island, N.Y., U.S.A.).

Example 2

Cyclodextrin-Cy3

A sequence of Lys(Alloc)-PEG5-Gly(Propargyl)-PEG5-Cy3 was synthesized on 100 mg of Rink Amide resin following standard solid phase peptide synthesis protocol using dimethylformamide as solvent as described in Deyle et al., 2015, *Nat. Chem.* 7:455-462, the entire content of which is herein incorporated by reference. The deprotection of the Fmoc group was achieved by piperidine (20% v/v in DMF) treatment (5 mL, 3×10 min) and the amide bond coupling was carried out through HATU/DIEA process (2 mL of 200 mM HATU/DMF, 2 mL of 200 mM amino acid/DMF, 0.5 mL of DIEA, 1 hr incubation at room temperature). The Alloc protecting group was removed through treating the resin with 100 mg of Pd0 and 0.5 mL of phenylsilane in 5 mL of dichloromethane for 2 hr. Subsequently, Boc-HNA was coupled to the peptide. The peptide was cleaved from the resin using 5 mL of TFA with 2.5% water, 2.5% acetone and 2.5% triethylsilane and dried under vacuum. Then, the peptide was dissolved in 10 mL of DMF and mixed with 200 mg of CuI, 300 mg of sodium ascorbate, 2 mL of piperidine and 500 mg of mono-6-azido-6-deoxy-β-cyclodextrin as described in Krzywinski et al., 2009, *Genome Res.*, 19:1639-1645, the entire content of which is incorporated by reference. The reaction was incubated at room temperature for 48 hrs and the product was purified through reverse phase HPLC. MALDI-TOF, C118H182O50N14, [MH+] calc. 2596.22. found 2596.26.

Example 3

Cyclodextrin-Cy3-DNA 0.1 mg of S-4FB was dissolved in 5 uL of anhydrous DMF and added into 20 uL of ssDNA oligo solution (200 uM in PBS). This solution was incubated at room temperature for 2 hours and then buffer exchanged to a pH 5.0 citrate buffer using Zeba spin columns (7K MWCO, Thermo Fisher Scientific, Pittsburgh, Pa.). The resulting solution was mixed with 50 uL of Cyclodextrin-Cy3 solution (50 uM in pH 5.0 citrate buffer). After 12 hr of incubation at room temperature, the product was purified through FPLC.

Example 4

Adamantane-BHQ2

A sequence of Lys(Boc)-Lys(Boc)-Lys(Alloc)-Adaa was synthesized on 100 mg of Rink Amide resin using aforementioned protocols. After Alloc deprotection, BHQ2 was conjugated to the peptide through HATU coupling. The peptide was then cleaved from the resin using 95% TFA with 2.5% water and 2.5% triethylsilane. After removing solvent under vacuum, the peptide was dissolved in 2 mL of acetonitrile and coupled with PEG5 through HATU coupling (2 mL of 200 mM HATU/acetonitrile, 2 mL of 200 mM PEG5/acetonitrile, 0.5 mL of DIEA, 1 hr incubation at room temperature). Subsequently, 5 mL of piperidine was added to perform Fmoc deprotection (room temperature, 20 min). After removing the solvent under vacuum, the remaining solid was extracted with 5 mL of 50% water/49.9% acetonitrile/0.1% TFA. The product was then purified through reverse phase HPLC. MALDI-TOF, C81H129N15O21, [MH+] calc. 1648.96. found 1648.96.

Example 5

3-(adamantane-1-carboxamido)-2-aminopropanoic acid (compound 1)

1.5 mmol of Fmoc-Dap(Alloc)-OH was dissolved in 20 mL of dry dichloromethane and 1 mL of DIEA was added into the solution. 2 g of 2-Chlorotrityl Chloride resin was added into the solution and the mixture was stirred at room temperature for 1 hr before 2 mL of methanol was added into the solution. After 15 min, the solution was filtered and the resin was washed with dichloromethane and dried under vacuum. The Alloc group was removed through aforementioned protocol, and 1-adamantanecarboxylic acid was coupled to the side chain amine through HATU/DIEA reaction. The Fmoc protecting group was subsequently removed by piperidine treatment. The modified amino acid was cleaved from the resin using 1% TFA in dichloromethane (1 hr). The product was purified through reverse phase HPLC. 1H-NMR 400 MHz, D2O, δ=3.98 (dd, 1H, J=5.8, 4.4 Hz), 3.65-3.54 (m, 2H), 1.89-1.93 (m, 3H), 1.70 (d, 6H, J=2.9 Hz), 1.66-1.50 (m, 6H). HR-FAB, C14H22O3N2, [MH+] calc. 267.1709. found 267.1700.

Example 6

4-(adamantane-1-carboxamido)-2-aminobutanoic acid (compound 2)

Compound 2 was synthesized with protocols similar to compound 1, with Fmoc-Dab(Alloc)-OH as the starting material. 1H-NMR 400 MHz, D2O, δ=3.76 (t, 1H, J=6.5 Hz), 3.37-3.17 (m, 2H), 2.02 (qd, 2H, J=6.7, 4.8 Hz), 1.95-1.83 (m, 3H), 1.70 (d, 6H, J=2.9 Hz), 1.68-1.52 (m, 6H). HR-FAB, C15H24O3N2, [MH+] calc. 281.1865. found 281.1860.

Example 7

5-(adamantane-1-carboxamido)-2-aminopentanoic acid (compound 3)

Compound 3 was synthesized with protocols similar to compound 1, with Fmoc-Orn(Alloc)-OH as the starting material. 1H-NMR 400 MHz, D2O, δ=3.90 (t, 1H, J=6.1 Hz), 3.13 (td, 2H, J=6.7, 2.0 Hz), 1.90 (m, 3H), 1.86-1.73 (m, 2H), 1.73-1.66 (m, 6H), 1.69 (d, 6H, J=2.9 Hz), 1.50-1.40 (m, 2H). HR-FAB, C16H26O3N2, [MH+] calc. 295.2022. found 295.2026.

Example 8

N5-(adamantan-1-yl)glutamine (compound 4)

Compound 4 was synthesized with protocols similar to compound 1, with Fmoc-Glu(OAll)-OH as the starting material. The OAll deprotection procedure is the same as that of Alloc deprotection. After removing OAll group, 1-adamantylamine was coupled to the side chain carboxylic acid through HATU/DIEA procedure. After cleaving, the modified amino acid was purified by reverse phase HPLC. 1H-NMR 400 MHz, D2O, δ=3.77 (t, 1H, J=6.3 Hz), 2.24 (td, 2H, J=7.5, 3.5 Hz), 2.02 (qd, 2H, J=7.2, 6.7, 2.0 Hz), 1.94 (s, 3H), 1.88-1.78 (m, 6H), 1.63-1.39 (m, 6H). HR-FAB, C15H24O3N2, [MH+] calc. 281.1865. found 281.1862.

Example 9

3-(2-(adamantan-1-yl)acetamido)-2-aminopropanoic acid (compound 5)

Compound 5 was synthesized with protocols similar to compound 1, with Adaa coupled to the side chain amine. 1H-NMR 400 MHz, D2O, δ=4.04 (dd, 1H, J=5.7, 4.0 Hz), 3.74-3.48 (m, 2H), 2.00-1.88 (m, 2H), 1.87-1.75 (m, 3H), 1.64-1.34 (m, 12H). HR-FAB, C15H24O3N2, [MH+] calc. 281.1865. found 281.1858.

Example 10

4-(2-(adamantan-1-yl)acetamido)-2-aminobutanoic acid (compound 6)

Compound 6 was synthesized with protocols similar to compound 2, with Adaa coupled to the side chain amine. 1H-NMR 400 MHz, D2O, δ=3.84 (dd, 1H, J=7.4, 5.9 Hz), 3.38-3.11 (m, 2H), 2.16-1.93 (m, 2H), 1.83 (s, 3H), 1.67-1.32 (m, 12H). HR-FAB, C16H26O3N2, [MH+] calc. 295.2022. found 295.2035.

Example 11

5-(2-(adamantan-1-yl)acetamido)-2-aminopentanoic acid (compound 7)

Compound 7 was synthesized with protocols similar to compound 3, with Adaa coupled to the side chain amine.

1H-NMR 400 MHz, D2O, δ=3.95 (t, 1H, J=6.2 Hz), 3.12 (td, 2H, J=7.0, 1.2 Hz), 1.98-1.75 (m, 7H), 1.67-1.35 (m, 14H). HR-FAB, C17H28O3N2, [MH+] calc. 309.2178. found 309.2167.

Example 12

N4-(adamantan-1-yl)asparagine (compound 8)

Compound 8 was synthesized with protocols similar to compound 4, with Fmoc-Asp(OAll)-OH as the starting material. 1H-NMR 400 MHz, D2O, δ=3.96 (dd, 1H, J=6.9, 4.7 Hz), 2.78-2.56 (m, 2H), 1.98-1.90 (m, 3H), 1.80-1.88 (m, 6H), 1.50-1.62 (m, 6H). HR-FAB, C14H22O3N2, [MH+] calc. 267.1709. found 267.1709.

Example 13

U87 Cell Culture and Drug Treatment

U87/EGFRV3 cells were provided by Prof. Paul S. Mischel (UCSD, San Diego, U.S.A.) and cultured in Dulbecco's modified eagle media (DMEM, Gibco, ThermoFisher Scientific, Grand Island, N.Y., U.S.A.) supplemented with 10% of fetal bovine serum (Thermo Fisher Scientific) and 100 U/mL of penicillin and streptomycin in a humidified 5% CO2 (v/v) incubator, at 37° C. For the drug treatment, 1 million cells were first cultured for 1 day and then the medium was changed with 10 mL of new media containing 1 μM or 10 μM of erlotinib (ChemieTek, Indianapolis, Ind., U.S.A.) and cultured for 24 hr before the glutamine analog uptake experiments or SCBC measurements.

Example 14

Single Cell Suspension Preparation

The media in a U87/EGFRV3 culture was removed and the cells were treated with 0.25% Trypsin/EDTA (Thermo Fisher Scientific) for 10 min at 37° C. The original media was added back to the disassociated cells and the suspension was centrifuged at 500 g for 5 min. After removing the supernatant, the cells were resuspended in warm media at a concentration of 1 million/mL.

Example 15

Glutamine Analog Uptake

U87/EGFRV3 single cells were resuspended in DMEM media or glutamine-free DMEM media (Thermo Fisher Scientific) with 1 mM of glutamine analog and incubated at 37° C. or 4° C. for 20 min. Subsequently, the cells were collected via centrifugation (500 g, 5 min) and washed with cold PBS for three times. Then, the cells were lysed using cell lysis buffer (Cell Signaling, Boston, Mass., U.S.A.). To quantify the analog uptake, the lysate was mixed with an Adamantane-BHQ2 solution (100 nM in water) incubated on the glass slide with surface hybridized Cyclodextrin-Cy3-DNA at room temperature for 1 hr. the glass slide was then washed and spin dried. The fluorescence signal on the glass slide was read out using an Axon GenePix 4400A scanner.

Example 16

Synthetic Procedures

Glutathione-AlexaFluor 647 (GSH-AF647). The synthetic scheme of GSH-AF647 is shown in FIG. 3A. 100 uL of 10 mM reduced glutathione in 1×PBS was mixed with 10 uL of 100 mM TCEP in 1×PBS and the solution was shaken at room temperature for 1 hr. Subsequently, 100 uL of AF647-Mal (10 mM, in DMSO) was added to the solution and the mixture was shaken in the dark at room temperature for 2 hours. The crude was separated using reverse-phase HPLC (C18 column, A:H2O, B:CH3CN, 100% A to 30% A). The fractions were collected and lyophilized. The product was characterized by mass spec (MALDI-TOF, [M+H+K]2+ calculated: 656.635, observed: 656.433).

Example 17

Glucose-Biotin (Gluc-Bio)

The synthesis of Gluc-Bio is shown in FIG. 4A. In a typical synthesis, 270 mg of biotin was dissolved in 30 mL of methanol and 2 mL of N,N-diisopropylethylamine. 380 mg of HATU was added into the solution and thoroughly mixed. In another flask, 215 mg of 2-glucosamine hydrochloride was suspended in 5 mL deionized water. This suspension was mixed with the biotin/HATU solution and stirred at room temperature for 3 hr. After removing the solvent under vacuum, the crude was mixed with 5 mL of water. The resulting mixture was filtered and the supernatant was purified using HPLC (C18 column, A:H2O, B:CH3CN, 100% A to 50% A). The product was characterized by mass spec (MALDI-TOF, [M+Na]+ calculated: 428.147, observed: 428.289).

Example 18

Biotin-BHQ2

Figure 10:
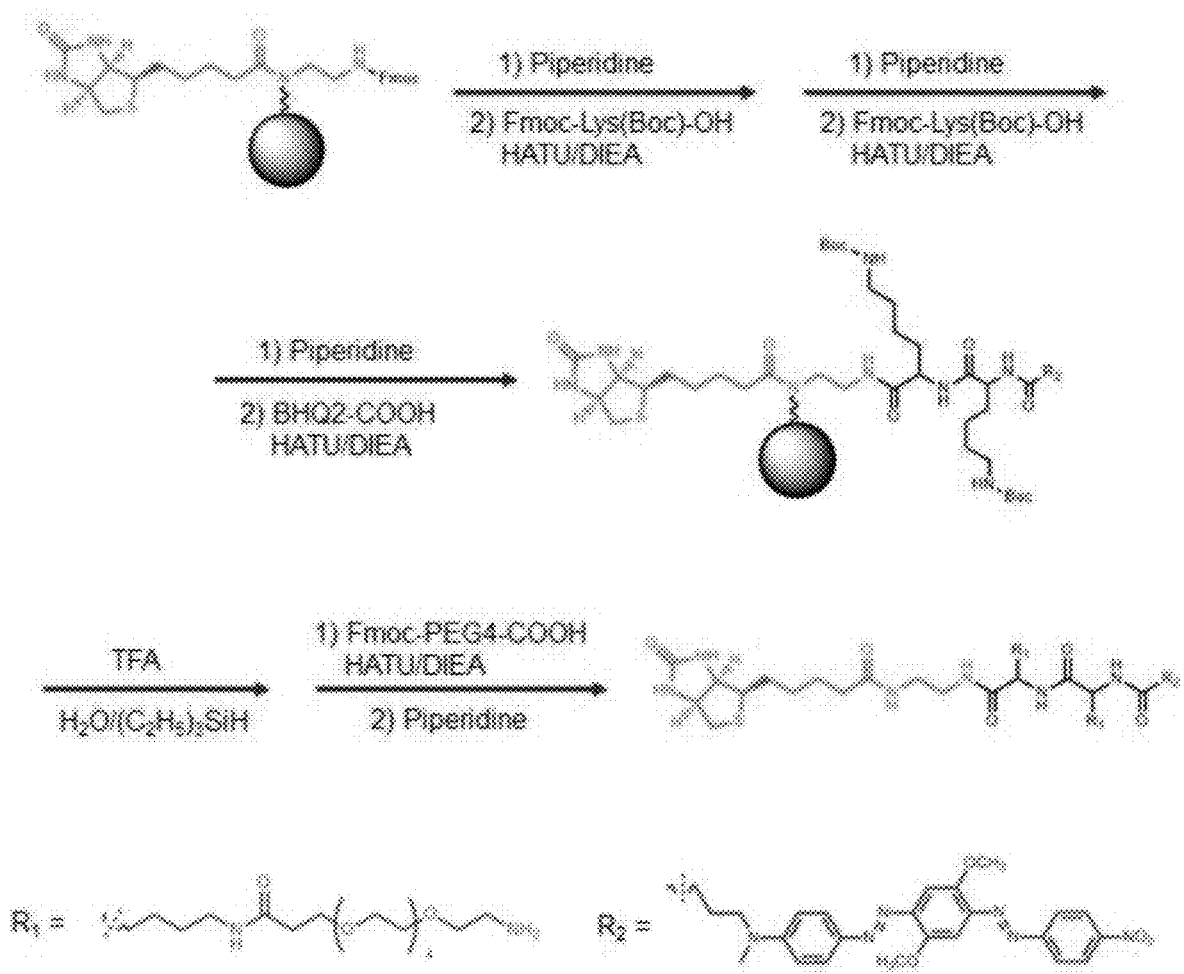
FIG. 10 is a synthetic scheme of Biotin-BHQ2, according to embodiments of the present invention.

The synthesis of Biotin-BHQ2 was based on the solid state peptide synthesis technique. The synthetic scheme is shown in FIG. 10. 100 mg of Biotin-NovaTag™ resin was suspended in 5 mL of NMP for 2 hr, and then treated with piperidine (5 mL and 10 min, repeat 3 times) to perform Fmoc-deprotection. The resin was then washed with 5 mL of NMP (20% in NMP) and resuspended in 1 mL of NMP. HATU (0.2 M in NMP, 2 mL), Fmoc-Lys(Boc)-OH (0.2 M in NMP, 2 mL) and DIEA (0.5 mL) were added and the mixture was incubated at room temperature for 1 hour. The solvent was then removed and the resin was washed with NMP (5 mL) for 3 times. Similar synthetic steps were carried out twice to attach another Fmoc-Lys(Boc)-OH and a BHQ2-COOH on to the resin, respectively. After synthesis, the resin was sequentially washed with NMP, methanol and dichloromethane and dried in air. To perform peptide cleavage, the resin was stirred in 5 mL of TFA with 2.5% water and 2.5% triethylsilane at room temperature for 2 hr. The mixture was filtered to remove the resin. The supernatant was mixed with 10 mL of ethyl ether and evaporated in air flow to afford a dark blue solid. This solid was then dissolved in 10 mL of acetonitrile/methanol (1/1) and then mixed with HATU (0.2 M in acetonitrile, 2 mL), Fmoc-NH-PEG4-COOH (0.4 M in acetonitrile, 1 mL) and DIEA (0.5 mL). The solution was stirred at room temperature for 3 hr. Subsequently, 10 mL of piperidine was added into the solution and mixed for 1 hr. The solvent was then removed under reduced pressure, resulting in a black solid. The solid was resuspended in 10 mL of water and then filtered. The supernatant was purified through HPLC to afford the product. (MALDI-TOF, [M+H]+ calculated: 1612.853, observed: 1613.186).

Example 19

Antibody AF 647 Conjugation

Commercial antibodies were purified with protein A/G resins (Pierce) following manufacture's protocols. The purified antibodies were buffer exchanged into pH 7.4 PBS buffer using Zeba protein desalting spin columns (Pierce). Purified detection antibodies were reacted with AF647-NHS following manufacture's protocol (Life technologies). The degree of labeling was confirmed by absorption spectra. The labeled antibodies were stored in pH 7.4 PBS buffer with 0.02% NaN3 as preservatives. The list of capture antibodies and detection antibodies and their manufactures are shown in Tables 1A and 1B, respectively.

TABLE 1A

| Catalog# | Capture Antibody Name | Manufacture |
|---|---|---|
| A00614 | cAMP Antibody, Rabbit Polyclonal | GenScript |
| GTX10020 | Streptavidin Antibody, Mouse Monoclonal | GeneTex |
| A00615 | cGMP Antibody, Rabbit Polyclonal | GenScript |
| GTX16200 | Glutathione Antibody, Mouse Monoclonal | GeneTex |
| AF7687 | Human/Mouse/Rat PFKM Antibody, Sheep Polyclonal | R&D Systems |
| AF231 | Human EGFR Antibody, Goat Polyclonal | R&D Systems |
| AF6898 | Human/Mouse/Rat Acetyl-CoA Carboxylase Antibody, Sheep Polyclonal | R&D Systems |
| AF8055 | Human LKB1 Antibody, Sheep Polyclonal | R&D Systems |
| ab110335 | Anti-PDK1 Antibody, Mouse Monoclonal | Abcam |
| AF3696 | Human c-Myc Antibody, Goat Polyclonal | R&D Systems |
| AF7244 | Human/Mouse/Rat PKM2 Antibody, Sheep Polyclonal | R&D Systems |
| NBP1-55415 | Lactate Dehydrogenase B Antibody, Rabbit Polyclonal | Novus Biologicals |
| DYC1590 | Phospho-GSK-3 beta (S9) DuoSet | R&D Systems |
| DYC3528 | Human Phospho-AMPK alpha 1 (T183) DuoSet | R&D Systems |
| 2867 | Hexokinase II Antibody, Rabbit Monoclonal | Cell Signaling |
| 13029 | PFKFB2 Antibody, Rabbit Monoclonal | Cell Signaling |

TABLE 1B

| Catalog# | Detection Antibody Name | Manufacture |
|---|---|---|
| ab8326 | Anti-HRP Antibody, Mouse Monoclonal | Abcam |
| 12746 | PFKP Antibody, Rabbit Monoclonal | Cell Signaling |
| AF7687 | Human/Mouse/Rat PFKM Antibody, Sheep Polyclonal | R&D Systems |
| MAB3570 | Human Phospho-EGFR (Y1068) Antibody, Mouse Monoclonal | R&D Systems |
| 4407 | Phospho-EGFR (Y1173) Antibody, Rabbit Monoclonal | Cell Signaling |
| 11818 | Phospho-Acetyl-CoA Carboxylase (Ser79) Antibody, Rabbit Monoclonal | Cell Signaling |
| 3482 | Phospho-LKB1 (Ser428) Antibody, Rabbit Monoclonal | Cell Signaling |
| 3820 | PDHK1 Antibody, Rabbit Monoclonal | Cell Signaling |
| 13871 | c-Myc Rabbit mAb (Alexa Fluor 647 Conjugate) | Cell Signaling |
| H00003945-M01 | Lactate Dehydrogenase B Antibody, Mouse Monoclonal | Novus Biologicals |
| 4053 | PKM2 Antibody, Rabbit Monoclonal | Cell Signaling |
| DYC1590 | Phospho-GSK-3 beta (S9) DuoSet | R&D Systems |
| DYC3528 | Human Phospho-AMPK alpha 1 (T183) DuoSet | R&D Systems |

TABLE 1B-continued

| Catalog# | Detection Antibody Name | Manufacture |
|---|---|---|
| MABN702 | Anti-HK Antibody, Mouse Monoclonal | EMD Millipore |
| 13064 | Phospho-PFKFB2 (Ser483) Antibody, Rabbit Monoclonal | Cell Signaling |

Example 20

DNA-Encoded Antibody Library (DEAL)

The DNA-encoded antibody library method was based on the literature (R. Bailey, et al., J. Am. Chem. Soc., 2007, 129, 1959-1967, the entire content of which is herein incorporated by reference). 1 mg of S-HyNic and 1 mg of S-4FB were dissolved in 172 uL and 50 uL of anhydrous DMF respectively. 100 ug of the purified antibody was reconstituted in PBS buffer at 1 mg/mL and 5 uL of the S-HyNic solution was added. In another vial, 50 uL of an ssDNA oligo solution (200 uM in PBS) was mixed with 12.5 uL of DMF, and 5 uL of the S-4FB solution was added. The antibody and the DNA solutions were incubated at room temperature for 2 hr. The excess of the S-HyNic and S-4FB were removed through buffer exchanging into a pH 6.0 citrate buffer using Zeba spin columns. The antibody and DNA solutions were then combined and incubated at room temperature for 2 hrs then at 4° C. overnight. The DNA-Antibody conjugate was purified through FPLC (GE, Pharmacia Superdex 200 gel filtration column) and concentrated by centrifugal filter (Millipore, Amicon Ultra-4, 10 kD). The complementary ssDNA were patterned on to polylysine-coated glass slides through microfluidic-guided covalent crosslinking procedure as disclosed herein. The conversion of surface ssDNA barcodes to capture antibody microarrays were achieved through incubating a mixture of DEAL conjugates with the glass slide at 37° C. for 1 hr. The Cyclodextrin-Cy3-DNA may also be incorporated onto the surface barcode through the same procedure. The lists of capture and detection antibodies used are shown in Tables 1A and 1B.

Example 21

DNA Patterning on Glass Slides

Figure 11:
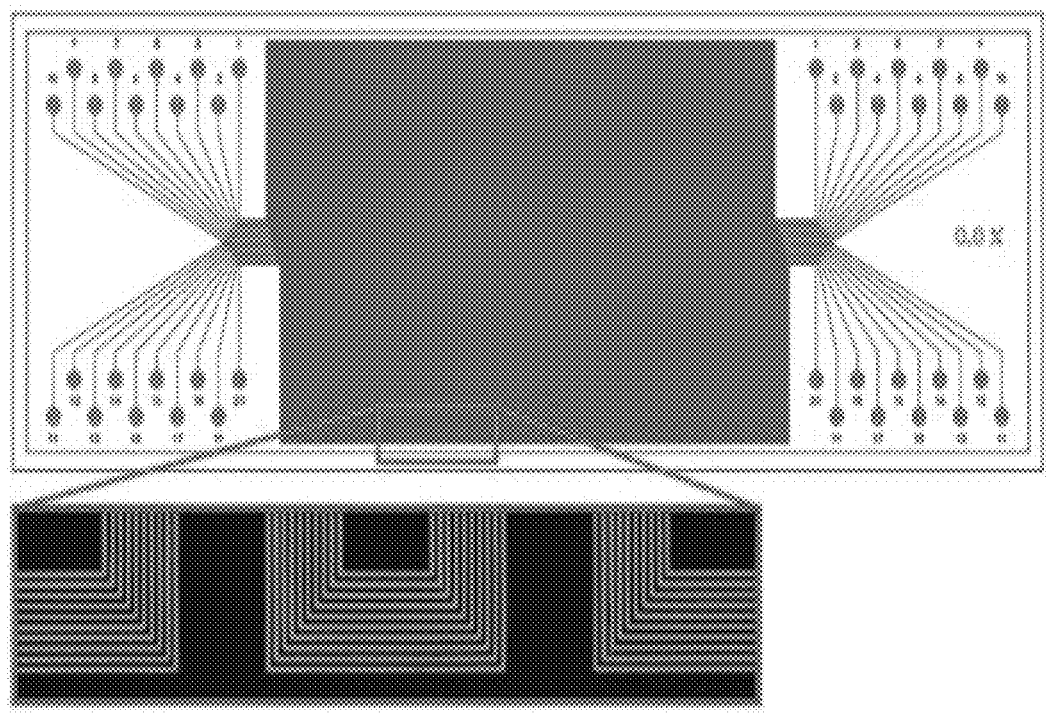
FIG. 11 is an illustration of the layout of the DNA barcode patterning on a slide in a SCBC platform with the zoom-in illustration showing a validation result of patterned DNA through Cy3-labeled complementary DNA hybridization, according to embodiments of the present invention.

DNA barcode patterns are prepared using previously reported methods (J. Yu, et al., Annu. Rev. Anal. Chem., 2014, 7, 275-295, the entire contents of which are herein incorporated by reference). First a master mold was prepared using the SU8 2035 photoresist. The mold was patterned with parallel channels at 10 um wide and 40 um high. A Sylgard 184 (A:B=7:1) polymer mix was poured onto the mold, degassed under vacuum and then cured at 80° C. for 2 hours. The cured PDMS was released from the mold and bonded onto a poly-L-lysine (PLL) coated glass slide (Thermo Scientific) to form enclosed channels. The number of analytes determines the number of the channels. The channels were flushed with a 0.1% PLL solution (Sigma Aldrich) and blown dry by air. Meanwhile, 5'-amine modified ssDNA was dissolved in a DMSO/H2O (2:3) solution at 300 uM and mixed with a 2 mM PBS solution of BS3 linker (Thermo Fisher) at 1:1 ratio (v/v). A library of freshly prepared DNA solutions were flown into different channels and the assembly was incubated at room temperature for 2 hours. The glass slide was then separated from the PDMS slab and washed with 0.02% SDS solution and water. Each patterned slide was validated using a solution of Cy3-labeled complementary DNA mixtures at one edge, and the fluorescence intensity of the barcodes were measured with an Axon GenPix 4400A scanner. The sequences of 5'-amine modified ssDNA are listed in Table 2, and the layout of the DNA patterning mold is shown in FIG. 11.

TABLE 2

| SEQ ID | Name | DNA Sequence |
|---|---|---|
| 1 | B | 5'-NH2-C6-AAA AAA AAA AGC CTC ATT GAA TCA TGC CTA-3' |
| 2 | B' | 5'-NH2-C6-AAA AAA AAA ATA GGC ATG ATT CAA TGA GGC-3' |
| 3 | C | 5'-NH2-C6-AAA AAA AAA AGC ACT CGT CTA CTA TCG CTA-3' |
| 4 | C' | 5'-NH2-C6-AAA AAA AAA ATA GCG ATA GTA GAC GAG TGC-3' |
| 5 | D | 5'-NH2-C6-AAA AAA AAA AAT GGT CGA GAT GTC AGA GTA-3' |
| 6 | D' | 5'-NH2-C6-AAA AAA AAA ATA CTC TGA CAT CTC GAC CAT-3' |
| 7 | E | 5'-NH2-C6-AAA AAA AAA AAT GTG AAG TGG CAG TAT CTA-3' |
| 8 | E' | 5'-NH2-C6-AAA AAA AAA ATA GAT ACT GCC ACT TCA CAT-3' |
| 9 | F | 5-NH2-C6-AAA AAA AAA AAT CAG GTA AGG TTC ACG GTA-3' |
| 10 | F' | 5'-NH2-C6-AAA AAA AAA ATA CCG TGA ACC TTA CCT GAT-3' |
| 11 | H | 5'-NH2-C6-AAA AAA AAA AAT TGA CCA AAC TGC GGT GCG-3' |
| 12 | H' | 5'-NH2-C6-AAA AAA AAA ACG CAC CGC AGT TTG GTC AAT-3' |
| 13 | I | 5'-NH2-C6-AAA AAA AAA ATG CCC TAT TGT TGC GTC GGA-3' |
| 14 | I' | 5'-NH2-C6-AAA AAA AAA ATC CGA CGC AAC AAT AGG GCA-3' |
| 15 | K | 5'-NH2-C6-AAA AAA AAA ATA ATC TAA TTC TGG TCG CGG-3' |
| 16 | K' | 5'-NH2-C6-AAA AAA AAA ACC GCG ACC AGA ATT AGA TTA-3' |
| 17 | L | 5'-NH2-C6-AAA AAA AAA AGT GAT TAA GTC TGC TTC GGC-3' |
| 18 | L' | 5'-NH2-C6-AAA AAA AAA AGC CGA AGC AGA CTT AAT CAC-3' |
| 19 | N | 5'-NH2-C6-AAA AAA AAA AGT CCT CGC TTC GTC TAT GAG-3' |
| 20 | N' | 5'-NH2-C6-AAA AAA AAA ACT CAT AGA CGA AGC GAG GAC-3' |
| 21 | O | 5'-NH2-C6-AAA AAA AAA ACT TCG TGG CTA GTC TGT GAC-3' |
| 22 | O' | 5'-NH2-C6-AAA AAA AAA AGT CAC AGA CTA GCC ACG AAG-3' |

Example 22

Preparation of Single Cell Suspensions

GBM 39 neurospheres were collected via centrifugation at 450 g for 5 min and the media was removed. The cells were then treated with 0.05% Trypsin/EDTA (Life Technologies) for 5 min at room temperature and the original media was added back to the pellet. The suspension was then centrifuged again and the supernatant was discarded. The cells are now disassociated as single cells and ready for tests.

Example 23

GBM39 Cell Culture and Drug Treatment

GBM39 primary neurospheres were provided by Prof. C. David James (UCSF, San Francisco, U.S.A.) and cultured in Dulbecco's Modified Eagle Media Nutrient Mix F-12 (DMEM/F12, Invitrogen) supplemented with B27 (Invitrogen), Glutamax (Invitrogen), Heparin (1 µg/mL), Epidermal Growth Factor (EGF, 20 ng/mL, Sigma), Fibroblast Growth Factor (FGF, 20 ng/mL, Sigma) and 100 U/mL of penicillin and streptomycin (Gibco) in a humidified 5% $CO_2$ (v/v) incubator, at 37° C. For the drug treatment, 1 million cells were suspended in 10 mL of media and were cultured for several days to form neurospheres. Subsequently, the medium was changed to 10 mL of new media containing 1 µM erlotinib (ChemieTek). The cells were then treated for designated periods of time and processed for tests.

Example 24

Gluc-Bio/FDG Kinetic Measurements

Aforementioned drug treated GBM39 cells were dissociated into single cells and re-suspended in pre-warmed glucose-free, serum-free media (DMEM, Invitrogen) at a concentration of 105 cells/mL (for FDG) or 2×105 cells/mL (for Gluc-Bio). Concentrated aqueous solution of Gluc-Bio or FDG was added to the cell suspension (final concentration: 10 µg/mL of Gluc-Bio, 4 uCi/mL of FDG). The cells were incubated at 37° C. for 10 min (Gluc-Bio) or 1 hr (FDG). At the end of incubation, the cells were collected via centrifugation and washed three times with cold PBS buffer (2× original media volume). The resulting cells were either lysed for analyzing the Gluc-Bio amount or re-suspended in PBS to measure the FDG content with a γ counter (1480 Wizard 3; Perkin Elmer).

Example 25

Fabrication of Single Cell Barcode Chip (SCBC) Devices

Figure 12:
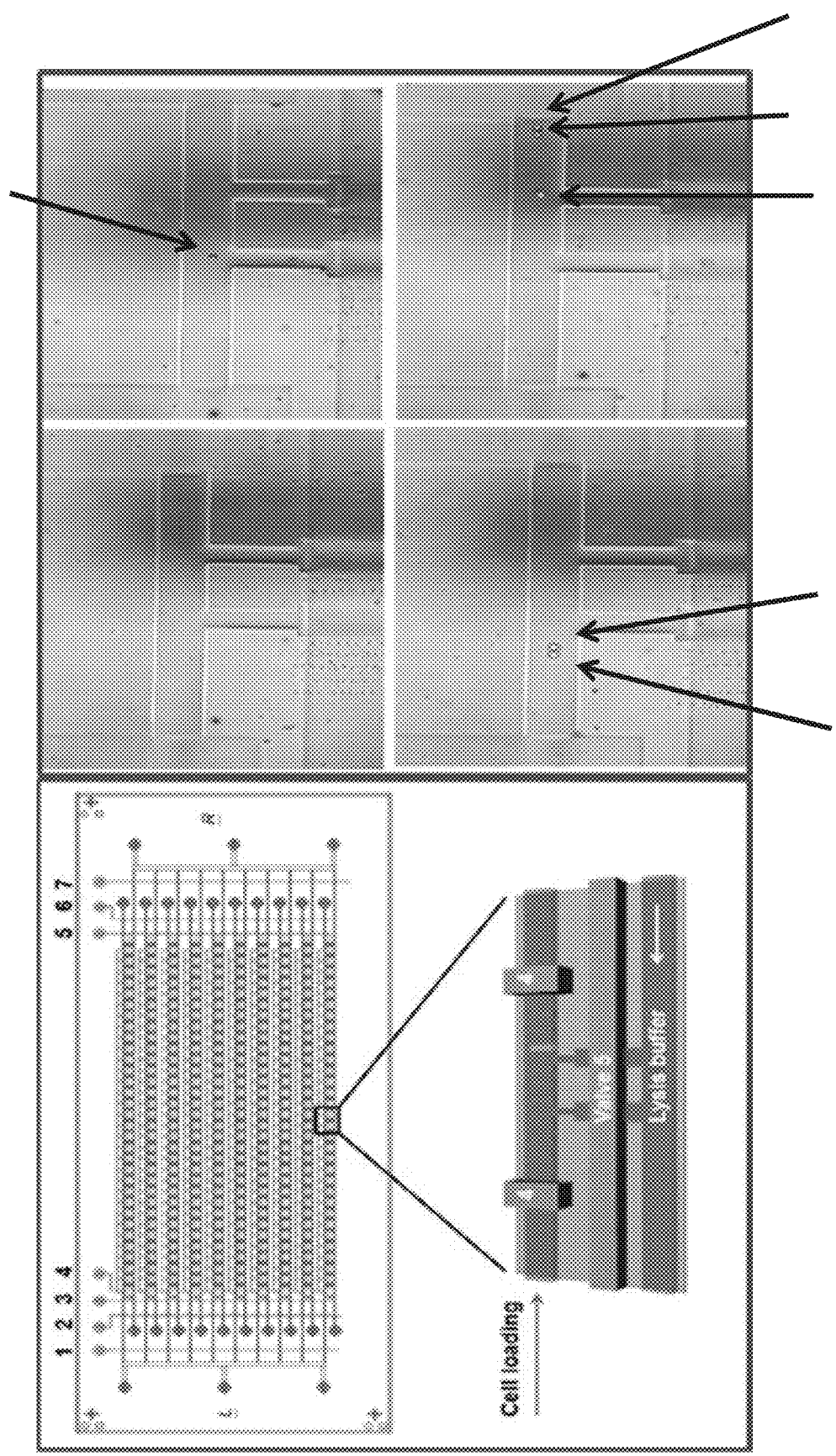
FIG. 12 on the left panel, shows a design illustration of the two-layered SCBC device with the annotations of the valves labeled on top; and on the right panel shows a microscopy image of individual cell chambers showing 0, 1, 2, and 3 cells trapped in the chambers as indicated by the black arrows, according to embodiments of the present invention.

The SCBC devices consist of DNA barcode microarray glass slides and PDMS slabs that contain microfluidic circuits. The DNA barcode slides were prepared through microchannel-guided flow patterning method as shown in FIG. 11. The PDMS slabs were fabricated using a two-layer soft lithography approach. The flow layer was fabricated by spin-casting Sylgard 184 (A:B=20:1) polymer mix onto a SPR 220 positive photoresist mold (16 um in height) at 2000 rpm for 1 min. The control layer was molded from a SU8 2025 negative photoresist master (40 um in height) using Sylgard 184 (A:B=7:1) polymer mix. These two parts were cured at 80° C. for 20 min, and the control layer was aligned onto the flow layer. The two-layer device was thermally treated at 80° C. (1.5 hr) and then released from the flow layer mold. After drilling the inlet/outlet holes from the PDMS, the slab was aligned onto the DNA barcode glass slides and treated at 80° C. (2 hr) to afford a fully assembled SCBC device. The layout of the SCBC device is illustrated in FIG. 12.

Example 26

Operation of the SCBC Devices

Conversion of the DNA barcodes to capture antibody microarrays. The control valve 5 (FIG. 12) was closed to separate the fluidic channels into upper and lower channels. The upper channels can be further compartmentalized into different operational units (microchambers), each of which was equipped with a full set of antibody barcode for cell trapping and analyte detection, while the lower ones were used as lysis buffer reservoir (FIG. 12). A cocktail of DNA-encoded antibody conjugates in a BSA solution (1.5% in PBS) was flown into the upper channels and incubated at 37° C. for 1 hr to convert the DNA barcodes into antibody microarrays. The unbound conjugates were then washed off by 1×PBST (Cell Signaling, 0.05% Tween 20) and the channels were then blocked with a BSA (1% in 1×PBST) solution for 1 hr.

Cell loading. The upper channels were briefly rinsed with cell culture medium to minimize perturbation to the cells. Simultaneously, GBM39 neurospheres were disassociated into single cells and incubated with Gluc-Bio and/or Ad-Glut (Compound 3). After washing to remove the excess Gluc-Bio and Ad-Glutamine, these single-cells were suspended in serum-free, biotin-free, glutamine-free media at a concentration of 106 cells/mL. The suspension was loaded into the SCBC device and compartmentalized into 310 isolated microchambers with single cell or defined number of cells in each chamber. The cell loading step results in a random distribution of different numbers of cells in different chambers, the statistical distribution can be adjusted by varying the loading concentration and the flow speed. In our experiment setup, each chip typically has around 100 zero-cell chambers, 100 single cell chambers and 100 chambers with more than 2 cells. This distribution is critical in terms of signal background subtraction and validation. The extra cells were washed away by 1×PBST. The images of each chamber were recorded using a microscope-CCD camera and used for subsequent cell counting.

On-chip cell lysis. A cell lysis buffer mixture was introduced into the lower channels and the whole device was placed on ice. Valve 5 was opened for 15 min to allow the lysis buffer to diffuse into individual cell chambers under a positive pressure. After closing valve 5, the device was incubated on ice for another 15 min to complete the on-chip cell lysis. The device was then incubated at room temperature with shaking for 2 hr to complete the capture of analytes by the antibody microarrays. After the incubation, the unbound cell lysate was quickly flushed away by 1×PBST.

Applying the detection cocktail. A cocktail of Alexa Fluor 647-labeled detection antibodies as well as the Biotin-BHQ2 probe were prepared in a BSA solution (1% in 1×PBST) and flown into the device for 60 min to develop the analytes captured into fluorescence signal.

Rinse and fluorescence readout. The channels were washed with 1×PBST for 30 min. The barcode slide was then peeled off from the PDMS slab, washed sequentially with 1×PBS, 0.5×PBS and Millipore water, dried by a VWR Miniarray microcentrifuge, and scanned by an Axon GenePix 4400A at laser power 80% (635 nm) and 15% (532 nm), and at 2.5 um/pixel resolution. Signals from two color channels were collected and digitized by the manufactures' software.

Example 27

Generation of Calibration Curves

The standard calibration of metabolites were performed using SCBC devices under the same conditions described above, except that known concentrations of metabolite solutions were loaded into the device instead of the cells. The fluorescence signals from the resulted barcode slides were collected to generate the calibration curves (FIG. 7A). These standard curves allow converting the relative fluorescence signal into copy number of analytes assayed, enabling absolute quantifications of the metabolites, under the condition that the same concentration of the competitors were employed in the experiments.

Example 28

Statistical Analysis

Figure 14A:
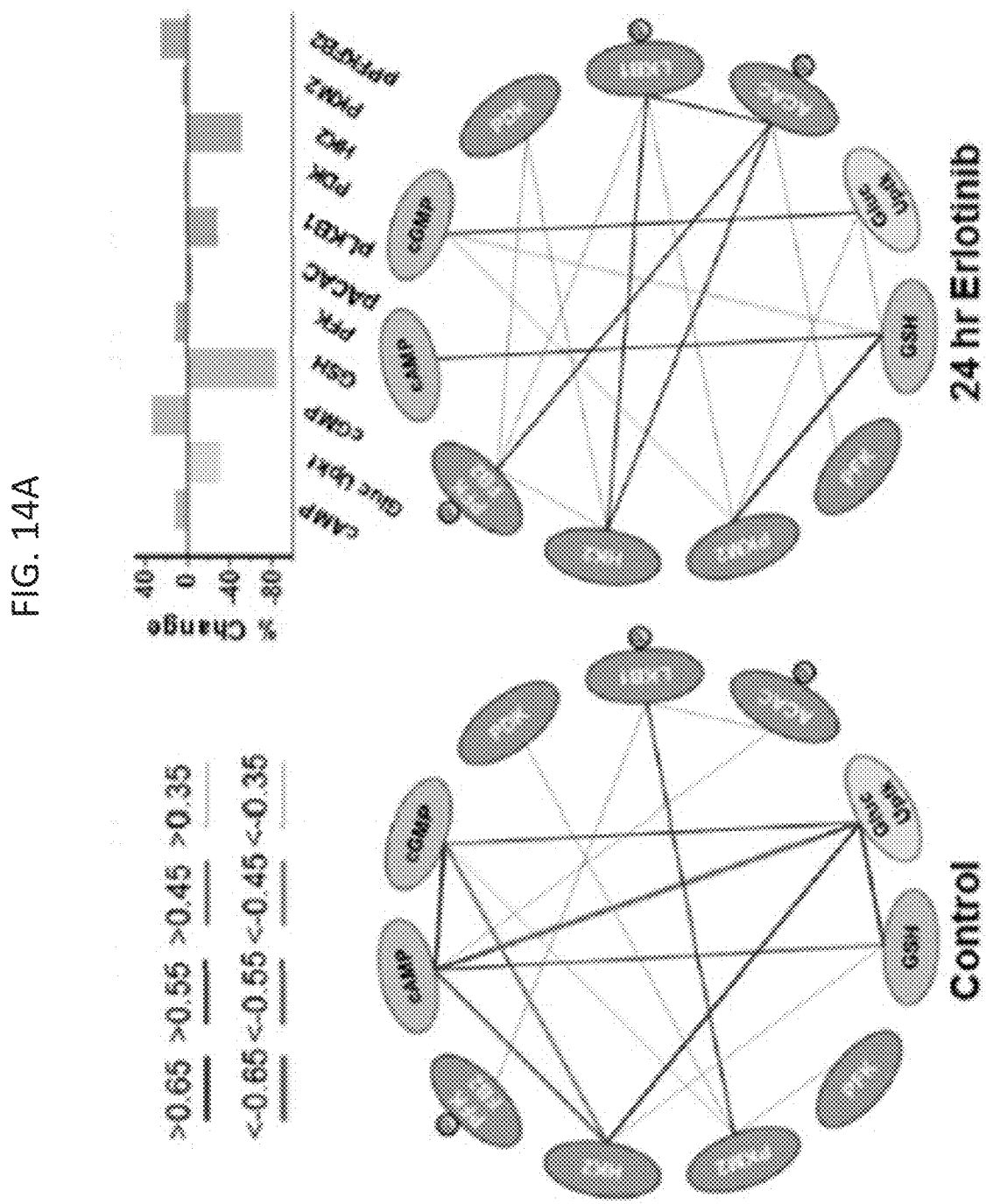
FIG. 14A shows correlation networks generated from the SCBC data set and the percent abundance changes of each of the analytes after 24 hours of erlotinib treatment, in which the cAMP, cGMP, and GSH values correspond to the absolute copy number changes based on the calibration curves, the data on the glucose uptake are shown as the changes of Gluc-Bio uptake amounts, and the protein data are based on the changes of fluorescence intensity according to embodiments of the present invention.
Figure 14B:
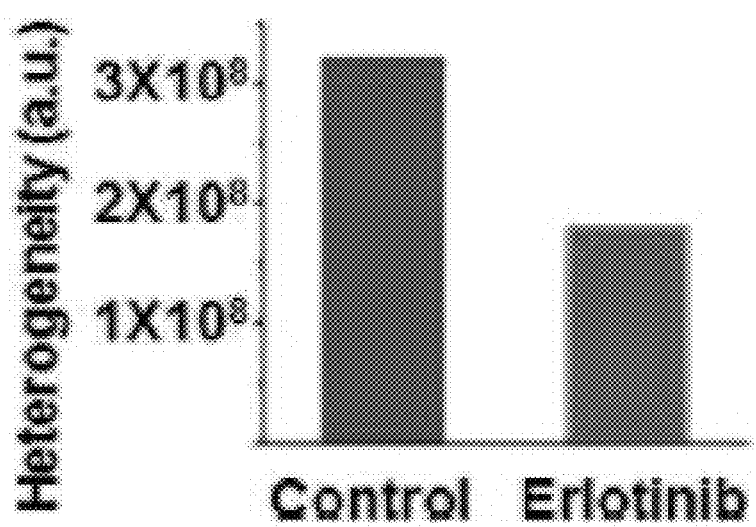
FIG. 14B is a graph showing the heterogeneity indices of the data sets, according to embodiments of the present invention.
Figure 16A:
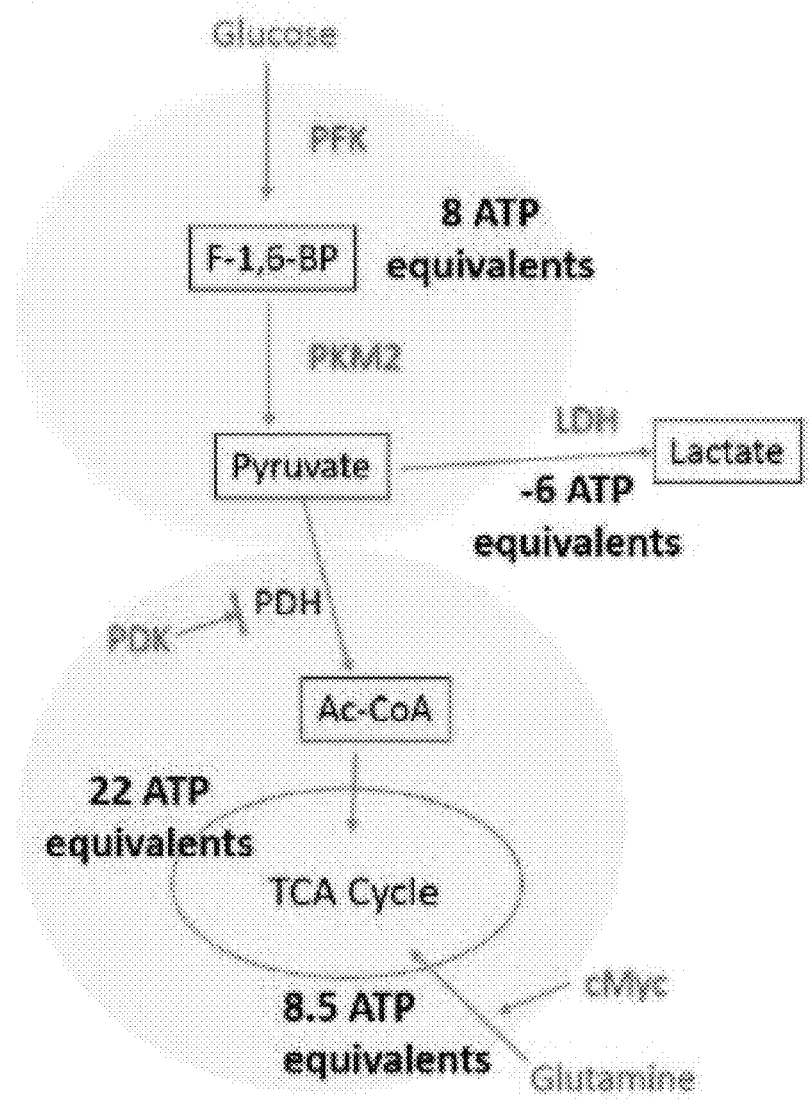
FIG. 16A is a schematic of a simplified metabolic model in which the production number of various high energy molecules (ATP, NADH, FADH$_2$, etc.) are converted to the production of ATP equivalents, according to embodiments of the present invention.
Figure 16B:
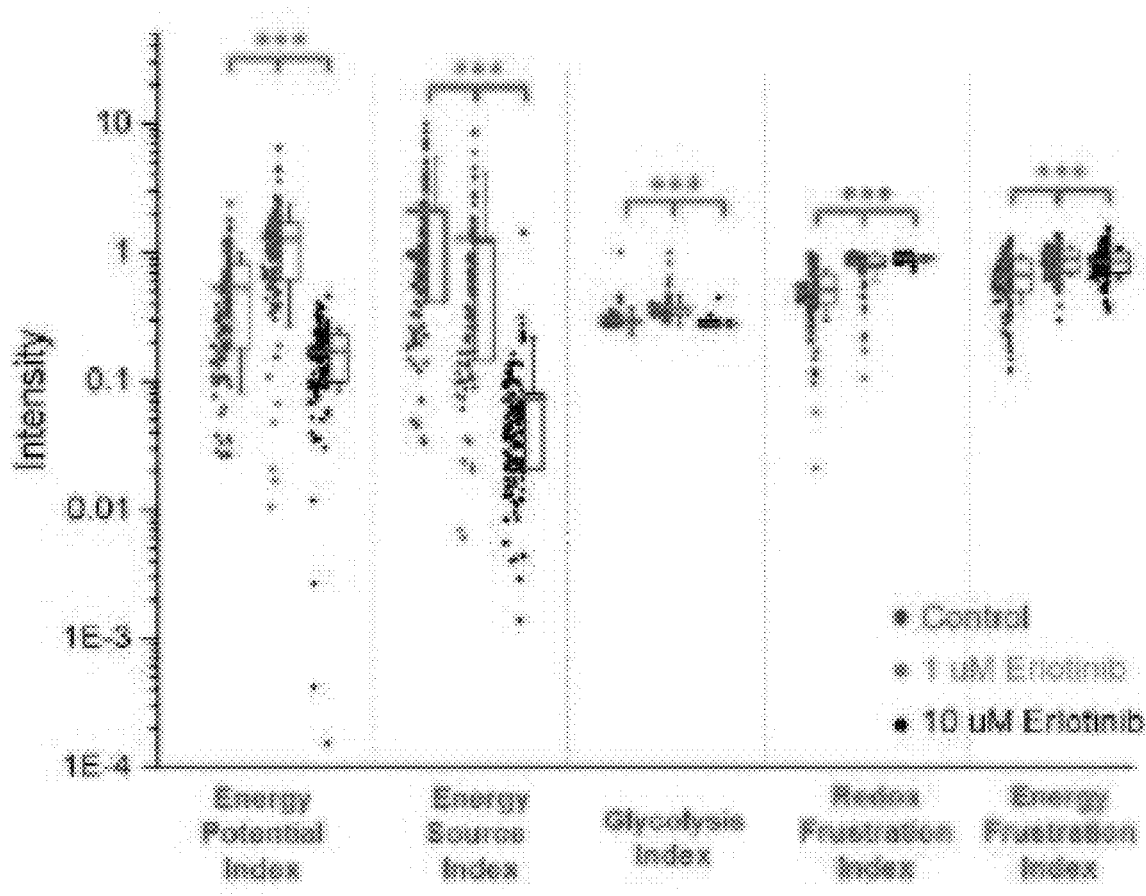
FIG. 16B shows scatter plots of the energy indices as defined below in corresponding colors, according to embodiments of the present invention.
Figure 16C:
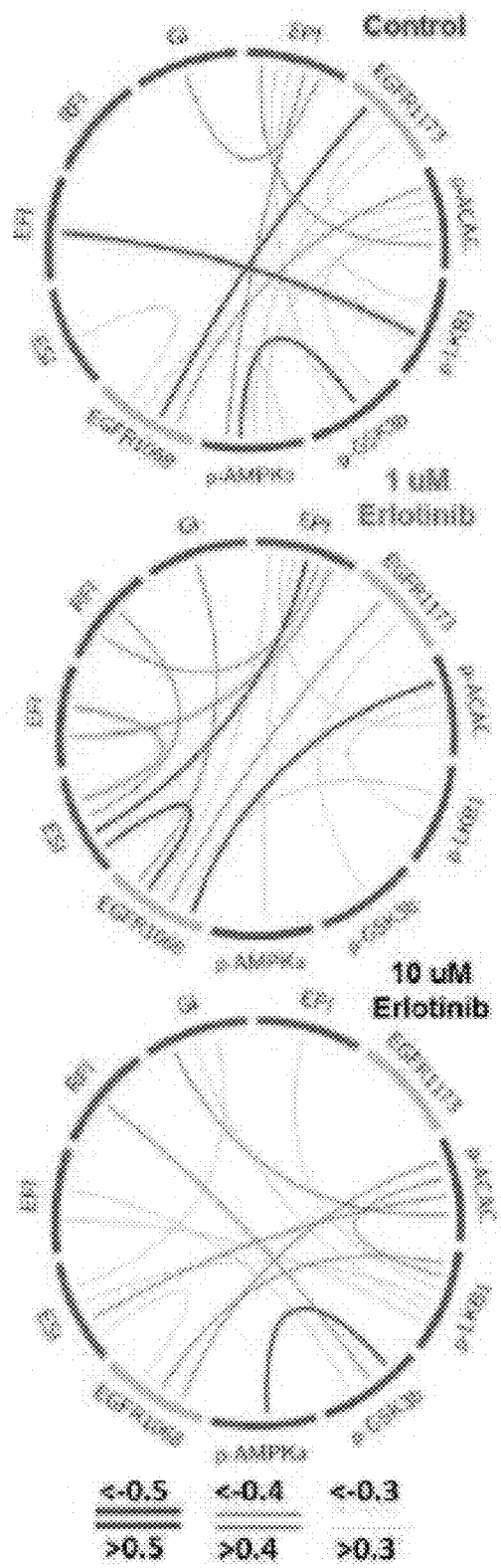
FIG. 16C shows the correlation networks for different samples, as indicated, according to embodiments of the present invention.
Figure 16D:
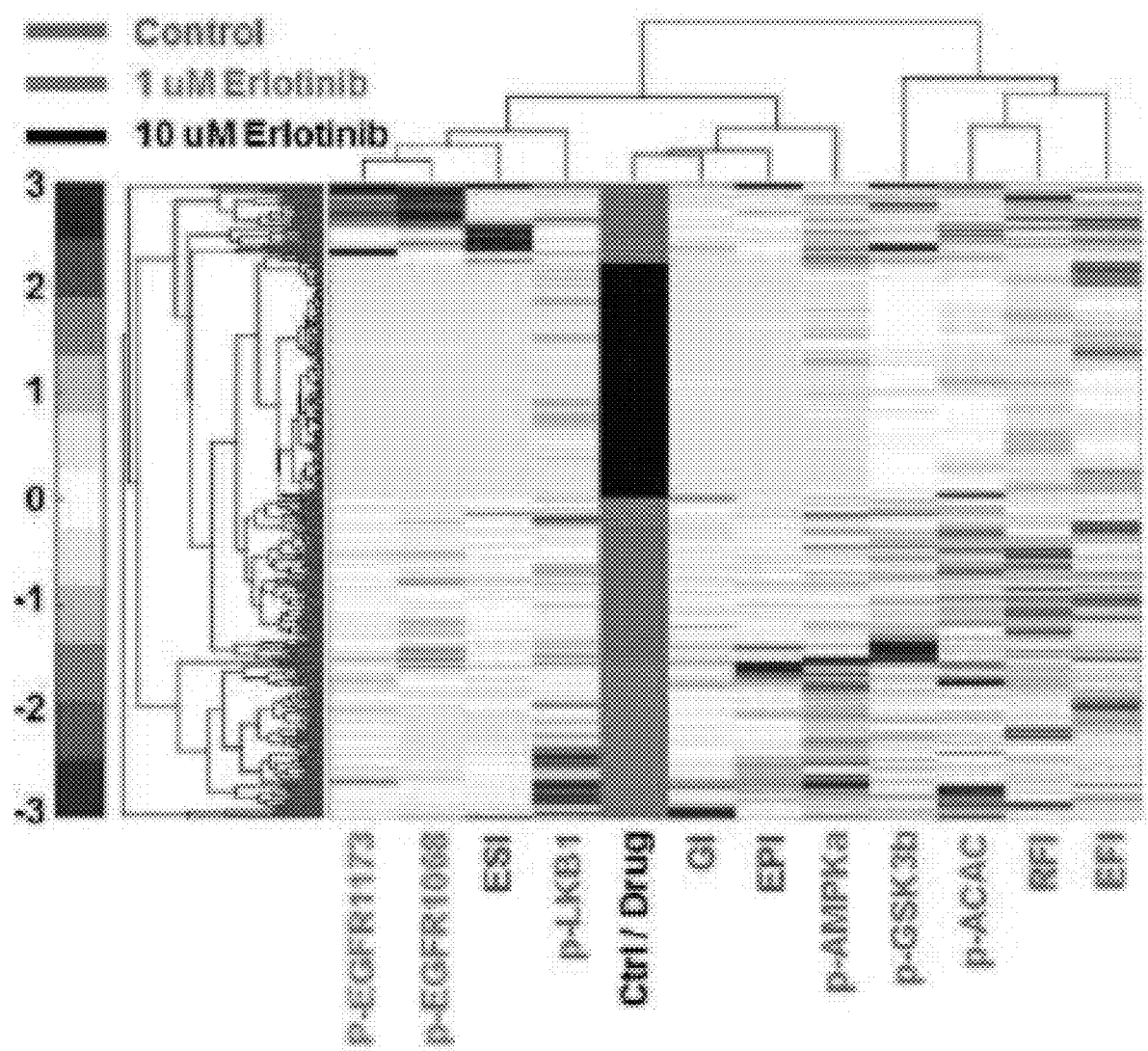
FIG. 16D is a heat map of the agglomerative hierarchical clustering analysis of the three treatment conditions showing that the differences between the control and 1 uM erlotinib treated cells are much smaller than those between 10 uM and 1 uM erlotinib samples, according to embodiments of the present invention.

The SCBC dataset is an m×n matrix table, each row (m) of which represents a specific microchamber address with a defined number of single cells and each column (n) represents the abundance of a specific analyte in those microchambers. Pairwise comparison was performed through Mann-Whitney method. The correlation coefficients were directly calculated from the dataset using Spearman's rank method. Bonferroni corrected p-value was used to define the statistical significance level for the entire panel and only significant ones are shown in the correlation network (FIGS. 14A-14B and 16C). Agglomerative hierarchical clustering analysis was carried out by XLSTAT software (Addinsoft) on the single cell dataset. Agglomerative hierarchical clustering analysis was carried out by Matlab software (Mathworks) on the combined single cell dataset using Euclidian distance and complete linkage. The proximity among single cell readouts was measured by the dissimilarity coefficients of Euclidian distance with Ward's minimum variance method. The calculated dissimilarity coefficients were employed to quantify the functional heterogeneity of the cells. The correlation network of FIG. 16C was drawn using Circos software with results presented as a heatmap (FIG. 16D).

Example 29

Cell Lysis Buffer Mixture Recipe Used in SCBC Measurements 400 uL of 10× cell lysis buffer (Cell Signaling), 20 uL of 100× protease/phosphatase inhibitor cocktail (Cell Signaling), 100 uL of 1.5% BSA/PBS, 3.3 uL cAMP-HRP (Genscript, 0.1 mg/mL), 4.4 uL cGMP-HRP (Genscript, 0.1 mg/mL), 1 uL of Alexa Fluor 555-labeled streptavidin (0.1 mg/mL) and 0.5 uL GSH-AF647 (22.6 uM in PBS), and 200 nM Adamantane-BHQ2.

Example 30

Validation of the Gluc-Bio Uptake

GBM39 single cells were suspended in normal media (17.5 mM glucose) or high glucose media (25 mM glucose)

at a concentration of 0.5 M cells/mL. These cells were incubated with 20 ug/mL of Gluc-Bio at 37° C. or 4° C. for 20 min. After incubation, cells were washed with cold PBS for three times and then lysed for quantifying the Gluc-Bio. The result is shown in FIG. 4C.

Example 31

Validation of the Gluc-Bio as a Substrate for Hexokinase

In order to verify that Gluc-Bio is a substrate for hexokinase, a coupled enzyme kinetics measurement method was employed. Enzymes and substrate solutions from a glucose assay kit (Sigma-Aldrich) were used without purification. FIG. 4D upper panel shows the two coupled enzymatic reactions. First, hexokinase converts glucose into glucose-6-phosphate, which consumes one equivalent of ATP. Then, the glucose-6-phosphate is converted to gluconate-6-phosphate by glucose-6-phosphate dehydrogenase (G6PDH). At the same time, this process converts NAD to NADH, which has a distinct absorption band at 340 nm. By continuously measuring the solution absorption, the kinetics of the first reaction can be indirectly monitored. If Gluc-Bio is a substrate for hexokinase, the product 2'-biotinyl-deoxyglucose-6-phosphate (Gluc-Bio-6P) cannot be further converted by G6PDH and therefore will not increase the NADH amount. This will result in a much slower generation of NADH. The lower left panel of FIG. 4D demonstrates that in the presence of Gluc-Bio, the generation of NADH is much slower than that of glucose alone. This proves that Gluc-Bio can bind to hexokinase and could be a substrate. However, this result cannot distinguish whether Gluc-Bio is a substrate or an inhibitor. In order to clarify this, another experiment was designed to prove that Gluc-Bio is a substrate. In this experiment, the amount of ATP was controlled to be much less than that of glucose. If Gluc-Bio is simply an inhibitor and cannot be converted by hexokinase, it will not consume the ATP pool in the solution, and the final amount of NADH will be the same as that of glucose alone. The lower right panel of FIG. 4D shows that with the addition of Gluc-Bio, less NADH was generated. This proves that Gluc-Bio consumes ATP and therefore is a substrate for hexokinase.

Example 32

PET/CT Methods

Figure 13A:
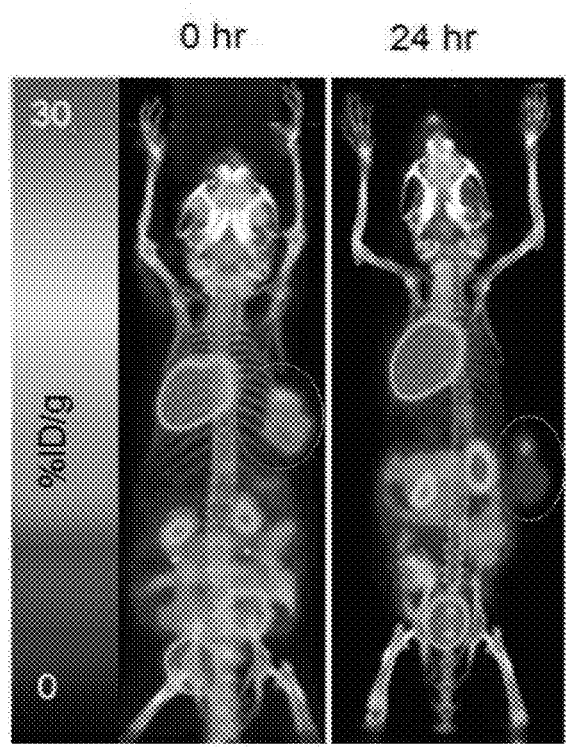
FIG. 13A are representative $^{18}$F-FDG PET/CT images of GBM39 subcutaneous tumor bearing mice at 0 or 24 hours a indicated, post treatment with erlotinib (50 m/kg, n=4 mice) for 24 hours, according to embodiments of the present invention.
Figure 13B:
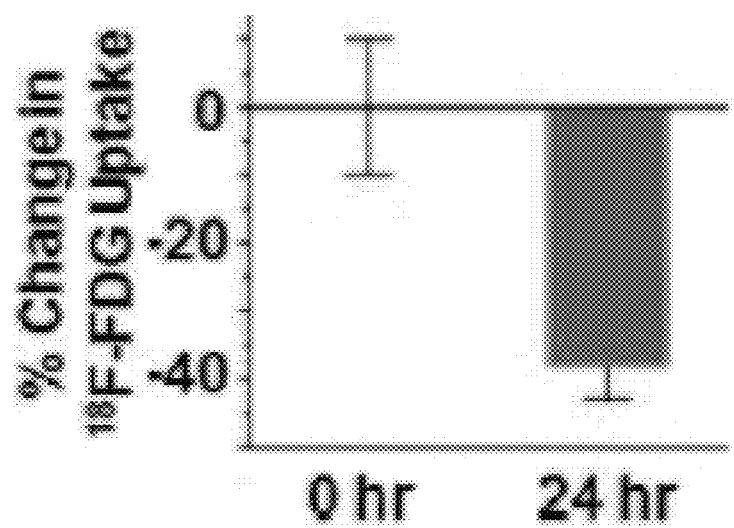
FIG. 13B is a graph of the amount (%) change in $^{18}$F-FDG uptake in vivo from the tumor sites of GBM39-bearing mice of FIG. 13A, according to embodiments of the present invention.

Mice kept warm under gas anesthesia (2% isoflurane) were injected intraperitoneally with $^{18}$F-FDG (20 μCi) and microPET scans were acquired for 10 minutes on the Genisys4 bench-top PET scanner (Sofie Biosciences). CT images were acquired the MicroCAT II CT system (Siemens) PET data are reconstructed into multiple frames using a statistical maximum a posteriori probability algorithm (MAP) (FIGS. 13A, 13B). CT (MicroCAT) images are at low dose 400 μm resolution acquisition with 200 μm voxel size. PET and CT images are co-registered as previously described (Nathanson, D. A.; et al. J. Exp. Med. 2014, 211, 473-486, the entire content of which is herein incorporated by reference).

Example 33

MicroPET Data Analysis

Following MAP reconstruction, regions of interest (ROI) of were defined, both over tumors and the background, on the reconstructed images. ROI values were determined by normalization to the total radioactivity injected per body weight (% ID/g) to give the standardized uptake value (SUV).

Example 34

Correlation Networks

The SCBC dataset of FIG. 8A provides 3 independent sets of observables, including the average analyte levels, the variances in distributions of those levels, and the correlations (or anti-correlations) between any two analytes (FIG. 14A). For example, an average analyte level may be comparable before and after the drug perturbation in GBM39, while the statistical distributions could be altered (e.g. PKM2). Similarly, the levels of 2 uncorrelated proteins may be repressed by a drug, but the correlations between those proteins may increase (e.g. p-ACAC and HK2). Collectively, these three observables may be associated with the heterogeneity of cellular responses. For example, the identification of metabolic outliers or distinct metabolic phenotypes might provide clues for identifying cell populations with differential responses to drugging. In the untreated sample, strong correlations were identified between cAMP and cGMP, between glucose uptake and HK2, and between glucose uptake and GSH. Additionally, the disappearance of positive correlations between PDK and PKM2 in the treated sample implies a reduction of glycolysis, presumably due to the down regulation of p-Akt under erlotinib treatment. These observations are consistent with the literature, and provide a validation of the platform.

Figure 15:
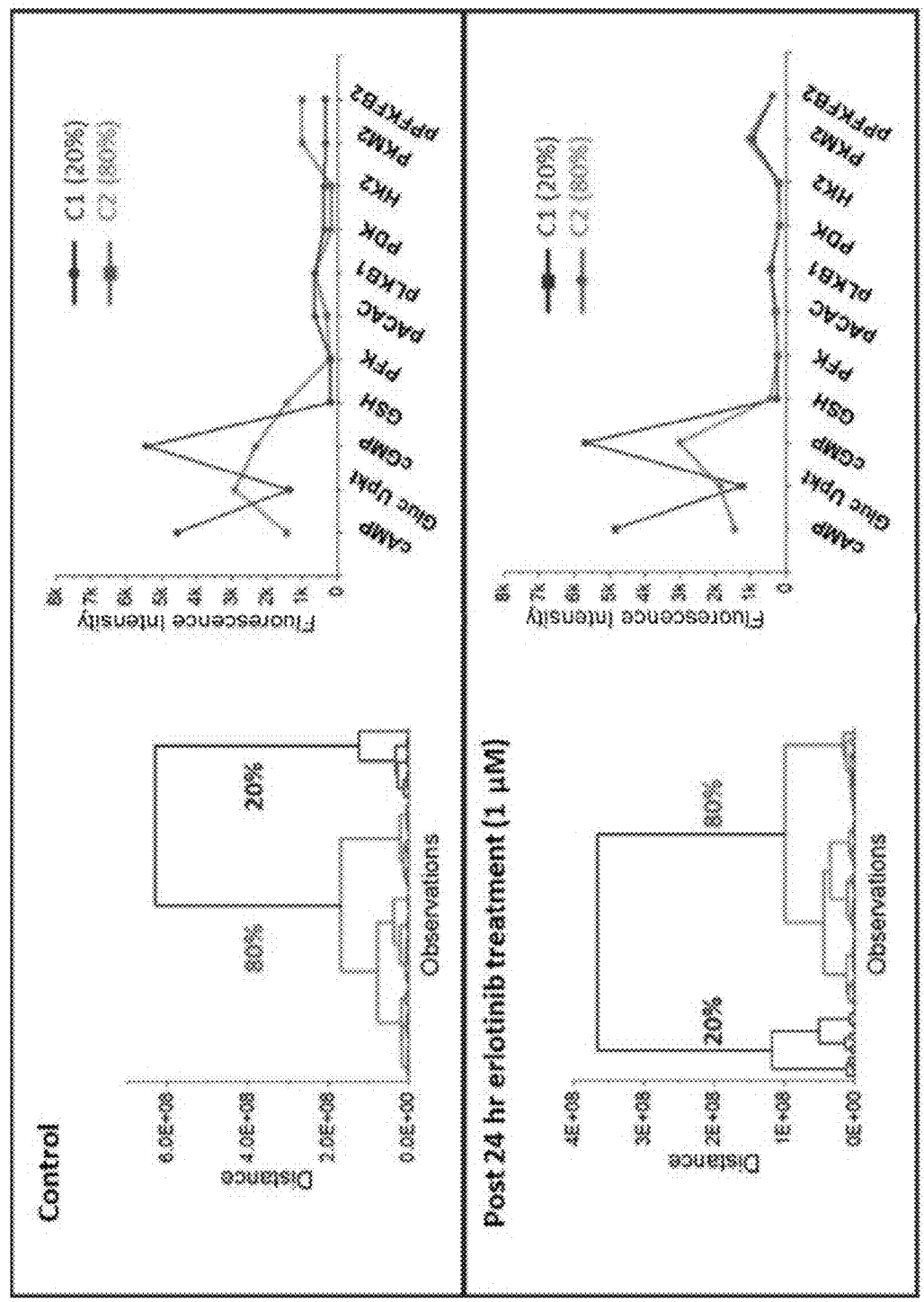
FIG. 15 in the upper left panel shows unsupervised clustering of SCBC data collected from GBM39 neurosphere tumor models before treatment with EGFR inhibitor with the upper right panel showing the analyte profile for the cell population; and the lower left panel shows unsupervised clustering of SCBC data collected from the GBM39 neurosphere tumor models after treatment with EGFR inhibitor, with the lower right panel showing the analyte profile for the cell population, according to embodiments of the present invention.

Anti-correlations are more difficult to identify using bulk assays, but are clearly resolved between the second messengers cAMP, cGMP and both glucose uptake and HK2. In fact, an unsupervised clustering analysis of the entire SCBC data set for the untreated GBM39 resolves that two metabolic phenotypes dominate the measured cellular heterogeneity (FIG. 14B): 80% of the cells exhibit high glucose uptake and low cAMP and cGMP, while 20% of the cells exhibit high cAMP and cGMP, but low glucose uptake (FIG. 15, upper panel). Following 24 h erlotinib treatment, the levels of glucose uptake and GSH, as well as the activities of HK2 were sharply reduced (FIG. 14A), however the same two metabolic phenotypes, corresponding to the same fractions of the total population, are still resolved (FIG. 15, lower panel).

Example 35

Simplified Metabolic Model

Figure 16E:
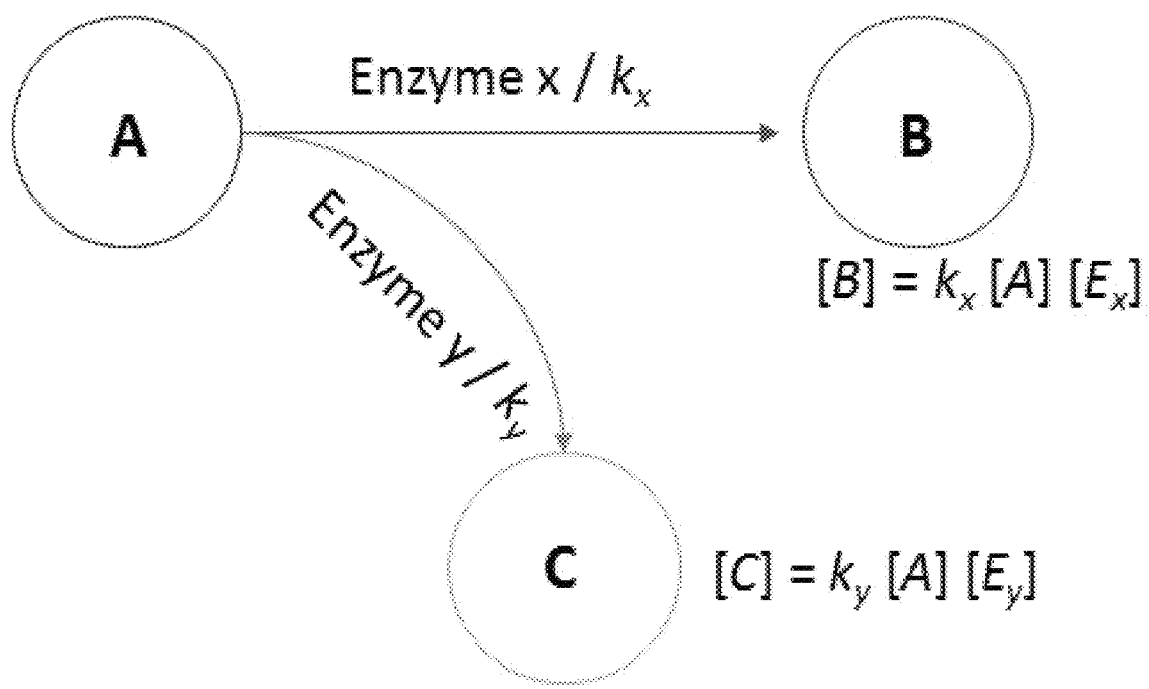
FIG. 16E is a steady state kinetic model, in which under steady state approximation, $[B]=k_x[A][E_x]$ and $[C]=k_y[A][E_y]$; a semi quantitative sample comparison is shown in which $\alpha$ is the multi-sample normalized activity coefficient, ranging (0,1) according to embodiments of the present invention.

In order to better understand the integrated single cell metabolic/proteomic data, a simplified semi-quantitative metabolic model (FIG. 16A) was developed. The focus of this model includes the glycolysis pathway and the TCA cycle, which cover the major contributors of cellular energy generation. Glucose is used by cells for many tasks, but by combining the measurement of glucose uptake with measurements of those enzymes that process glucose for energy production and lactate production, an estimation may be made of the contributions of glucose to glycolysis and to the TCA cycle (FIGS. 16A-16B). It assumed that each glucose molecule consumed yields 8 ATP equivalents through glycolysis, and an additional 22 ATP equivalents through the TCA cycle. The numbers here are not the actual ATP production number, but an energy-currency conversion. The glycolysis part generates 2 ATP and 2 NADH molecules per glucose, and each NADH is ultimately worth 3 ATP, thus making 8 ATP total. Similar treatments are applied to the TCA cycle to obtain ATP numbers. For glutamine that is taken up by the cell, there are multiple possible outcomes. It can enter the TCA cycle to generate energy, or it can be exported in exchange for other amino acids, or participate in biosynthesis of glutathione and proteins, as examples. On this basis, glutamine may be considered as a special currency, which can either be used directly by the cell to produce energy, or in exchange of other necessary nutrients or to perform some crucial metabolic function. From a global point of view, the active uptake of glutamine reflects a metabolic demand from the cell, regardless how it is used. In order to have an integrated picture of the potential energy production from glutamine and glucose, we simply assume that all glutamine participates in the TCA cycle, so that each glutamine molecule affords 8.5 ATP equivalents. To calculate the energy production for each pathway, glucose and glutamine uptake levels as well as related metabolic enzyme levels are normalized into the range between 0 and 1 across all samples. Subsequently, the normalized analyte levels (a) were used and a steady-state approximation (FIG. 16E) to calculate the energy production rate for each step (FIG. 16B). Several energy indices were defined based on the model. The energy production index (EPI) assesses the total energy production rate through glucose and glutamine metabolism, while the energy source index (ESI) measures the energy contribution ratio between glucose and glutamine. The glycolysis index (GI) weighs the contribution of glycolysis in total glucose-based energy production, and depends upon glucose uptake, as well as the levels of phosphofructokinase (PFK) and pyruvate kinase isozyme M2 (PKM2). In addition to the energy indices, we use the cAMP and cGMP levels to define an energy frustration index (EFI), and use the GSH level to define a redox frustration index (RFI).

The calculated indices provided a functional assessment of how the cellular heterogeneity is altered by drugging. FIG. 16B shows the scatter plot of the indices. Both the GI and the EPI increased upon 1 µM erlotinib treatment. Even though glucose uptake is repressed, the levels of PFK and PKM2 are increased by the drug, implying a more efficient use for energy production of the glucose that is taken up. Glutamine uptake is increased at 1 uM dosing. Both glucose and glutamine uptake are decreased for the higher dose Erlotinib treatment. The implication is that low dose Erlotinib induced a higher energy production rate in cells, as those cells adapt to the repressed p-EGFR levels. A consequence is that the cells become more glycolytic, in spite of repressed glucose uptake. On the other hand, higher drug concentration inhibits cellular energy production and the cells become less glycolytic. The ESI dropped as drug concentration was increased, suggesting that higher drug concentration increases the cellular dependency on glutamine metabolism. Both the EFI and RFI values increase upon drug treatment, providing validation of these indices as measures of cellular stress.

Multiplex single cell assays also permit direct extraction of analyte-analyte correlations. FIG. 16C displays the correlation networks for each sample. Both low and high dose drug treatments clearly induced significant changes within the correlation networks. In the control sample, there is a strong correlation between EGFR1068 and EGFR1173, which is consistent with existing knowledge of EGFR signaling. There are also correlations between the ESI and the p-EGFR levels that point to a relationship between EGFR signaling and cellular glutamine dependence—cells with higher p-EGFR levels are less dependent on glutamine. The possible implication is that the upstream signaling of EGFR plays a strong role in determining cellular glutamine dependency.

Multiplex single cell measurements of functional analytes (metabolites and enzymes) yield several classes of information, in addition to the average value of the analyte (which is also obtained from bulk assays). First, the distribution of each analyte level provides insight into the sample heterogeneity. Second, analyte-analyte correlations may provide information regarding signaling interactions that are activated or repressed between different experimental conditions. Finally, clustering analysis can provide a more global view for the statistical analysis of sets of analytes, or permit comparisons across different experimental conditions. In this disclosure, the inclusion of metabolites with intrinsically correlated metabolic proteins within the panel permits the use of a semi-quantitative physical chemistry model for guiding the interpretation of the single cell data. Indeed, the metabolic model of FIG. 16A is simplified, and excludes many other metabolic pathways that may be active. However, within the limited context of global cellular energy demand, the model should have meaning.

Figure 17:
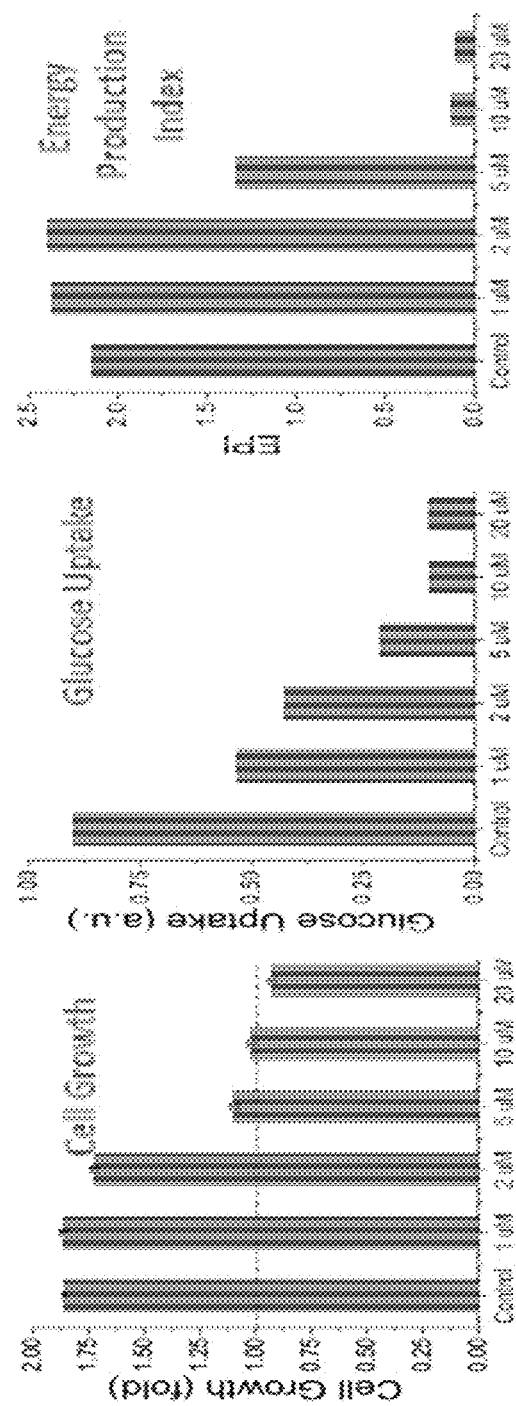
FIG. 17 shows graphs of Cell Growth, Glucose Uptake, and Energy Production Index (EPI) for cells treated with different concentrations of erlotinib as indicated for 24 hours, according to embodiments of the present invention.

The metabolic model yields energy indices that do, in fact, help guide the data analysis from the measurements of the dose-dependent response of the GBM cells to erlotinib (FIG. 16B). For example, the energy production index (EPI) increases upon low dose drug treatment. This is in seeming contrast to the decreased glucose uptake, but the EPI provides a more global view of energy flux. The increased level of metabolic enzymes and the heightened glutamine uptake elevated the total metabolic activities of the cells under drug stress. At the higher dose, erlotinib treatment repressed both the metabolic enzymes and the glutamine uptake, which brought down the EPI values. This result has strong clinical relevance. In the case of low dose drug treatment, even though the drug has successfully engaged its target (decreased p-EGFR level) and the glucose metabolism is inhibited (corresponding to a decreased $^{18}$F-FDG PET signal in clinical molecular imaging), the cells are still very metabolically active, and the cell growth is not inhibited, thus leading to a poor patient response. Thus, the EPI values provide a better indicator of the drug effectiveness than functional protein assays and/or glucose uptake assays alone. This can also been confirmed from the clustering analysis (FIG. 16D), where EPI values successfully differentiate control/low dose drug/high dose drug populations and correspond well with the cell survival. Additional experiments also show that EPI is a good indicator for cell proliferation capabilities at bulk level (FIG. 17).

The metabolic model is also capable of providing deeper biological information from the dataset. For instance, a linkage between receptor tyrosine kinase signaling and GBM cell metabolism is resolved. It was found that ESI appears to be highly correlated with the p-EGFR level of the cells (FIG. 16D), while no single metabolite or metabolic protein exhibited such a strong correlation. The model-based analysis thus suggests that EGFR signaling possibly regulates the glutamine dependence in these cells. Additionally, the EGFR1068 site remains active upon drug treatment, while the EGFR1173 site decouples from the correlation network. This has not been previously observed, and one may infer different functional consequences of the two EGFR phosphorylation sites, with the pEGFR1068 possibly playing a role in regulating cellular glutamine dependency, and thus cell survival upon erlotinib treatment. This information may be useful in terms of understanding the rapid development of resistance to erlotinib that is seen in GBM patients.

The metabolic protein panel and the metabolic model were established to assess the contribution of glucose and glutamine to the energy production through glycolysis and the TCA cycle.

Figure 9A:
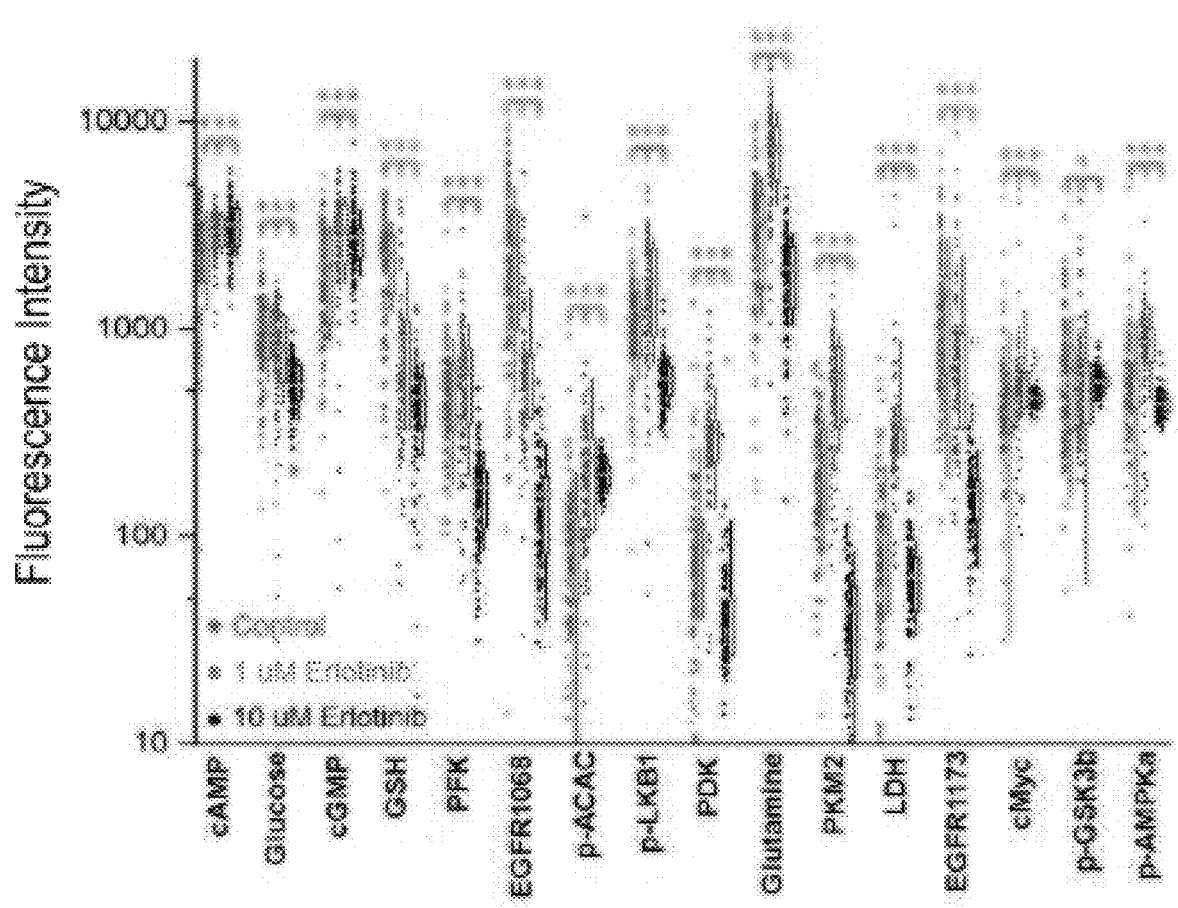
FIG. 9A shows metabolite and protein fluorescence data simultaneously assayed in U87EGFRvIII cells using a single cell barcode chip (SCBC) patterned to detect cAMP, Gluc-Bio, cGMP, GSH, and Ad-Glutamine metabolites using immunofluorescence assays as shown in FIGS. 2A-2C and metabolism-related proteins and phosphoproteins including phosphofructokinase (PFK), phospho-acetyl-CoA Caraboxylase (pACAC), phospho-liver kinase B1 (pLKB1), phosphoinositide-dependent kinase 1 (PDK), hexokinase 2 (HK2), pyruvate kinase M2 (PKM2), and phospho-carbohydrate kinase family protein (pPFKB2), lactate dehydrogenase (LDH), cMyc, phospho-glycogen synthase kinase 3b (GSK3b), and phospho-adenosine monophosphate dependent kinase a (pAMPKa) in the absence (control)(light purple) or presence of 1 μM erlotinib (green) or 10 μm erlotinib (dark purple) in which both 1 μM and 10 μM erlotinib-suppressed phosphorylation of EGFR at two phosphorylation sites (Y1168 and Y1173), as shown; with red horizontal denoting the mean fluorescence value of the measured analyte, the boxes cover the second and the third sample quartiles and the whiskers label the standard deviation ($*$, $p<0.1$; $***$, $p<0.001$), according to embodiments of the present invention.
Figure 9B:
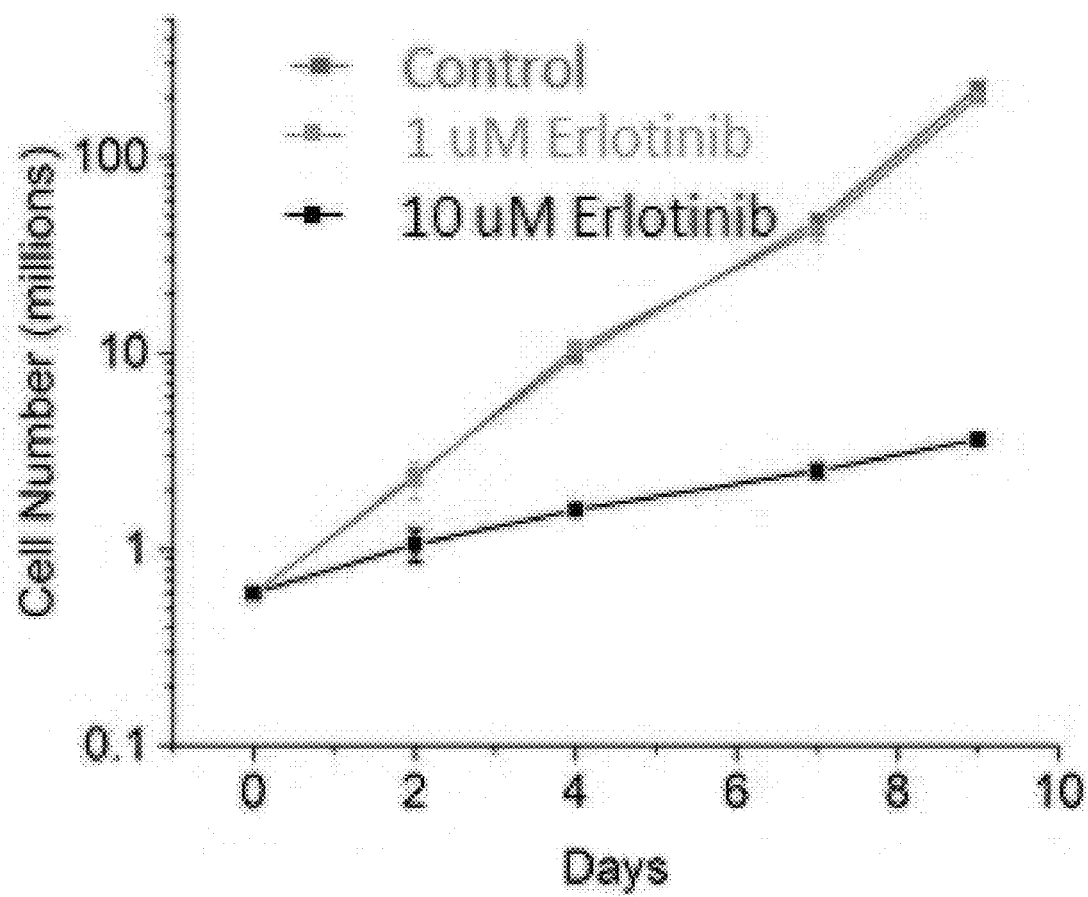
FIG. 9B is graph of growth curves of measuring the number of U87EGFRvIII cells as a function of days in the absence (control)(purple) or presence of 1 uM erlotinib (green) or 10 uM erlotinib (black), in which 1 uM erlotinib does not inhibit, according to embodiments of the present invention.

As disclosed throughout, for example in FIGS. 2A-2E, immunofluorescence assays are disclosed for assaying the metabolites cAMP, cGMP, glutathione, glucose uptake, and glutamine uptake. These metabolic assays may be incorporated into proteomic arrays, as exemplified in FIGS. 8A and 9A allowing for simultaneous quantification of metabolites and proteins in a single cell.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A metabolite and protein quantifying method configured for quantifying metabolites and proteins of single cells, the method comprising:
   (a) a first incubation comprising incubating a plurality of single cells with at least one labeled metabolite to form a cell assay mixture;
   (b) loading the cell assay mixture after the first incubation into a probe-bound array chip (PBAC), the PBAC comprising:
      a first layer including a glass surface having immobilized thereon capture probes comprising at least one metabolite capture probe and at least one protein capture probe, wherein the capture probes are configured to form a spatially-addressable barcode on the PBAC; and
      a second layer coupled to the first layer and including a plurality of chambers,
      wherein loading the cell assay mixture into the PBAC is such that at least some individual chambers of the plurality of chambers receive only a single cell of the plurality of cells;
   (c) lysing each cell to form a lysed cell assay mixture in each chamber;
   (d) a second incubation comprising incubating the lysed cell assay mixture in each chamber;
   (e) first quantifying of an amount of labeled metabolites bound to the at least one metabolite capture probe so as to determine a level of the at least one metabolite based thereon; and
   (f) second quantifying of an amount of at least one protein bound to the at least one protein capture probe to determine the concentration of the at least one protein, wherein the at least one metabolite is selected from the group consisting of cyclic adenosine monophosphate (cAMP), cyclic guanine monophosphate (cGMP), glutathione, glucose, and glutamine.

2. The method of claim 1, wherein the labeled metabolite is selected from the group consisting of cAMP-horseradish peroxidase (cAMP-HRP), cGMP-horseradish peroxidase (cGMP-HRP), glutathione-fluorescent dye, cAMP-fluorescent dye, cGMP-fluorescent dye, glutathione-HRP, glucose-biotin, glutamine-adamantine, glucose-adamantane, and combinations thereof.

3. The method of claim 1, wherein the metabolite capture probe is selected from the group consisting of anti-cAMP antibody, anti-cGMP antibody, anti-glutathione antibody, streptavidin, cyclodextrin, and combinations thereof.

4. The method of claim 1, wherein:
   the glass surface includes at least two metabolite capture probes, and when at least one of at least two metabolites is glucose or glutamine, the first incubation further comprises incubating the cell with a medium comprising a glucose analog or a glutamine analog; and
   removing the medium prior to lysing.

5. The method of claim 4, wherein the glucose analog is selected from glucose-biotin or glucose-adamantane.

6. The method of claim 4, wherein the glutamine analog is glutamine-adamantane.

7. The method of claim 1, wherein the first quantifying comprises analyzing by Förster resonance energy transfer (FRET) analysis.

8. The method of claim 1, wherein the first quantifying comprises using a BHQ2 quenching group.

9. The method of claim 8, wherein the BHQ2 quenching group is biotin-BHQ2 or adamantane-BHQ2.

10. The method of claim 1, wherein:
the glass surface includes at least two metabolite capture probes, and when one of at least two metabolites which bind to the at least two metabolite capture probes is selected from the group consisting of cAMP, cGMP, glutathione, and combinations thereof, the method further comprises immobilizing a metabolite capture probe configured to bind with one metabolite in labeled and unlabeled forms to the array chip;
during the first incubation, the at least two metabolites comprise a calculated amount;
and
determining the level of each of the at least two metabolites comprises determining a concentration of a respective metabolite in a single cell as the inverse of the amount of the quantified amount of the respective labeled metabolites bound to the respective metabolite capture probes.

11. The method of claim 1, wherein the at least one protein comprises a phosphoprotein.

12. The method of claim 11, wherein the at least one protein is selected from the group consisting of phospho-fructokinase (PFK), phospho-acetyl-CoA carboxylase (pACAC), phospho-liver kinase B1 (pLKB1), phosphoinositide-dependent kinase 1 (PDK), hexokinase 2 (HK2), pyruvate kinase M2 (PKM2), and phospho-carbohydrate kinase family protein (pPFKB2), lactate dehydrogenase (LDH), cMyc, phospho-glycogen synthase kinase 3b (GSK3b), phospho-adenosine monophosphate dependent kinase a (pAMPKa), and combinations thereof.

13. The method of claim 1, wherein the first quantifying and the second quantifying occur simultaneously.

14. The method of claim 1, wherein the first incubation comprises incubating the plurality of single cells with at least two labeled metabolites to form the cell assay mixture.

15. The method of claim 14, wherein the glass surface has immobilized thereon at least:
two metabolite capture probes, and/or
at least two protein capture probes,
and
the capture probes are configured to form the spatially-addressable barcode on the PBAC.

* * * * *

SEQUENCE LISTING

```
<160> NUMBER OF SEQ ID NOS: 22

<210> SEQ ID NO 1
<211> LENGTH: 30
<212> TYPE: DNA
<213> ORGANISM: Artificial Sequence
<220> FEATURE:
<223> OTHER INFORMATION: B ssDNA

<400> SEQUENCE: 1
aaaaaaaaaa gcctcattga atcatgccta                                       30

<210> SEQ ID NO 2
<211> LENGTH: 30
<212> TYPE: DNA
<213> ORGANISM: Artificial Sequence
<220> FEATURE:
<223> OTHER INFORMATION: B' ssDNA

<400> SEQUENCE: 2
aaaaaaaaaa taggcatgat tcaatgaggc                                       30

<210> SEQ ID NO 3
<211> LENGTH: 30
<212> TYPE: DNA
<213> ORGANISM: Artificial Sequence
<220> FEATURE:
<223> OTHER INFORMATION: C ssDNA

<400> SEQUENCE: 3
aaaaaaaaaa gcactcgtct actatcgcta                                       30

<210> SEQ ID NO 4
<211> LENGTH: 30
<212> TYPE: DNA
<213> ORGANISM: Artificial Sequence
<220> FEATURE:
<223> OTHER INFORMATION: C' ssDNA

<400> SEQUENCE: 4
aaaaaaaaaa tagcgatagt agacgagtgc                                       30

<210> SEQ ID NO 5
<211> LENGTH: 30
<212> TYPE: DNA
<213> ORGANISM: Artificial Sequence
<220> FEATURE:
<223> OTHER INFORMATION: D ssDNA

<400> SEQUENCE: 5
aaaaaaaaaa atggtcgaga tgtcagagta                                       30

<210> SEQ ID NO 6
<211> LENGTH: 30
<212> TYPE: DNA
<213> ORGANISM: Artificial Sequence
```

```
<220> FEATURE:
<223> OTHER INFORMATION: D' ssDNA

<400> SEQUENCE: 6
aaaaaaaaaa tactctgaca tctcgaccat                                    30

<210> SEQ ID NO 7
<211> LENGTH: 30
<212> TYPE: DNA
<213> ORGANISM: Artificial Sequence
<220> FEATURE:
<223> OTHER INFORMATION: E ssDNA

<400> SEQUENCE: 7
aaaaaaaaaa atgtgaagtg gcagtatcta                                    30

<210> SEQ ID NO 8
<211> LENGTH: 30
<212> TYPE: DNA
<213> ORGANISM: Artificial Sequence
<220> FEATURE:
<223> OTHER INFORMATION: E' ssDNA

<400> SEQUENCE: 8
aaaaaaaaaa tagatactgc cacttcacat                                    30

<210> SEQ ID NO 9
<211> LENGTH: 30
<212> TYPE: DNA
<213> ORGANISM: Artificial Sequence
<220> FEATURE:
<223> OTHER INFORMATION: F ssDNA

<400> SEQUENCE: 9
aaaaaaaaaa atcaggtaag gttcacggta                                    30

<210> SEQ ID NO 10
<211> LENGTH: 30
<212> TYPE: DNA
<213> ORGANISM: Artificial Sequence
<220> FEATURE:
<223> OTHER INFORMATION: F' ssDNA

<400> SEQUENCE: 10
aaaaaaaaaa taccgtgaac cttacctgat                                    30

<210> SEQ ID NO 11
<211> LENGTH: 30
<212> TYPE: DNA
<213> ORGANISM: Artificial Sequence
<220> FEATURE:
<223> OTHER INFORMATION: H ssDNA

<400> SEQUENCE: 11
aaaaaaaaaa attgaccaaa ctgcggtgcg                                    30

<210> SEQ ID NO 12
<211> LENGTH: 30
<212> TYPE: DNA
<213> ORGANISM: Artificial Sequence
<220> FEATURE:
<223> OTHER INFORMATION: H' ssDNA

<400> SEQUENCE: 12
aaaaaaaaaa cgcaccgcag tttggtcaat                                    30
```

```
<210> SEQ ID NO 13
<211> LENGTH: 30
<212> TYPE: DNA
<213> ORGANISM: Artificial Sequence
<220> FEATURE:
<223> OTHER INFORMATION: I ssDNA

<400> SEQUENCE: 13
aaaaaaaaaa tgccctattg ttgcgtcgga                                    30

<210> SEQ ID NO 14
<211> LENGTH: 30
<212> TYPE: DNA
<213> ORGANISM: Artificial Sequence
<220> FEATURE:
<223> OTHER INFORMATION: I' ssDNA

<400> SEQUENCE: 14
aaaaaaaaaa tccgacgcaa caatagggca                                    30

<210> SEQ ID NO 15
<211> LENGTH: 30
<212> TYPE: DNA
<213> ORGANISM: Artificial Sequence
<220> FEATURE:
<223> OTHER INFORMATION: K ssDNA

<400> SEQUENCE: 15
aaaaaaaaaa taatctaatt ctggtcgcgg                                    30

<210> SEQ ID NO 16
<211> LENGTH: 30
<212> TYPE: DNA
<213> ORGANISM: Artificial Sequence
<220> FEATURE:
<223> OTHER INFORMATION: K' ssDNA

<400> SEQUENCE: 16
aaaaaaaaaa ccgcgaccag aattagatta                                    30

<210> SEQ ID NO 17
<211> LENGTH: 30
<212> TYPE: DNA
<213> ORGANISM: Artificial Sequence
<220> FEATURE:
<223> OTHER INFORMATION: L ssDNA

<400> SEQUENCE: 17
aaaaaaaaaa gtgattaagt ctgcttcggc                                    30

<210> SEQ ID NO 18
<211> LENGTH: 30
<212> TYPE: DNA
<213> ORGANISM: Artificial Sequence
<220> FEATURE:
<223> OTHER INFORMATION: L' ssDNA

<400> SEQUENCE: 18
aaaaaaaaaa gccgaagcag acttaatcac                                    30

<210> SEQ ID NO 19
<211> LENGTH: 30
<212> TYPE: DNA
<213> ORGANISM: Artificial Sequence
<220> FEATURE:
<223> OTHER INFORMATION: N ssDNA
```

```
<400> SEQUENCE: 19
aaaaaaaaaa gtcctcgctt cgtctatgag                                              30

<210> SEQ ID NO 20
<211> LENGTH: 30
<212> TYPE: DNA
<213> ORGANISM: Artificial Sequence
<220> FEATURE:
<223> OTHER INFORMATION: N' ssDNA

<400> SEQUENCE: 20
aaaaaaaaaa ctcatagacg aagcgaggac                                              30

<210> SEQ ID NO 21
<211> LENGTH: 30
<212> TYPE: DNA
<213> ORGANISM: Artificial Sequence
<220> FEATURE:
<223> OTHER INFORMATION: O ssDNA

<400> SEQUENCE: 21
aaaaaaaaaa cttcgtggct agtctgtgac                                              30

<210> SEQ ID NO 22
<211> LENGTH: 30
<212> TYPE: DNA
<213> ORGANISM: Artificial Sequence
<220> FEATURE:
<223> OTHER INFORMATION: O' ssDNA

<400> SEQUENCE: 22
aaaaaaaaaa gtcacagact agccacgaag                                              30
```